US008802437B2

(12) United States Patent
Tremblay et al.

(10) Patent No.: US 8,802,437 B2
(45) Date of Patent: Aug. 12, 2014

(54) MEGANUCLEASE REAGENTS OF USES THEREOF FOR TREATING GENETIC DISEASES CAUSED BY FRAME SHIFT/NON SENSE MUTATIONS

(75) Inventors: Jacques Tremblay, Quebec (CA); Frederic Cedrone, Paris (FR)

(73) Assignee: Cellectis, Paris (FR)

( * ) Notice: Subject to any disclaimer, the term of this patent is extended or adjusted under 35 U.S.C. 154(b) by 0 days.

(21) Appl. No.: 13/497,997

(22) PCT Filed: Sep. 24, 2010

(86) PCT No.: PCT/IB2010/054313
§ 371 (c)(1),
(2), (4) Date: Aug. 6, 2012

(87) PCT Pub. No.: WO2011/036640
PCT Pub. Date: Mar. 31, 2011

(65) Prior Publication Data
US 2012/0301456 A1 Nov. 29, 2012

Related U.S. Application Data

(60) Provisional application No. 61/272,434, filed on Sep. 24, 2009, provisional application No. 61/333,987, filed on May 12, 2010.

(51) Int. Cl.
*C12N 15/00* (2006.01)

(52) U.S. Cl.
USPC ......................................................... 435/440

(58) Field of Classification Search
None
See application file for complete search history.

(56) References Cited

U.S. PATENT DOCUMENTS

| | | | |
|---|---|---|---|
| 7,842,489 B2 | 11/2010 | Arnould et al. |
| 7,897,372 B2 | 3/2011 | Duchateau et al. |
| 8,206,965 B2 | 6/2012 | Arnould et al. |
| 8,211,685 B2 | 7/2012 | Epinat et al. |
| 8,426,177 B2 | 4/2013 | Gouble |
| 8,476,072 B2 | 7/2013 | Cabaniols et al. |
| 8,530,214 B2 | 9/2013 | Arnould et al. |
| 2006/0078552 A1 | 4/2006 | Arnould et al. |
| 2006/0153826 A1 | 7/2006 | Arnould et al. |
| 2006/0206949 A1 | 9/2006 | Arnould et al. |
| 2009/0220476 A1 | 9/2009 | Paques |
| 2009/0222937 A1 | 9/2009 | Arnould et al. |
| 2009/0271881 A1 | 10/2009 | Arnould et al. |
| 2010/0086533 A1 | 4/2010 | Montoya et al. |
| 2010/0146651 A1 | 6/2010 | Smith et al. |
| 2010/0151556 A1 | 6/2010 | Arnould et al. |
| 2010/0167357 A1 | 7/2010 | Fajardo Sanchez et al. |
| 2010/0203031 A1 | 8/2010 | Grizot et al. |
| 2010/0229252 A1 | 9/2010 | Perez-Michaut |
| 2011/0033935 A1 | 2/2011 | Jantz et al. |
| 2011/0072527 A1 | 3/2011 | Duchateau et al. |
| 2011/0091441 A1 | 4/2011 | Gouble et al. |
| 2011/0151539 A1 | 6/2011 | Arnould et al. |
| 2011/0158974 A1 | 6/2011 | Duchateau et al. |
| 2011/0173710 A1 | 7/2011 | Grizot et al. |
| 2011/0179506 A1 | 7/2011 | Grizot |
| 2011/0179507 A1 | 7/2011 | Paques |
| 2011/0191870 A1 | 8/2011 | Paques |
| 2011/0207199 A1 | 8/2011 | Paques et al. |
| 2011/0225664 A1 | 9/2011 | Smith |
| 2011/0239319 A1 | 9/2011 | Danos et al. |
| 2012/0159659 A1 | 6/2012 | Arnould et al. |
| 2012/0171191 A1 | 7/2012 | Choulika et al. |
| 2012/0244131 A1 | 9/2012 | Delacote et al. |
| 2012/0258537 A1 | 10/2012 | Duchateau et al. |
| 2012/0260356 A1 | 10/2012 | Choulika et al. |
| 2012/0272348 A1 | 10/2012 | Danos et al. |
| 2012/0288941 A1 | 11/2012 | Arnould et al. |
| 2012/0288942 A1 | 11/2012 | Arnould et al. |
| 2012/0288943 A1 | 11/2012 | Arnould et al. |
| 2012/0304321 A1 | 11/2012 | Arnould et al. |
| 2012/0317664 A1 | 12/2012 | Arnould et al. |
| 2012/0322689 A1 | 12/2012 | Epinat et al. |
| 2012/0331574 A1 | 12/2012 | Arnould et al. |
| 2013/0059387 A1 | 3/2013 | Smith et al. |

(Continued)

FOREIGN PATENT DOCUMENTS

| | | |
|---|---|---|
| WO | 2007 049156 | 5/2007 |
| WO | 2009 076292 | 6/2009 |
| WO | WO 2010050802 A2 * | 5/2010 |

OTHER PUBLICATIONS

Aartsma-Rus A et al. Therapeutic antisense-induced exon skipping in cultured muscle cells from six different DMD patients. 2003. Human Molecular Genetics. vol. 12, No. 8. pp. 907-914.*

(Continued)

*Primary Examiner* — David J Steadman
*Assistant Examiner* — Paul Holland
(74) *Attorney, Agent, or Firm* — Oblon, Spivak, McClelland, Maier & Neustadt, L.L.P.

(57) ABSTRACT

The present invention relates to a method to treat a genetic disease in an individual caused by at least one frame shift or at least one non sense mutation in the human dystrophin gene comprising at least the step of bringing into contact at least one meganuclease enzyme, which recognizes and cuts a target site in the human dystrophin gene, with the genome of said individual under conditions wherein said at least one meganuclease recognizes and cleaves its target site in the human dystrophin gene. Said method applies also to a set of meganuclease enzymes, which each recognizes and cuts a different target site. The present invention also relates to a kit comprising, at least one meganuclease enzyme as defined above and medicament comprising said meganuclease.

8 Claims, 8 Drawing Sheets

(56) References Cited

U.S. PATENT DOCUMENTS

Figure 2:
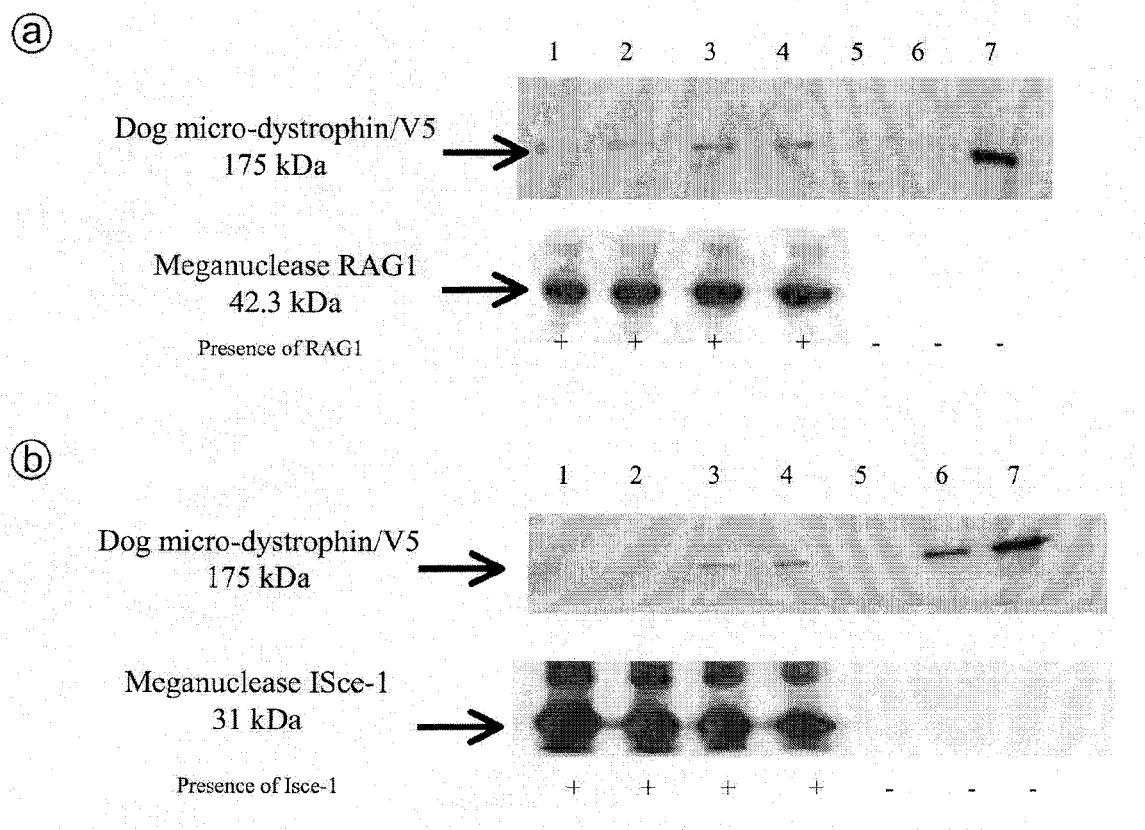

| | | | |
|---|---|---|---|
| 2013/0061341 | A1 | 3/2013 | Arnould et al. |
| 2013/0067607 | A1 | 3/2013 | Arnould et al. |
| 2013/0203840 | A1 | 8/2013 | Arnould et al. |
| 2013/0209437 | A1 | 8/2013 | Paques |
| 2013/0227715 | A1 | 8/2013 | Danos et al. |
| 2013/0236946 | A1 | 9/2013 | Gouble |
| 2013/0326644 | A1 | 12/2013 | Paques |
| 2014/0004608 | A1 | 1/2014 | Cabaniols et al. |
| 2014/0017731 | A1 | 1/2014 | Gouble et al. |

OTHER PUBLICATIONS

Lavigne MD et al. Nuclear-targeted chimeric vector enhancing nonviral gene transfer into skeletal muscle of Fabry mice in vivo. 2008. The FASEB Journal. vol. 22. pp. 2097-2107.*

Nowak KJ et al. Duchenne muscular dystrophy and dystrophin: pathogenesis and opportunities for treatment. 2004. EMBO Reports. vol. 5 No. 9. pp. 872-876.*

Chapdelaine, P., et al., "Meganucleases can restore the reading frame of mutated dystrophin," Gene Therapy, vol. 17 No. 7, pp. 846-858, (Jul. 2010).

Arnould, S., et al., "Engineering of Large Numbers of Highly Specific Homing Endonucleases that Induce Recombination on Novel DNA Targets," Journal of Molecular Biology, vol. 355, No. 3, pp. 443-458, (Jan. 20, 2006).

Smith, J., et al., "A combinatorial approach to create artificial homing endconucleases cleaving chosen sequences," Nucleic Acids Research, vol. 34, No. 22, pp. e149-1-e149-12, (Nov. 27, 2006).

Rosen, L.E., et al., "Homing endonuclease I-CreI derivatives with novel DNA target specificities," Nucleic Acids Research, vol. 34, No. 17, pp. 4791-4800, (Sep. 13, 2006).

Seligman, L.M., et al., "Mutations altering the cleavage specificity of a homing endonuclease," Nucleic Acids Research, vol. 30, No. 17, pp. 3870-3879, (Sep. 1, 2002).

Chevalier, B., et al., "Flexible DNA Target Site Recognition by Divergent Homing Endonuclease Isoschizomers I-CreI and I-MsoI," Journal of Molecular Biology, vol. 329, No. 2, pp. 253-269, (May 30, 2003).

Paques, F., et al., "Meganucleases and DNA Double-Strand Break-Induced Recombination: Perspectives for Gene Therapy," Current Gene Therapy, vol. 7, No. 1, pp. 49-66, (Feb. 1, 2007).

Gouble, A., et al., "Efficient in toto targeted recombination in mouse liver by meganuclease-induced double-strand break," The Journal of Gene Medicine, vol. 8, No. 5, pp. 616-622, (May 1, 2006).

International Search Report Issued Apr. 19, 2011 in PCT/IB10/54313 Filed Sep. 24, 2010.

* cited by examiner

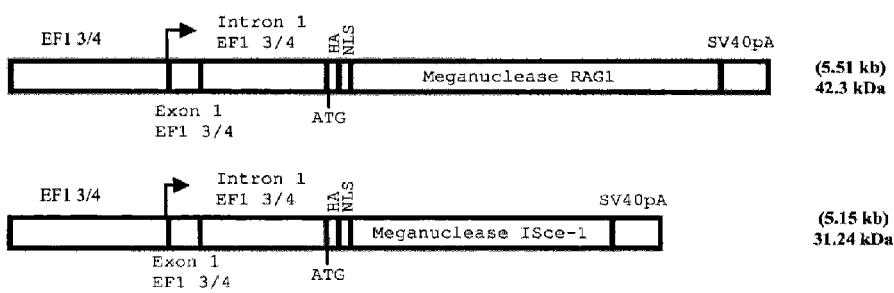

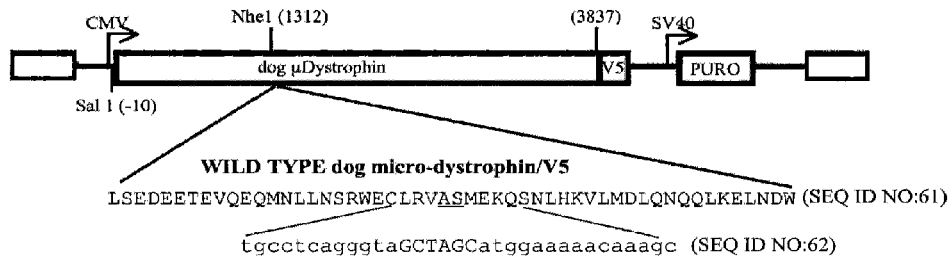

MUTATED dog micro-dystrophin/V5 by insertion of the RAG1 or ISce-1 TARGET

MUTATED dog micro-dystrophin/V5 RAG1 or ISce-1

LSEDEETEVQEQMNLLNSRWECLRVHCSQVPQPAC-HGKTKQFT-SSNGSPE (SEQ ID NO:63)

tgcctcagggtacatt gttctcaggtacctcagcca catGCTAGCatggaaaaacaaagc (SEQ ID NO:64)

LSEDEETEVQEQMNLLNSRWECLRVHARDNRVIC-HGKTK (SEQ ID NO:65)

tgcctcagggtacacg ctagggataacagggtaa catGCTAGCatggaaaaacaaagc (SEQ ID NO:66)

FIGURE 1

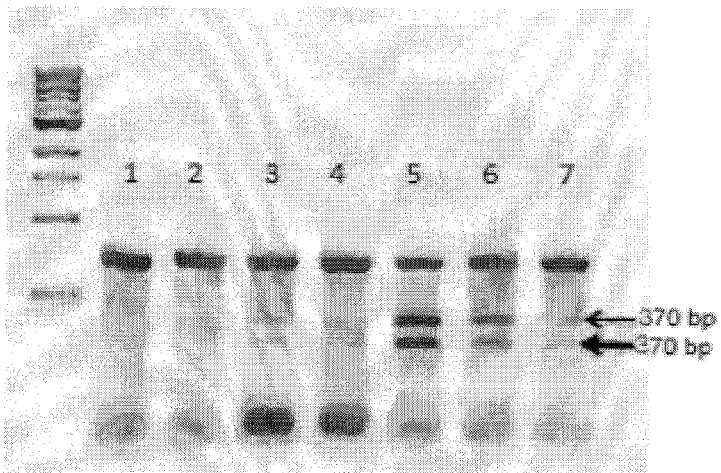

1) DNA from μ-dyst/V5$_{Rag1}$ cells not nucleofected with a meganuclease

2) DNA from μ-dyst/V5$_{I-Scel}$ cells not nucleofected with a meganuclease

3) DNA from μ-dyst/V5$_{Rag1}$ cells nucleofected with Rag1 meganuclease

4) DNA from μ-dyst/V5$_{I-Scel}$ cells nucleofected with I-Scel meganuclease

5) DNA from μ-dyst/V5$_{Rag1}$ + DNA from μ-dyst/V5$_{I-Scel}$ cells in a ratio of 1/1

6) DNA from μ-dyst/V5$_{Rag1}$ cells + DNA from μ-dyst/V5$_{I-Scel}$ cells in a ratio of 5/1

7) DNA from μ-dyst/V5$_{Rag1}$ cells + DNA from μ-dyst/V5$_{I-Scel}$ cells in a ratio of 10/1

Figure 7

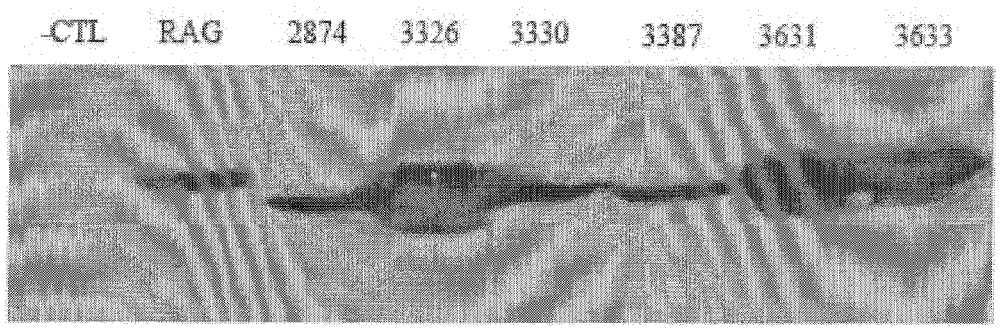

Figure 8

MEGANUCLEASE REAGENTS OF USES THEREOF FOR TREATING GENETIC DISEASES CAUSED BY FRAME SHIFT/NON SENSE MUTATIONS

The present application claims the benefit of U.S. provisional application Ser. No. 61/333,987, filed on May 12, 2010, and of U.S. provisional application Ser. No. 61/272,434, filed on Sep. 24, 2009.

The present invention relates to methods which use one or more meganuclease enzymes which can recognise and cleave a target in a gene in which a frame shift and/or non sense mutation exists which causes a human genetic disease, to correct the frame shift mutation in the gene and so cure the genetic disease. In particular the present invention relates to meganucleases which can cleave targets in the human dystrophin gene.

Duchenne Muscular Dystrophy (DMD) is a hereditary disease caused by mutations of the dystrophin gene, which leads to a premature termination of the dystrophin protein due to the presence of a nonsense mutation or a frame shift mutation, which results in a premature stop codon. These truncated dystrophin proteins cannot integrate into the dystrophin complex under the sarcolemma [1] leading to the absence of this protein [2] which in turn leads to severe muscle wastage meaning most patients are confined to a wheel chair by their teens and mortality usually occurs before the age of 40. By contrast, deletions within the dystrophin gene, which maintain the reading-frame, give rise either to asymptomatic subjects or to a Becker dystrophy in which the internally deleted form of dystrophin (with its amino- and carboxy-terminal ends intact) is present under the sarcolemma. Becker dystrophy is usually less severe than DMD, with some patients reportedly able to walk with a cane until age 65 [3].

There are currently several therapies being pursued for DMD, each with certain advantages and disadvantages:

(1) In vivo gene therapy with adeno-associated virus (AAV) vectors [4-8]. This approach uses AAV to introduce a truncated version of the dystrophin cDNA called micro-dystrophin or mini-dystrophin. Experiments in mdx mice, the standard DMD animal model, have shown that this micro-dystrophin can protect the muscle fibers and prevent the development of the disease [9]. Nevertheless, there are some potential drawbacks to this therapeutic approach including: the limited size of the possible insert due to packaging limit of the vector, this can mean that the truncated micro-dystrophin or mini-dystrophin gene included in the vector can not fully functionally replace the full length dystrophin in the patient; a further problem is the immune response against the AAV capsids and risks of random integration of the vector leading to further pathologies associated with this insertional mutagenesis.

(2) Cell transplantation therapy of muscle precursor cells (myoblasts, satellite cells, muscle-derived stem cells, mesoangioblasts or pericytes) [10-15]. In this approach, transplanted cells fuse with the host muscle fibers to introduce a few normal nuclei containing the normal dystrophin gene. A recent clinical trial demonstrated that myoblast transplantation does indeed restore the expression of dystrophin in up to 34% of the muscle fibers [10, 11]. However, potential limitations of this strategy include: the need to perform injections every mm of muscle (due to inefficient migration of myoblasts and the need to maintain sustained immunosuppression in patients due to the use of allogeneic cells for transplant.

(3) Pharmacologic rescue of a nonsense mutation in dystrophin using a drug such as PTC124 [16, 17]. This appears to be a promising approach but will likely be useful for less than 13-15% of DMD patients as it appears these drugs may work better for some types of non-sense mutations than others. Moreover, this drug would have to be used throughout the life of the patients and at present its long-term toxicity has not yet been evaluated.

(4) "Exon skipping" strategies, which aim to restore translation of carboxy-terminally truncated dystrophin mutants. This strategy is a promising approach for treating a large fraction of the DMD patients with a non-sense mutation, a micro-deletion or a deletion of one or several exons [18-20]. The main objective of exon-skipping strategies is to bypass one or more exons containing a frame-shifting alteration or a stop codon and to thereby restore production of a dystrophin protein, which contains wild-type amino- and carboxy-terminal sequences. Depending upon the part of the protein, which is missing, the resulting dystrophin proteins might still be able to incorporate in the dystrophin complex, essentially converting DMD patients into Becker-type patients with a less severe phenotype. Exon skipping can be induced with a short antisense oligonucleotide directed by complementarity to a splice donor or a splice acceptor sequence. To avoid rapid degradation of the oligonucleotides, they are synthesized using chemically modified 2'-O-methyl modified bases on a phosphorothioate backbone and phosphorodiamidate morpholino oligomers [21]. Nonetheless, a drawback of this approach is that, even if successful, it will require life-long administration of the exon skipping oligos. Another potential issue is that at present the long-term effects of repetitively administrating such non-degradable oligonucleotides to patients have not been investigated.

Specific gene targeting is the ultimate tool for making beneficial genetic modifications to treat a variety of genetic diseases, but its use is often limited by its low efficiency. In a number of recent studies, site-specific DNA double-strand breaks (DSBs) have been used to induce efficient gene targeting in chosen genes [22] [23, 24]. Meganucleases, also called homing endonucleases are sequence-specific endonucleases, which recognize and cleave unique large (>12 bp) target sites in living cells [25]. They can induce site-specific DSBs and thereby stimulate homologous recombination (HR) up to 10 000-fold in cultured cells [26, 27] in comparison to homologous recombination at a non-cleaved site.

Meganucleases have been used to induce HR in a variety of cell types and organisms (for review, see [28]) including mammalian cells, mice, plants, *Drosophila, E. coli* and trypanosome [29].

A meganuclease induced DSB can also be repaired by non-homologous end-joining (NHEJ), an error prone process, which frequently results in micro-insertions or micro-deletions (indels) at the site of the break [30].

Engineering highly specific, dedicated DNA endonucleases is the key to a wider usage of this technology. Several groups have developed methods to locally engineer natural meganucleases [31-33] and a combinatorial approach allowing for the complete redesign of the meganuclease DNA binding interface has been described [34].

These recently developments provide the potential to create reagents which target any chromosomal locus with engineered meganucleases.

The Applicants seeing the limitations with existing and proposed treatments for DMD and other genetic diseases associated with frame shift/nonsense mutations, have developed a new set of therapeutic materials and methods of using these to reverse the effects of the mutations causing DMD and other genetic diseases. In particular the inventors have shown that it is possible using a meganuclease to induce non-homologous end-joining (NHEJ) in the coding sequence of a gene of interest either ex vivo (upon an isolated tissue sample) or in vivo.

According to a first aspect of the present invention therefore there is provided a meganuclease enzyme which recognizes and cuts a target site in a gene of interest, wherein said gene of interest comprises at least one frame shift or nonsense mutation, for use in treating a disease caused by said at least one mutation.

In the present patent application a frameshift mutation is a genetic mutation caused by indels, ie. an insertion or deletion of a number of nucleotides that is not evenly divisible by three from a DNA coding sequence leading to an alteration in the codons of the following sequence and hence the final gene product.

In the present patent application a non sense mutation is a nucleotide change which changes a codon that specified an amino acid to one of the STOP codons (TAA, TAG, or TGA) and hence leading to a truncated final gene product.

There are a number of advantages of the approach developed by the inventors over other therapeutic strategies currently under active investigation. These include:

(1) No need for repeated long-term administration of treatment, because this therapeutic approach using meganucleases will induce permanent changes in the targeted gene of the affected progenitor cell lines and so, this treatment does not need to be given multiple times.

(2) This treatment will also avoid the use of viral vectors, which can have undesirable side effects due to uncontrolled integration events and/or adverse immune responses.

(3) This treatment will avoid the administration of non-degradable oligonucleotides.

(4) This treatment utilizes well-established and cost-effective technologies for producing pure recombinant proteins under Good Manufacturing Practice conditions.

In particular the genetic disease is one caused by a recessive mutation.

The Applicants have shown that meganucleases according to the present invention can be used for two novel strategies to correct different mutations in a variety of genes responsible for various genetic diseases, including dystrophin.

These strategies are:

(1) Deletion of Nonsense Mutations.

Meganucleases may be used to induce a DSB at or within a few base pairs of a nonsense mutation in the targeted gene. Error-prone NHEJ-mediated repair of such a DSB leads to the introduction of micro-deletions at the DSB thereby eliminating the mutant stop codon. Assuming that the number of bases deleted for any given imperfect repair event is random, on average one out of three micro-deletions removes a number of base pairs that is a multiple of three. These deletions therefore not only eliminate the nonsense codon but also maintain the reading frame of the targeted gene. In the case of the dystrophin gene, the resulting dystrophin protein has a deletion of a few amino acids, which, by analogy with dystrophin variants found in Becker Muscular Dystrophy patients, might be expected to retain at least partial function.

(2) Restoration of Reading Frame for Frame-Shift Mutations.

As on average two-thirds of the indels introduced by meganuclease induced error-prone NHEJ will shift the reading frame of the coding sequence (i.e.—these alterations will be of lengths that are not multiples of 3 bps), 1 out of 3 indels lead to restoration of the reading frame for out of frame deletions. These indels, however, have to be induced at the end of the exon that precedes the out of frame deletion so that they do not induce a new stop codon within the modified exon. Alternatively, the indel could be induced at the beginning of the exon that follows the out of frame deletion, in the sequence that precedes the first stop codon induced by the frame shift deletion. As with exon-skipping strategies currently being pursued, the resulting dystrophin mRNA encodes a short altered amino acid sequence in the middle of the protein but have intact amino- and carboxy-terminal sequences. Such variants might therefore be expected to have at least partial activity. The Applicants note that in contrast to exon-skipping strategies, dystrophin alterations induced by meganucleases are permanent because the DNA rather than the mRNA is targeted and therefore does not require repeated treatment.

In particular the present invention relates to a meganuclease enzyme which recognizes and cuts a target site in the human dystrophin gene, for use in the treatment of a genetic disease caused by at least one frame shift or nonsense mutation in the human dystrophin gene.

In accordance with another aspect of the present invention there is provided a set of meganuclease enzymes which each recognise and cut a different target site in the human dystrophin gene, for use in the treatment of a genetic disease caused by at least one frame shift or nonsense mutation in the human dystrophin gene.

In accordance with another aspect of the present invention there is provided a method to treat a genetic disease in an individual caused by at least one frame shift or at least one non sense mutation in the human dystrophin gene comprising at least the step of:

bringing into contact at least one meganuclease enzyme, which recognizes and cuts a target site in the human dystrophin gene, with the genome of said individual under conditions wherein said at least one meganuclease recognizes and cleaves its target site in the human dystrophin gene.

In particular the method may involve a set of meganuclease enzymes, which each recognise and cut a different target site in the human dystrophin gene, being brought into contact with the genome of said individual.

The inventors have in the present patent application demonstrated that a DMD phenotype can be rescued using a meganuclease to correct a frame shift or nonsense mutation in the coding sequence of the dystrophin gene.

This novel therapeutic approach can be used for not only DMD but for many genetic diseases that are due to a non-sense mutation(s), a frame shift mutation(s) or to an out of frame deletion(s). Although specific meganucleases will need to be engineered for individual stop codon mutations, it is also likely that a single meganuclease will be able to re-establish the reading frame of multiple frame-shift mutations.

Although the dystrophin gene is not corrected in all of the nuclei of the muscle fibers, the correction of the dystrophin gene in only one nucleus is enough to restore the expression over several hundred microns of a muscle fiber. The inventors have previously shown that in mdx muscle, the introduction of one normal nucleus capable of producing dystrophin was able to restore the expression of dystrophin over a 400 µm length of the fiber despite the presence of several hundreds of nuclei that still harbored the mutated dystrophin gene [51].

It is known in the art that there are exons, which are more frequently deleted than other in DMD. A table of the frequency of these deletions is available on the Center for Human and Clinical Genetics, Leiden University web site. Using this information and the sequences of the exons that precede or follow these deletions, it is possible to identify the sequences to be targeted by meganucleases to treat a high percentage of the DMD patients (see Tables 1A and 1B).

Tables 1A and 1B list the sequences which could be targeted by meganucleases, upstream and downstream of the frame shift mutation respectively, so as to restore the reading frame of the most frequent deletions observed in DMD patients from the Netherlands. The sequence to be targeted may be located at the end of the exon, which precedes the deletion. The number of by to be deleted has to take into account the reading frame switch. For a one reading frame shift, n+2 bp have to be deleted and for a two reading frame shift, n+1 bp is be deleted. However, the deletion must not induce a stop codon in the exon, which precedes the deletion. The sequence to be targeted by a meganuclease to restore the reading frame may also be located in the exon, which follows the deletion. However, this sequence has to be located before the first stop codon induced by the patient deletion. The sequence to be targeted to restore the reading frame for some frequent deletion, e.g., deletion of exon 44, may be the same as the sequence to be targeted for other less frequent deletion, e.g. deletion of exons 44 to 47. For the deletion of exons 46 and 47, which induces a frame shift of one, the complete sequence of the preceding exon (exon 45) can be targeted. However, for deletion of exons 46 to 50, which induces a frame shift of two, only the end of exon 45 can be targeted (sequence (6)). Sequence (6) can be targeted by the same meganuclease and could correct all deletions, which start at exon 46. Similarly, in patients, which have a deletion of exon 44, the sequence (4) at the beginning of exon 45 may be targeted by a meganuclease. The same meganuclease could be used to restore the reading frame of patients with a deletion of exons 46 to 47, or 46 to 48 or 46 to 49. Thus using this logic, the production of only a limited number of meganucleases targeting the sequences listed in Tables 1A and 1B, could restore the reading frame of approximately 50% of the DMD deletions.

TABLE 1A

| First Exon Deleted | Last Exon Deleted | Number of DMD Patients | % of DMD Patients | Number of Base Pairs Deleted | Frame Shift | Downstream Exon Targeted | Target Sequence* |
|---|---|---|---|---|---|---|---|
| 44 |  | 10 | 4.52 | 148 | 1 | 43 | AAGTTAACAAAA TGTACAAGGACCG ACAAGG (SEQ ID NO: 1) |
| 44 | 47 | 1 | 0.45 | 622 | 1 | 43 | AAGTTAACAAAA TGTACAAGGACCG ACAAGG (SEQ ID NO: 1) |
| 44 | 50 | 1 | 0.45 | 1019 | 2 | 43 | AGGGTGAAGCTA CAGGAAGCTCTCTC CCAGCTTGATTTCC AATGGGAAA (SEQ ID NO: 2) AAGTTAACAAAA TGTACAAGGACCG ACAAGG (SEQ ID NO: 1) |
| 44 | 52 | 1 | 0.45 | 1370 | 2 | 43 | AGGGTGAAGCTA CAGGAAGCTCTCTC CCAGCTTGATTTCC AATGGGAAA (SEQ ID NO: 2) AAGTTAACAAAA TGTACAAGGACCG ACAAGG (SEQ ID NO: 1) |
| 45 |  | 16 | 7.24 | 176 | 2 | 44 | TGGCTAACAGAA GCTGAACAGTTTCT CAGAAAGACACAA ATTCCTGAGAATTG GGAACATGCTAAAT ACAAATGGTATCTT AAG (SEQ ID NO: 3) |
| 45 | 54 | 3 | 1.36 | 1589 | 2 | 44 | TGGCTAACAGAA GCTGAACAGTTTCT CAGAAAGACACAA ATTCCTGAGAATTG GGAACATGCTAAAT ACAAATGGTATCTT AAG (SEQ ID NO: 3) |
| 46 | 47 | 6 | 2.71 | 298 | 1 | 45 | GAACTCCAGGAT GGCATTGGGCAGC GGCAAACTGTTGTC AGAACATTGAATGC (SEQ ID NO: 4) |

TABLE 1A-continued

| First Exon Deleted | Last Exon Deleted | Number of DMD Patients | % of DMD Patients | Number of Base Pairs Deleted | Frame Shift | Downstream Exon Targeted | Target Sequence* |
|---|---|---|---|---|---|---|---|
| | | | | | | | AACTGGGGAAGA AATAATTCAGCAAT CCTCAAAAACAGAT GCCAGTATTCTACA GGAAAAATTGGGA (SEQ ID NO: 5) AGCCTGAATCTGC GGTGGCAGGAGGT CTGCAAACAGCTGT CAGACAGAAAAAA GAG (SEQ ID NO: 6) |
| 46 | 48 | 3 | 1.36 | 484 | 1 | 45 | GAACTCCAGGAT GGCATTGGGCAGC GGCAAACTGTTGTC AGAACATTGAATGC (SEQ ID NO: 4) AACTGGGGAAGA AATAATTCAGCAAT CCTCAAAAACAGAT GCCAGTATTCTACA GGAAAAATTGGGA (SEQ ID NO: 5) AGCCTGAATCTGC GGTGGCAGGAGGT CTGCAAACAGCTGT CAGACAGAAAAAA GAG (SEQ ID NO: 6) |
| 46 | 49 | 3 | 1.36 | 586 | 1 | 45 | GAACTCCAGGAT GGCATTGGGCAGC GGCAAACTGTTGTC AGAACATTGAATGC (SEQ ID NO: 4) AACTGGGGAAGA AATAATTCAGCAAT CCTCAAAAACAGAT GCCAGTATTCTACA GGAAAAATTGGGA (SEQ ID NO: 5) AGCCTGAATCTGCG GTGGCAGGAGGTCTG CAAACAGCTGTCAGA CAGAAAAAGAG (SEQ ID NO: 6) |
| 46 | 50 | 6 | 2.71 | 695 | 2 | 45 | AGCCTGAATCTGC GGTGGCAGGAGGT CTGCAAACAGCTGT CAGACAGAAAAAA GAG (SEQ ID NO: 6) |
| 47 | 50 | 2 | 0.90 | 547 | 1 | 46 | AGCTTGAGCAAG TCAAG (SEQ ID NO: 28) |
| 47 | 52 | 3 | 1.36 | 898 | 1 | 46 | AGCTTGAGCAAG TCAAG (SEQ ID NO: 28) |
| 47 | 54 | 1 | 0.45 | 1265 | 2 | 46 | CAACTAAAAGAA AAGCTTGAGCAAGT CAAG (SEQ ID NO: 29) |
| 48 | 50 | 8 | 3.62 | 397 | 1 | 47 | AAAATAAGCTCA AGCAGACAAATCTC CAGTGGATAAAG (SEQ ID NO: 30) |

TABLE 1A-continued

| First Exon Deleted | Last Exon Deleted | Number of DMD Patients | % of DMD Patients | Number of Base Pairs Deleted | Frame Shift | Downstream Exon Targeted | Target Sequence* |
|---|---|---|---|---|---|---|---|
| 48 | 52 | 6 | 2.71 | 748 | 1 | 47 | AAAATAAGCTCAAGCAGACAAATCTCCAGTGGATAAAG (SEQ ID NO: 30) |
| 49 | 50 | 10 | 4.52 | 211 | 1 | 48 | CATTTGACGTTCAG (SEQ ID NO: 31) |
| 49 | 52 | 4 | 1.81 | 562 | 1 | 48 | CATTTGACGTTCAG (SEQ ID NO: 31) |
| 49 | 54 | 1 | 0.45 | 929 | 2 | 48 | CAGTTAAATCATCTGCTGCTGTGGTTATCTCCTATTAGGAATCAGTTGGAAATTTATAACCAACCAAACCAAGAAGGACCATTTGACGTTCAG (SEQ ID NO: 32) |
| 50 | | 6 | 2.71 | 109 | 1 | 49 | TGTCTAAAGGGCAGCATTTGTACAAGGAAAAACCAGCCACTCAGCCAGTGAAG (SEQ ID NO: 33) |
| 50 | 52 | 2 | 0.90 | 460 | 1 | 49 | TGTCTAAAGGGCAGCATTTGTACAAGGAAAAACCAGCCACTCAGCCAGTGAAG (SEQ ID NO: 33) |
| 51 | | 6 | 2.71 | 233 | 2 | 50 | GGACTGACCACTATTGGAGCCT (SEQ ID NO: 34) |
| 51 | 53 | 2 | 0.90 | 563 | 2 | 50 | GGACTGACCACTATTGGAGCCT (SEQ ID NO: 34) |
| 51 | 60 | 1 | 0.45 | 1775 | 2 | 50 | GGACTGACCACTATTGGAGCCT (SEQ ID NO: 34) |
| 52 | | 8 | 3.62 | 118 | 1 | 51 | TTACTAAGGAAACTGCCATCTCCAAACTAGAAATGCCATCTTCCTTGATGTTGGAGGTACCTGCTCTGGCA (SEQ ID NO: 35) |
| Total | | | 49.77 | | | | |

TABLE 1B

| First Exon Deleted | Last Exon Deleted | Number of DMD Patients | % of DMD Patients | Number of Base Pairs Deleted | Frame Shift | Upstream Exon Targeted | Target Sequence* |
|---|---|---|---|---|---|---|---|
| 44 | | 10 | 4.52 | 148 | 1 | 45 | GAACTCCAGGATGGCATTGGGCAGCGGCAAACTGTTGTCAGAACATTGAATGC (SEQ ID NO: 4) |

TABLE 1B-continued

| First Exon Deleted | Last Exon Deleted | Number of DMD Patients | % of DMD Patients | Number of Base Pairs Deleted | Frame Shift | Upstream Exon Targeted | Target Sequence* |
|---|---|---|---|---|---|---|---|
| 45 | | 16 | 7.24 | 176 | 2 | 46 | GCTAGAAGAACAAAAGAATATCTTGTCAGAATTTCAAAGAGATTTAAATGAATTT (SEQ ID NO: 5) |
| 44 | 47 | 1 | 0.45 | 622 | 1 | 48 | GTTTCCAGAGCTTTACCTGAGAAACAAGGAGAAATTGAAGCTCAAATAAAAGA (SEQ ID NO: 7) |
| 46 | 47 | 6 | 2.71 | 298 | 1 | 48 | GTTTCCAGAGCTTTACCTGAGAAACAAGGAGAAATTGAAGCTCAAATAAAAGA (SEQ ID NO: 7) |
| 44 | 50 | 1 | 0.45 | 1019 | 2 | 51 | CTCCTACTCAGACTGTTACTCTGGTGACACA (SEQ ID NO: 8) ACCTGTGGTTACTAAGGAA (SEQ ID NO: 9) |
| 45 | 50 | 10 | 4.52 | 871 | 1 | 51 | CTCCTACTCAGACTGTTACTCTGGTGACACA (SEQ ID NO: 8) |
| 46 | 50 | 6 | 2.71 | 695 | 2 | 51 | CTCCTACTCAGACTGTTACTCTGGTGACACA (SEQ ID NO: 8) ACCTGTGGTTACTAAGGAA (SEQ ID NO: 9) |
| 48 | 50 | 14 | 6.33 | 397 | 1 | 51 | CTCCTACTCAGACTGTTACTCTGGTGACACA (SEQ ID NO: 8) |
| 49 | 50 | 10 | 2.54 | 211 | 1 | 51 | CTCCTACTCAGACTGTTACTCTGGTGACACA (SEQ ID NO: 8) |
| 46 | 51 | 3 | 0.76 | 928 | 1 | 52 | GCAACAATGCAGGATTTGGAACAGAGGCGTCCCCAGTTGGAAGAACTCATTACCGCTGCCCAAAATTTGAAAAA (SEQ ID NO: 36) |
| | 51 | 6 | 1.52 | 233 | 2 | 52 | GCAACAATGCAGGATTTGGAACAGAGGCGTCCCCAGTTGGAAGAACTCATTACCGCTGCCCAAAATTTGAAAAA (SEQ ID NO: 36) CAAGACCAGCAATCAAGAGGCTAGAACA (SEQ ID NO: 37) |

TABLE 1B-continued

| First Exon Deleted | Last Exon Deleted | Number of DMD Patients | % of DMD Patients | Number of Base Pairs Deleted | Frame Shift | Upstream Exon Targeted | Target Sequence* |
|---|---|---|---|---|---|---|---|
| 48 | 52 | 5 | 2.26 | 748 | 1 | 53 | TTGAAAGAAT TCAGAATCAGTG GGATGAAGTACA AGAACACCTTCA GAACCGGAGGCA ACAGTTGAATGA (SEQ ID NO: 11) |
| 45 | 52 | 7 | 3.17 | 1222 | 1 | 53 | TTGAAAGAAT TCAGAATCAGTG GGATGAAGTACA AGAACACCTTCA GAACCGGAGGCA ACAGTTGAATGA (SEQ ID NO: 11) |
| Total | | | 39.21 | | | | |

*Wherein: (1) - SEQ ID NO: 1; (2) - SEQ ID NO: 2; (3) - SEQ ID NO: 3; (4) - SEQ ID NO: 4; (5) - SEQ ID NO: 5; (6) - SEQ ID NO: 6; (7) - SEQ ID NO: 7; (8) - SEQ ID NO: 8; (9) - SEQ ID NO: 9; (10) - SEQ ID NO: 10; (11) - SEQ ID NO: 11; (12) - SEQ ID NO: 28; (13) - SEQ ID NO: 29; (14) - SEQ ID NO: 30; (15) - SEQ ID NO: 31; (16) - SEQ ID NO: 32; (17) - SEQ ID NO: 33; (18) - SEQ ID NO: 34; (19) - SEQ ID NO: 35; (20) - SEQ ID NO: 36; (21) - SEQ ID NO: 37.

In particular the target site is located at the end of the exon preceding said at least one frame shift/non sense mutation.

The present invention therefore can use a meganuclease which targets a sequence upstream of the frame shift/non sense mutation in the genome.

Alternatively the target site is located after said at least one frame shift mutation in the exon.

The present invention therefore can use a meganuclease which targets a sequence downstream of the frame shift/non sense mutation in the genome.

In particular the target site is selected from the group consisting of: SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO:11; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; SEQ ID NO: 36; SEQ ID NO: 37.

Alternatively the target site may be selected from any suitable target in the human dystrophin gene (SEQ ID NO: 27).

In accordance with a further aspect of the present invention the meganuclease is a LAGLIDADG (SEQ ID NO: 81) endonuclease, such as I-Sce I, I-Chu I, I-Cre I, I-Csm I, PI-Sce I, PI-Tli I, PI-Mtu I, I-Ceu I, I-Sce II, I-Sce III, HO, PI-Civ I, PI-Ctr I, PI-Aae I, PI-Bsu I, PI-Dha I, PI-Dra I, PI-May I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I, I-MsoI, and PI-Tsp I; preferably, I-Sce I, I-Chu I, I-Dmo I, I-Csm I, PI-Sce I, PI-Pfu I, PI-Tli I, PI-Mtu I, and I-Ceu I.

The LAGLIDADG (SEQ ID NO: 81) family is the largest of the homing endonucleases families. This family is characterized by a conserved tridimensional structure, but displays very poor conservation at the primary sequence level, but for a short peptide above the catalytic center. This family has been called LAGLIDADG (SEQ ID NO: 81), after a consensus sequence for this peptide, found in one or two copies in each LAGLIDADG (SEQ ID NO: 81) protein.

Homing endonucleases with one LAGLIDADG (SEQ ID NO: 81) (L) are around 20 kDa in molecular mass and act as homodimers. Those with two copies (LL) range from 25 kDa (230 amino acids) to 50 kDa (HO, 545 amino acids) with 70 to 150 residues between each motif and act as a monomer. Cleavage of the target sequence occurs inside the recognition site, leaving a 4 nucleotide staggered cut with 3'OH overhangs.

The inventors prefer meganucleases selected from the LAGLIDADG (SEQ ID NO: 81) family as members of this family have previously been shown to be very amenable to engineering so as to alter their specificity and activity [31-34].

According to a further aspect of the present invention, the gene may also be specifically targeted by a pair of Zinc Finger Nucleases (ZFNs) [52-56]. Thus the approach that the inventors have demonstrated feasible with meganucleases could also be put into practice using pairs of ZFNs that target the same genomic sequences or any other suitable means.

In accordance with a further aspect of the present invention the meganucleases are coupled to protein transduction domains.

An attractive method for delivering dystrophin-targeted meganuclease in vivo is the use of protein transduction domains (PTDs) that can penetrate directly into muscle fibers. PTDs harbor a high density of basic amino acid residues (Arg and Lys), which are critical for their transduction function (recently extensively reviewed by Chauhan et al. [40]). Proteins as large as 110 kDa coupled to a PTD have been transduced into different cells [41] and systemic injection of such fusion proteins has demonstrated the effectiveness PTD-mediated protein delivery in vivo [41, 42]. Various active PTDs have been described including Penetratin, Polylysine, Polyarginine, Tat, VP22, [43] Syn B1 [44] FGF-4 [45, 46], anthrax toxin derivative 254-amino acids (aa) peptide segment, diphtheria toxin 'R' binding domain, MPG (HIV gp41/SV40 Tag NLS), pep-1, WR peptide, and exotoxin A. The protein transduction domain of the HIV Tat protein (11 amino acids: YGRKKRRQRRR SEQ ID NO: 12) has been used to efficiently transduce a coupled plasmid into skeletal muscles [47]. It has been shown that a Tat-EGFP fusion protein can penetrate muscle fibers [48]. Finally, VP22 fused with microdystrophin has been transduced into cells [49] while Tat-utrophin has been transduced directly into muscle fibers [50].

According to a further aspect of the present invention therefore there are provided meganuclease-PTD fusion proteins.

Such meganuclease-PTD fusion proteins efficiently deliver meganucleases in not only muscle fibers but potentially into satellite cells.

In particular the meganuclease or set of meganucleases, comprise a HIV TAT PTD.

It is possible that meganuclease-PTDs or ZFN-PTDs may be immunogenic but this may not be an issue as the proteins only need to be administered one time to effect permanent changes in the targeted gene. Another possibility might be to use transient immunosuppression when the proteins are administered.

According to a further aspect of the present invention the meganuclease or set of meganucleases as defined above, are encoded at least one purified nucleic acid molecule.

The present invention may be implemented using purified peptide versions of the meganucleases or alternatively the present invention may be implemented using purified nucleic acid molecules encoding these meganucleases.

According to a further aspect of the present invention there is provided a kit comprising, a purified meganuclease peptide or a set of purified meganuclease peptides or at least one purified nucleic acid encoding a meganuclease or a set of meganucleases as defined above and instructions for there use.

According to a further aspect of the present invention there is provided a medicament comprising:

a purified meganuclease peptide or a set of purified meganuclease peptides or at least one purified nucleic acid encoding a meganuclease or a set of meganucleases as defined above, or a pharmaceutically acceptable salt thereof; and further comprising at least one of
    a preservative;
    a stabiliser;
    an excipient;
    a vehicle.

In particular wherein the meganuclease or set of meganucleases comprise a protein transduction domain.

For a better understanding of the invention and to show how the same may be carried into effect, there will now be shown by way of example only, specific embodiments, methods and processes according to the present invention with reference to the accompanying drawings in which:

FIG. 1: Schematic representation of Meganucleases RAG1 and I-SceI (A) used for episomal gene repair of mutated plasmid dog micro-dystrophin/V5 (target) (B). (A). The expression of both meganucleases RAG1 and I-SceI is drived by translation elongation factor 1 alpha (EF-1a) promoter. The transcription unit is composed mainly by the presence of exon1 and intron 1 of EF-1a gene fused to MGN cDNA harboring HA-tag and a nuclear localization signal (NLS) at the N-terminal while SV40 polyadenylation site (SV40 polyA) is present in C-terminal following stop codon. (B). Plasmids containing the dog micro-dystrophin/V5 are represented under three different constructs. One of these constructs is the wild type micro-dystrophin/V5 (without target insertion) and the other two constructs show respectively insertion of specific target for RAG1 and I-SceI (nucleotide box) near of the NheI resulting in an out of frame expression of micro-dystrophin/V5 and creating stop codons (TAG underlined). The capital letters GCTAGC represent NheI restriction enzyme site coding for amino acids alanine (A) and serine (S) in wild type micro-dystrophin/V5 construct, while HCSQVPQPAC-HGKTKQFT-SSNGSPE (SEQ ID NO: 59) and HARDNRVIC-HESRI (SEQ ID NO: 60) represent respectively amino acid changes for mutated dog micro-dystrophin/V5 constructs containing a target for RAG1 or I-SceI.

FIG. 2: Western blot analysis of dog micro-dystrophin/V5 expression in 293FT cells showing that episomal gene repair by Meganucleases RAG1 and I-SceI is able to restore micro-dystrophin/V5 protein expression from the mutated dystrophin constructs. 293FT cells were co-transfected in 6 well plates with meganucleases RAG1 (A) or I-SceI (B) and mutated dog micro-dystrophin/V5 containing specific target for MGNs. (A). Dog micro-dystrophin/V5 expression shown in lanes 1 to 4 results from co-transfection in 293FT cells of different amounts of MGN RAG1 plasmid with the plasmid containing mutated dog micro-dystrophin/V5 containing RAG1. Lanes 1 and 2 contain 3.8 mg MGN RAG1+200 ng plasmid dystrophin target RAG1; lanes 3 and 4 contain 2.8 mg MGN RAG1+1200 ng plasmid micro-dystrophin/V5 with the RAG1 target. Lanes 5, 6 and 7 correspond to the following co-transfections: lane 5 (negative control): 1200 ng plasmid micro-dystrophin/V5 with the RAG1 target+2.8 mg of a plasmid containing EGFP; lanes 6 and 7 (positive controls) respectively: 200 ng or 1200 ng of wild type dog micro-dystrophin/V5+3.8 mg or 2.8 mg of a plasmid containing EGFP. (B) As for section A, the co-transfection mixes were as follows: lanes 1 and 2: 3.8 mg MGN I-SceI+200 ng of micro-dystrophin/V5 plasmid containing the I-SceI target; lanes 3 and 4: 2.8 mg MGN ISce1+1200 ng of the micro-dystrophin/V5 plasmid containing the ISce1 target; lane 5 (negative control): 1200 ng of the micro-dystrophin/V5 plasmid containing the ISce1 target+2.8 mg of a plasmid containing EGFP; lanes 6 and 7 (positive controls) respectively: 600 ng or 1200 ng of the wild type dog micro-dystrophin/V5 plasmid+3.4 mg or 2.8 mg of a plasmid containing EGFP.

Figure 3:
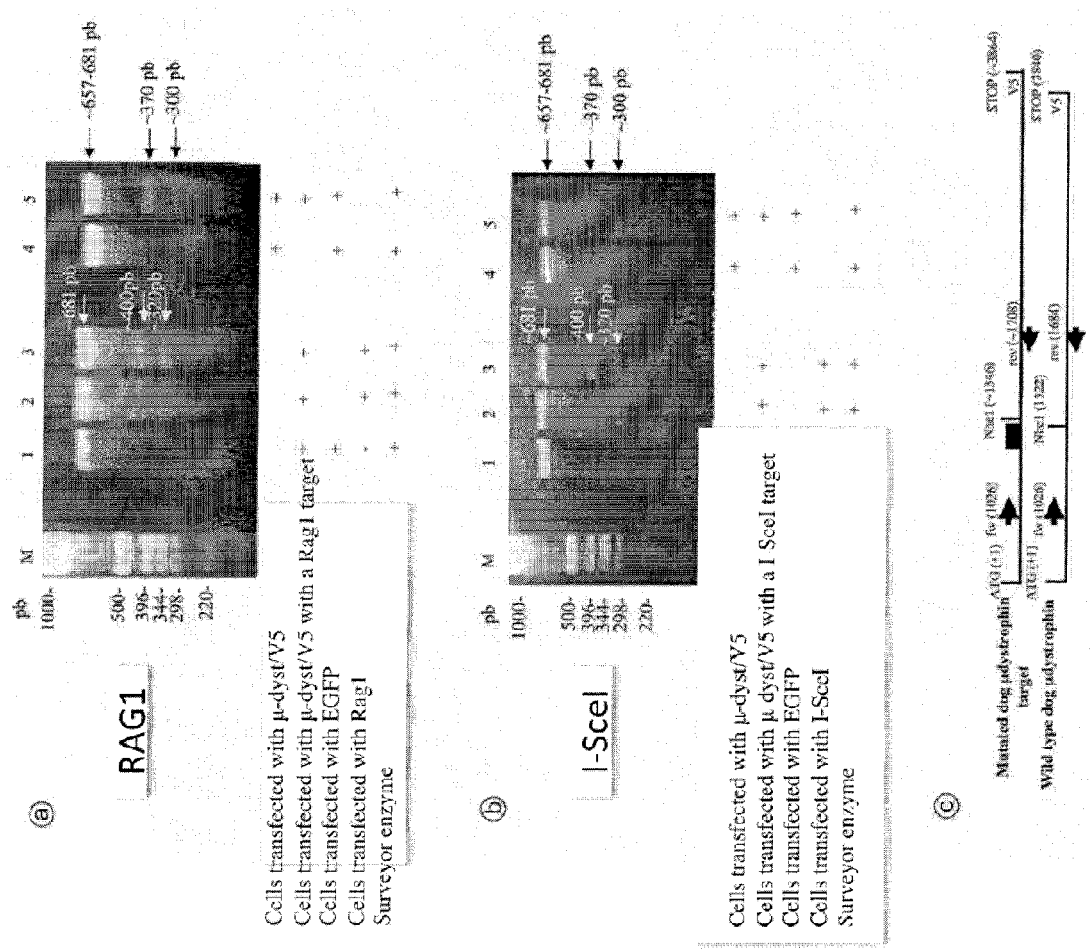

FIG. 3: Surveyor® nuclease digestion products of amplicons derived from mutated dog micro-dystrophin/V5 DNA treated with Meganucleases RAG1 or I-SceI in 293FT cells. In panels A and B, the 681-bp (lanes 1, 2 and 3) and the 657-681 amplicons (lanes 4 and 5) were obtained by PCR amplification with Phusion™ High-Fidelity DNA Polymerase and purified as described in the material and method section. These amplicons were generated from genomic DNA extracted from 293FT co-transfected with the mutated dog micro-dystrophin/V5 plasmid containing a specific target and the meganuclease plasmid specific for that target as described for western blot (FIGS. 2A and B), The 293FT cells from a given well were detached from the plate and divided in two parts: one for protein analysis by Western blot (FIG. 2) and the other for genomic DNA analysis. Amplicons obtained from genomic DNA were assessed for the presence of mismatches by digestion with the Surveyor® nuclease (FIGS. 3A and 3B, lanes 1, 2 and 3). In both panels A and B, the lanes 1 represent negative controls, i.e., amplicons originating from genomic DNA extracted from 293FT cells co-transfected with 1200 ng of a mutated micro-dystrophin/V5 plasmid containing either the target RAG1 or ISce1+2.8 mg and with a plasmid containing EGFP (this DNA originates from the same cells as those used in lanes 5 in Western blot, FIGS. 2A and B). These amplicons (homoduplex) were digested with the Surveyor® nuclease. This resulted in no specific cleavage as shown in the lanes 1 of the two panels. The lanes 2 and 3 of panels A and B represent products digestion by the Surveyor® nuclease of amplicon mixtures (homoduplex (negative control amplicon) and heteroduplex (amplicons produced from genomic DNA of 293FT cells co-transfected with a plasmid target and its specific MGN). The presence of amplicon heteroduplexes in lanes 2 and 3 for panels A and B was confirmed by the cleavage of the amplicon mixtures by the Surveyor® nuclease in specific fragments of 400 and 320 bp (white arrows). For panels A and B, the lanes 4 show the absence of specific cleavage by Surveyor® nuclease for amplicon (homoduplex) provided by genomic DNA from 293FT cells co-transfected with the wild type dog micro-dystrophine/V5 plasmid and with an EGFP plasmid. Lanes 5 represent specific cleavage by Surveyor® nuclease of the homoduplex mixture of amplicons originating from wild type micro-dystrophin/V5 plasmid and the mutated micro-dystrophin/V5 plasmid. In lanes 5 of both panels, the sizes of specific fragments (370 and 300 bp) following digestion by the Surveyor® nuclease were lower than those observed in lanes 2 and 3. The schema in C comparing the mutated dog micro-dystrophin/V5 with the wild type dog micro-dystrophin/V5 explains that the size differences of the fragments generated by the Surveyor® nuclease are due to the presence of the specific target for MGNs (black box) located near of the NheI site. Note the correspondence between the restoration of the expression of dystrophin observed by Western Blot (FIGS. 2A and B, lanes 1 and 2 or 3 and 4) and the cleavage by Surveyor® nuclease of a hetero/homoduplex in FIG. 3 (Panels A and B, lanes 2 or 3). These observations confirm the specificity of MGNs RAG1 and I-SceI for their own target present in mutated micro-dystrophin/V5 constructs.

Figure 4:
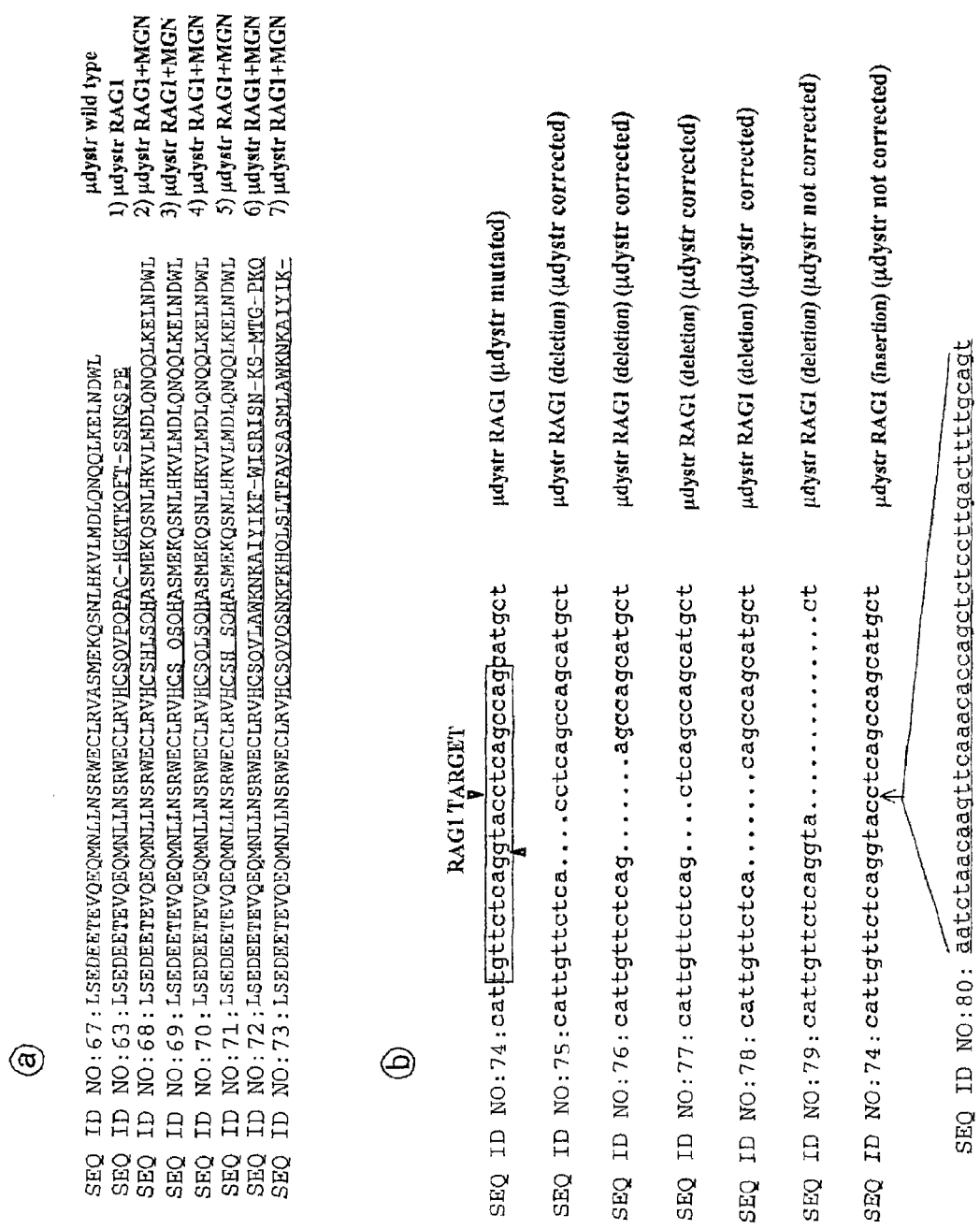

FIG. 4: Amino acid and DNA sequences of the mutated dog micro-dystrophin/V5 showing modification by the MGN RAG1 on its specific target leading to the restoration of the dystrophin expression. Two days after the co-transfection of 293FT cells with the a dog micro-dystrophin/V5 plasmid containing the RAG1 target and with after the RAG1 MGN, the region containing the RAG1 sequence was amplified, cloned and sequenced to confirm that the MGN cleavage was the molecular basis of the restoration of dystrophin expression observed in FIG. 2. (A) Amino acids sequence revealed that four clones (2, 3, 4 and 5) showed corrections of the micro-dystrophin/V5 expression but each of them differs in their amino acids (underlined). Two other clones (6 and 7) produced amino acid sequences that did not correspond to those of micro-dystrophin/V5 because the correct reading frame was not restored by the micro-deletion (lane 6) or the micro-insertion (lane 7). (B) Nucleotide sequence alignments revealed distinct MGN-induced insertions and deletions within the target region of RAG1 except for clone 7 showing more complex NHEJ mechanism. This figure illustrates that deletions or insertions induced by NHEJ are able to restore the normal reading frame of a mutated dystrophin gene.

Figure 5:
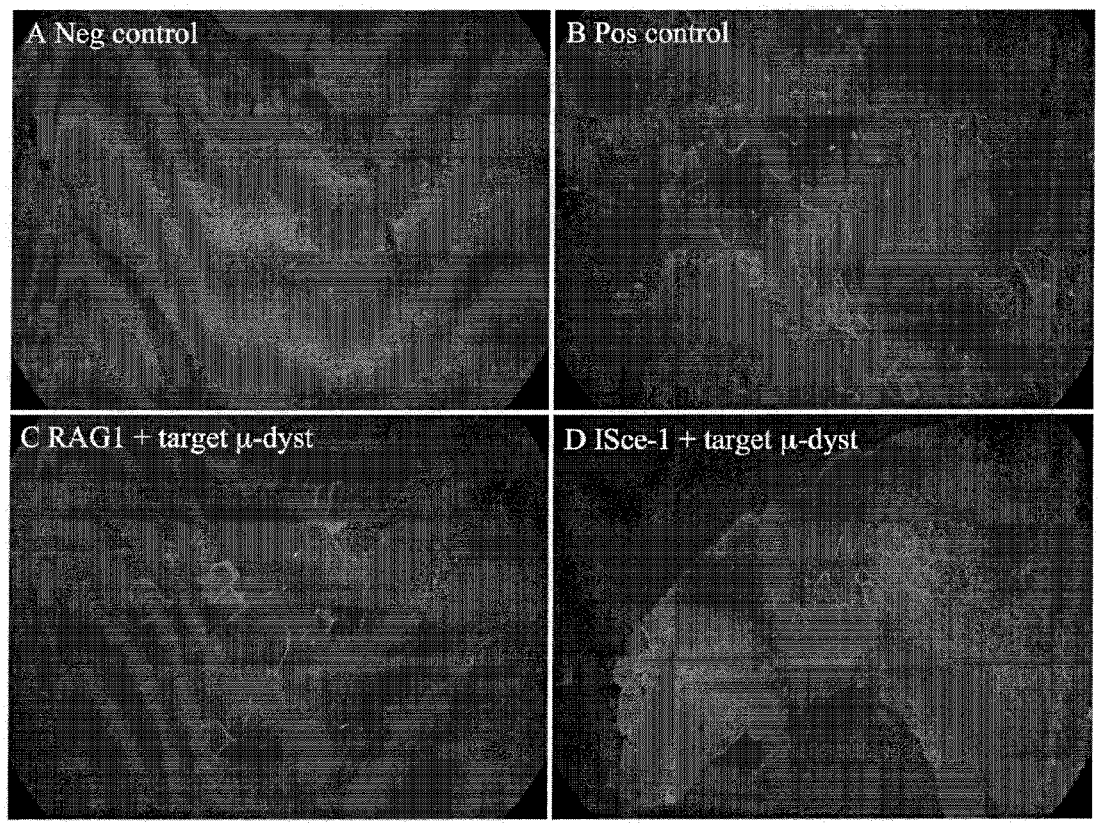

FIG. 5: Direct intramuscular co-electroporation in muscle fibers of a mutated dog micro-dystrophin/V5 plasmid containing a MGN target and of a MGN plasmid restored micro-dystrophin/V5 expression in vivo. In A) the micro-dystrophin/V5 plasmid with a MGN target sequence was electroporated alone in the muscle (as a negative control), only rare weakly labeled muscle fibers were detected 2 weeks later by immunohistochemistry (in red) using an anti-V5 mAb. In B) the micro-dystrophin/V5 plasmid without a MGN target sequence was electroporated alone in the muscle (as a positive control), abundant muscle fibers expressed the V5 epitope. In C) the micro-dystrophin/V5 plasmid with a RAG1 target sequence was co-electroporated with a plasmid coding for RAG1, abundant muscle fibers expressed the V5 epitope. In D) the micro-dystrophin/V5 plasmid with an I-SceI target sequence was co-electroporated with a plasmid coding for I-SceI, abundant muscle fibers expressed the V5 epitope. Figure E, summarizes for both MGNs at 2 different concentrations the total numbers of dystrophin/V5 muscle fibers observed in 10 sections collected throughout the muscles at 150 mm intervals.

Figure 6:
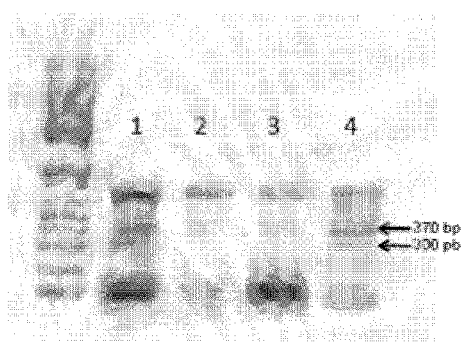

FIG. 6: The restoration of micro-dystrophin expression in the previous experiment is due to mutation of the targeted plasmids. Various plasmids were electroporated into mouse muscles: in lane 1 plasmids coding for the mutated micro-dystrophin/V5 containing a sequence targeted by I-SceI (m-dyst/V5$_{I-SceI}$) and for the I-SceI meganuclease; in lane 2 the plasmid coding for wild type micro-dystrophin (no target for the I-SceI meganuclease); in lane 3 the m-dyst/V5$_{I-SceI}$ electroporated alone. The DNA was extracted from these muscles 15 days later and the region targeted by the meganuclease I-SceI was amplified. The amplicons were then digested with the Surveyor® enzyme. The presence of the two bands at 300 and 370 bp are due to the presence of some hetero-duplexes that were cut by the Surveyor® enzyme confirming that the I-SceI meganuclease had mutated the micro-dystrophin target plasmid. Lane 4 is a positive control for the Surveyor® enzyme reaction. The DNA of myoblasts electroporated with a plasmid coding for mutated micro-dystrophin containing a sequence targeted by I-SceI (m-dyst/V5$_{I-SceI}$) was mixed with the DNA of myoblasts electroporated with a plasmid coding for mutated micro-dystrophin containing a sequence targeted by Rag1 (m-dyst/V5$_{Rag1}$). The targeted regions were amplified and digested with the Surveyor® enzyme. As heterodimers were formed the Surveyor® enzyme cut the amplicons.

FIG. 7 Mutations by meganucleases of targeted micro-dystrophin genes integrated in myoblasts. The lentivirus used contain, under a CMV promoter, either a mutated micro-dystrophin/V5 gene with a inserted target sequence for Rag1 (m-dyst/V5$_{Rag1}$) or a mutated micro-dystrophin/V5 gene with a inserted target sequence for I-SceI (m-dyst/V5$_{I-SceI}$). These lentivirus also contained a puromycin resistance gene under a SV40 promoter. These lentivirus were used to infect human myoblasts. The day before the infection, 250 000 myoblasts were seeded per well in a 6 wells plate. For the infection, the medium was removed and replaced by 3 ml of 0.45 µl filtered supernatant from 293T lentivirus producing cells. The human myoblasts were obtained from a muscle biopsy of a healthy cadaveric donor. After an overnight incubation, the medium was changed by 3 ml of MB1 medium and cells were proliferated 48 h. The infected cells were than selected with puromycin at 2 µg/ml. After 48 h with the selection agent (time required to kill all control cells without virus), the medium was changed and cells were proliferated until they reached confluence. Cells were than ready to perform nucleofection experiment with a meganuclease plasmid. Some selected myoblasts were than nucleofected with a plasmid coding either for the Rag1 meganuclease or the I-SceI meganuclease. Control myoblasts were not nucleofected with a meganuclease. Three days later the DNA was extracted from all myoblasts. The region coding for the targeted sequences for Rag1 or I-SceI were amplified by PCR. These amplicons were then digested with the Surveyor® enzyme to verify the presence of hetero-dimers due to insertions or deletions produced by the meganuclease in the genome integrated micro-dystrophin V5 gene. The figure illustrates the results of the Surveyor® reactions. Lane 1 represents the Surveyor® product of amplicons obtained from myoblasts containing the m-dyst/V5$_{Rag1}$ but not nucleofected with a meganuclease. Lane 2 represents the Surveyor® product of amplicons obtained from myoblasts containing the m-dyst/V5$_{I-SceI}$ but not nucleofected with a meganuclease. In lanes 1 and 2, the highest band at 670 bp is the amplicon. The lowest band is the primer dimers. There are no bands at 300 and 370 bp because no meganuclease was nucleofected to mutate the m-dyst/V5 genes. Lane 3 represents the Surveyor® product of amplicons obtained from myoblasts containing the m-dyst/V5$_{Rag1}$ and nucleofected with the Rag1 meganuclease. Lane 4 represents the Surveyor® product of amplicons obtained from myoblasts containing the m-dyst/V5$_{I-SceI}$ and nucleofected with the I-SceI meganuclease. In lanes 3 and 4, there are bands at 300 and 370 bp because the adequate meganuclease was nucleofected to induce indels in the m-dyst/V5 genes. The presence of mutated amplicons led to a cut of the amplicons by the Surveyor® enzyme. Lanes 5, 6 and 7 are positive controls for the Surveyor® enzyme, e.i., the amplicons obtained from cells containing the m-dyst/V5$_{Rag1}$ were mixed in different proportions (respectively 1 to 1, 5 to 1 and 10 to 1) with the amplicons obtained from cells containing the m-dyst/V5$_{I-SceI}$ gene. As different inserts were present, heteroduplex were formed and were cut by the Surveyor® enzyme. In lanes 5, 6 and 7 as the DNA mixtures were 1 to 1, 5 to 1 and 10 to 1, there were respectively roughly 50%, 20% and 10% of hetero-duplexes that were formed and thus cut by the Surveyor® enzyme. Note than in lane 3, the intensity of the bands at 300 and 370 bp were slightly more than in lane 7 but less than lane 6, thus the Rag1 meganuclease (lane 3) as mutated between 10% and 20% of the target m-dyst/V5$_{Rag1}$.

FIG. 8: Expression of meganucleases DMD21, DMD31 and DMD33 in 293FT cells. Cells were washed twice in HBSS and were lysed in 200 μl of lysis buffer containing 20 mM Tris PH7.5, 1 mM DTT, 1 mM PMSF and 1% SDS. Protein samples were prepared as follows: In microtubes containing the 200 μl of lysed cells, 600 μl of methanol, 200 μl of chloroform, 500 μl of water were added. After each liquid addition, microtubes were vortexed. Microtubes were centrifuged one minute at 14800 RPM and the solid white phase at the interphase was recuperated and washed with 300 μl of methanol. White pellet were lyophilized. Pellets were boiled in 40 μl of loading buffer containing Tris pH6.8 0.25M, 10% SDS, 7.5% glycerol and 0.5% beta-mercaptoethanol. 10 μl were loaded on 10% gel SDS-page electrophoresis. After protein electrotransfert on nitrocellulose membrane, the membrane was blocked in PBS-Tween (0.05%) containing 5% milk for one hour. The membrane was incubated overnight at 4° C. with a rabbit anti-I-Cre antibody (1/20000). The membrane was washed 3 times 10 minutes in PBS-Tween (0.05%). After, the membrane was incubated one hour with a goat anti-rabbit-HRP antibody (1/2000), washed 3 times in PBS-Tween (0.05%) and revealed with a chemiluminescence kit. Lane CTL represents a control experiment (no meganuclease expression), lane RAG represents RAG expression, lanes 2874 and 3387 respectively represent DMD21 2874 and 3387 expression, lanes 3631 and 3633 respectively represent DMD31 3631 and 3633 expression, and lanes 3326 and 3330 respectively represent DMD33 3326 and 3330 expression.

There will now be described by way of example a specific mode contemplated by the Inventors. In the following description numerous specific details are set forth in order to provide a thorough understanding. It will be apparent however, to one skilled in the art, that the present invention may be practiced without limitation to these specific details. In other instances, well known methods and structures have not been described so as not to unnecessarily obscure the description.

EXAMPLE 1

Material and Methods

Meganucleases RAG1 and I-SceI.

Functional meganucleases (MGNs) RAG1 (SEQ ID NO: 18) and I-Sce-I (SEQ ID NO: 13) were used as plasmids containing a transcriptional unit as described in the FIG. 1A.

The nucleotide sequences of these constructs are provided as SEQ ID NO: 19 and SEQ ID NO: 21; the nucleotide sequences of the plasmids encoding these meganucleases are also provided, SEQ ID NO: 20 (pCLS2262 encoding RAG1) and SEQ ID NO: 22 (pCLS2209 encoding I-SceI).

Plasmid Vectors Containing the Dog Micro-Dystrophin Fused to V5 with Insertion of the RAG1 or I-SceI Target Sequence Dog micro-dystrophin cDNA (3.8 kb) (SEQ ID NO: 23) contained in an adeno-associated viral plasmid (gift from Dr Xiao Xiao [37], University of Pittsburgh, Pittsburgh, Pa.) was amplified by polymerase chain reaction (PCR) with Phusion™ High-Fidelity DNA Polymerase (New England Biolabs, Pickering, Canada). The amplification was performed using Forward 5'-gacagttatcaaacagctttggaag-3' (pos 1027-1051 dog microdystrophin cDNA) (SEQ ID NO: 25) and Reverse 5'-gtaatctgtgggtgtcttgtaaaaga-3' (pos 1684-1659 dog microdystrophin cDNA) (SEQ ID NO: 26). Amplification products were then treated 10 min at 72° C. with Taq DNA Polymerase (New England Biolabs) and cloned in a TA cloning vector, i.e., pDrive (Qiagen, Mississauga, Canada).

The resulting clones were sequenced to confirm the integrity of dystrophin nucleotide sequence. The micro-dystrophin cDNA was introduced in a directional TOPO vector (Invitrogen, Carlsbad, Calif.) in phase with epitope V5 present in the plasmid. The blasticidin resistance gene in the original vector has been replaced by a puromycin resistance gene. The final construct of dog micro-dystrophin cDNA was fused in C-terminal with the V5 epitope making the WILD TYPE micro-dystrophin/V5 (FIG. 1B). A unique SalI restriction site has been added to the 5' of this dog micro-dystrophin/V5 cDNA. The presence of another unique NheI site present at position 1313 within the micro-dystrophin cDNA permitted us to introduce specific target sites for MGN RAG1: 5'-ttgttctcaggtacctcagccagca-3' (SEQ ID NO: 14) or for MGN I-SceI: 5'-cacgctagggataacagggtaata-3' (SEQ ID NO: 15) by PCR. For this PCR, the reverse primer contained the target sequence for either RAG1 or I-SceI and a NheI restriction site and the forward primer contained a SalI restriction enzyme site. After amplification of the WILD TYPE micro-dystrophin/V5 plasmid with the previous primers and cloning in the pDrive vector (Qiagen), the fragment SalI/NheI (1300 bp) containing the target sequence for one of the specific meganucleases was sequenced and cloned in the WILD TYPE micro-dystrophin/V5 plasmid also cut with SalI/NheI (removing the original fragment and replacing it by the mutated fragment) and making final constructs MUTATED micro-dystrophin/V5 containing the RAG1 or I-SceI target (see FIG. 2B). These mutated micro-dystrophin/V5 constructs resulted in an out of frame micro-dystrophin/V5 expression and create stop codons which made it impossible to express the V5 epitope peptide as shown in FIG. 1B.

293FT Cells Culture

For the present studies, the inventors used 293FT cells, purchased from Invitrogen, as recipient cells for co-transfection of mutated dog micro-dystrophin/V5 constructs with one the MGN plasmids. The transfections were made with lipofectamine 2000 (Invitrogen) since these cells are easily transfected with this reagent as indicated by the manufacturer. Moreover, these cells are weakly attached on the bottom of plates in culture avoiding the use of trypsin to detach the cells making the possibility to easily divide the cells in two parts for analysis of proteins and of DNA from the same well of a 6 well plate. The 293FT cells were grown in DMEM high glucose, 10% bovine serum, 4 mM glutamine and 1× penicillin/streptomycin. All of these components were purchased from Wisent, Montreal, Canada. To confirm the occurrence of NHEJ in the endogenous dystrophin gene of 293FT cells, 500000 293FT cells were plated per well in a 6 wells plate. The day after, cells were transfected with the lipofectamine 2000 transfection agent. 4 µg of each meganuclease plasmid, namely pCLS2874 (SEQ ID NO: 53), pCLS3387 (SEQ ID NO: 54), pCLS3631 (SEQ ID NO: 55), pCLS3633 (SEQ ID NO: 56), pCLS3326 (SEQ ID NO: 57), and pCLS3330 (SEQ ID NO: 58), were used. 72 hours after transfection, cells were detached from the well and split in two for proteins and genomic DNA extraction.

Episomal Micro-Dystrophin/V5 Gene Repair in 293FT Cells

For the studies of the episomal gene repair, 293FT cells (Invitrogen) in 6-well plates were co-transfected in the presence of lipofectamine 2000 (Invitrogen) with 200 ng or 1200 ng of pLenti6/V5 MUTATED dog micro-dystrophin/V5 containing the RAG1 or I-SceI target. Some cells were co-transfected with the plasmid coding for the meganuclease RAG1 or I-SceI (Cellectis). The transfection with lipofectamine 2000 was done according to the manufacturer protocols (Invitrogen) in which the total final amount of plasmid was 4 mg, completing with specific MGNs RAG1 or I-SceI or in absence of MGNs with pLenti6/V5 EGFP. The transfection efficiency was qualitatively estimated to be near 100% in control wells transfected with a similar sized EGFP plasmid.

Two days after the transfection, the 293FT cells were harvested by simply detaching them by pipetting up and down followed by several washings in phosphate buffer saline (PBS). The cells were then divided into two pools in order to extract the proteins and the genomic DNA separately from the same well. Proteins were analyzed by Western blotting using specific antibodies for the V5 epitope or for the HA tag fused with the meganucleases. The genomic DNA was PCR amplified for the identification of heteroduplex formation with the Surveyor® nuclease and for confirmation that Non-Homologous End Joining (NHEJ) was induced by the meganucleases in the 293FT cells.

Mismatch Selective Endonuclease Assay for Evaluation of Meganuclease-Mediated Gene Disruption The meganucleases (MGNs) RAG1 or I-SceI are able to produce mutations of their specific target located in the mutated dog micro-dystrophin/V5. These mutations were evaluated by PCR amplification of their specific target present in the mutated micro-dystrophin/V5 constructs described above. DNA was extracted from 293FT cells transfected with the target mutated micro-dystrophin/V5 with and without co-transfection with one of the MGNs. Amplicons from cells transfected with the MGNs were mixed in equal amount with amplicons obtained from cells transfected with the target without a MGN. The amplicon mix was then denaturated and re-annealed allowing modified target amplicon and non-modified target amplicon to re-anneal together to create heteroduplexes. The re-annealed PCR products were then digested with the Surveyor® nuclease (Transgenomic, Omaha, Nebr.) that preferentially cuts DNA at sites of duplex distortions. Briefly, PCR (50 ml reactions) was done with the Phusion™ High-Fidelity DNA Polymerase (New England Biolabs) from 100 ng of genomic DNA extracted from 293FT in which the mutated micro-dystrophin/V5 and one of the MGNs were present and a control (mutated micro-dystrophin/V5 alone without a MGN). The amplification reaction with Phusion™ polymerase was performed as follows: 1 cycle: 98° C.—1 min; 35 cycles: 98° C.—10 sec, 60° C.—30 sec, 72° C.—30 sec; 1 cycle: 72° C.—10 min) using the following primers: forward 5'-gacagttatcaaacagctttggaag-3' SEQ ID NO: 16) (pos 1027-1051 dystrophin cDNA) and reverse 5'-gtaatctgtgggtgtcttgtaaaaga-3' SEQ ID NO: 17) (pos 1684-1673 dystrophin cDNA).

The PCR products (amplicons) were extracted after electrophoresis on agarose gel 1.4% and purified with a Qiaquick gel extraction kit (Qiagen). A mix of equal amount of two PCR products generated from genomic DNA extracted from 293FT cells was done in 9 µl containing annealing buffer 1× (10 mM Tris-HCl pH 8.3, 50 mM KCl, 1.5 mM MgCl$_2$). Heteroduplexe formation was realized with a block heating bath set at 95° C. for 5 min and the block was then removed from bath and cooled by itself to <30° C. After re-annealing, 0.5 ml of the Surveyor® Enhancer 5 and 0.5 ml Surveyor® nuclease (Transgenomic) were added to a total volume of 10 ml. The reaction was incubated at 42° C. for 20 min to digest heteroduplexes and the cleaved products were analyzed on a 2% agarose gel containing TBE 1× and ethidium bromide (1 mg/ml). To estimate approximately the expected fragment size generated by the Surveyor® nuclease, the Applicants mixed amplicons of the wild type of micro-dystrophin/V5 (without target) with the mutated micro-dystrophin/V5 produced from genomic DNA extracted of the 293FT cells.

Protein Extraction and Western Blot Analysis of the Micro-Dystrophin/V5 and Meganucleases from 293FT Cells Protein extraction from 293FT cells was performed according to the previously published protocol [38]. The presence of the micro-dystrophin/V5 and MGN RAG1 or MGN I-SceI was confirmed by Western blot of proteins extracted from the 293FT cells. Usually, an aliquot of 20 µg of proteins extracted from 293FT cells treated in different conditions was loaded in each lane and electrophoresed in 8% acrylamide gel (SDS-PAGE). The proteins were then electrotransferred onto a 0.45 mm nitrocellulose membrane (Bio-Rad, CA, USA) and cut in two sections: the upper part (proteins range over 85 kDa) for the detection of the micro-dystrophin/V5 and the lower part for the detection of HA tag fused with the MGN RAG1 or the I-SceI (proteins range under 85 kDa). Membrane sections were blocked in 5% (w/v) non-fat dry milk (Blotto) resuspended in PBS containing 0.05% Tween-20 for 1 hour and then incubated overnight at 4° C. in presence of a primary antibody, either a monoclonal antibody directed against the V5 epitope (Invitrogen) diluted 1/5000 to detect the micro-dystrophin/V5 or a goat polyclonal antibody against the HA-tag (GenScript, Piscataway, N.J.) diluted 0.5 mg/ml to detect the HA-MGNs. After incubation of the membrane sections, three consecutive washings were done for 10 min in PBS-Tween 0.05% and then membranes were incubated for 1 hour with a specific secondary antibody for V5 flag, which was a rabbit anti-goat coupled to peroxidase (1/10000) or a rabbit anti-goat coupled to peroxidase (1/10000) for the HA tag both in PBS-Tween 0.05% containing 5% Blotto. After incubation of membrane sections with their specific secondary antibody, three washings (10 min each) were done in PBS-Tween. The membranes were then treated for 1 min with the enhanced chemiluminescent substrate (Perkin-Elmer, Woodbridge, Canada) and exposed to a Bio-Max film (Perkin-Elmer).

Protein Extraction and Western Blot Analysis to Confirm the Occurrence of NHEJ in the Endogenous Dystrophin Gene of 293FT Cells Cells were washed twice in HBSS and were lysed in 200 µl of lysis buffer containing 20 mM Tris PH7.5, 1 mM DTT, 1 mM PMSF and 1% SDS. Protein samples were prepared as follows: In microtubes containing the 200 µl of lysed cells, 600 µl of methanol, 200 µl of chloroform, 500 µl of water were added. After each liquid addition, microtubes were vortexed. Microtubes were centrifuged one minute at 14800 RPM and the solid white phase at the interphase was recuperated and washed with 300 µl of methanol. White pellet were lyophilized. Pellets were boiled in 40 µl of loading buffer containing Tris pH6.8 0.25M, 10% SDS, 7.5% glycerol and 0.5% beta-mercaptoethanol. 10 µl were loaded on 10% gel SDS-page electrophoresis. After protein electrotransfert on nitrocellulose membrane, the membrane was blocked in PBS-Tween (0.05%) containing 5% milk for one hour. The membrane was incubated overnight at 4° C. with a C-terminal 6-His tagged polyclonal anti-1-CreI rabbit antibody (1/20000). The membrane was washed 3 times 10 minutes in PBS-Tween (0.05%). After, the membrane was incubated one hour with a goat anti-rabbit-HRP antibody (1/2000), washed 3 times in PBS-Tween (0.05%) and revealed with a chemiluminescence kit.

Gene Sequencing of Mutated Episomal DNA to Confirm the Occurrence of NHEJ in 293FT Cells Genomic DNA was extracted from 293FT cells (in a six well plate) co-transfected with 1200 ng of the mutated micro-dystrophin/V5 plasmid containing the RAG1 target and 2.8 mg of the MGN RAG1 plasmid. A protocol to extract genomic DNA based on the use of proteinase K, RNase, phenol/chloroform procedure was used [39]. The plasmid coding for the dog micro-dystrophin/V5 including the RAG1 target was co-precipitated with the genomic DNA since it was amplified with Phusion™ DNA polymerase using specific primers to dog dystrophin (SEQ ID NO: 16 and 17). This amplicon was then treated with TAQ DNA polymerase (New England Biotechnology) to add A at 3' end of the PCR fragments to permit direct cloning in pDrive cloning vector (Qiagen) with the Qiagen PCR cloning kit. Following transformation of ligation products in competent bacteria DH5a, several clones were picked randomly to prepare plasmids (mini-prep) and sequenced with the T7 primer. A total of 15 clones were sequenced and six of them showed deletion/insertion (indel) due to NHEJ.

Gene Sequencing to Confirm the Occurrence of NHEJ in the Endogenous Dystrophin Gene of 293FT Cells Genomic DNA was first extracted by washing the cells twice in HBSS. Cells were then lysed in 100 µl of lysis buffer containing 0.45M EDTA and 1% sarkosyl. 10 µl of proteinase K (20 mg/ml) were added and incubated at 50° C. for 10 minutes. 400 µl of tris (50 mM pH 8) solution were then added, followed by phenol/chloroform extraction. DNA were ethanol precipitated and pellets were resuspended in water.

100 ng of genomic DNA was then amplified for only 5 cycles with the PCR parameters as follow: one step at 98° C. for 1 min and 30 cycles of 98° C., 30 sec, 60° C., 30 sec, 72° C. 30 sec.

Primers sequences are as follow:

```
DMD 21
                                    (SEQ ID NO: 38)
FWD: TCTTGCAGCCTAAAGGAACAAA (SEQ ID NO: 39)
REV: TCCTCTCGCTTTCTCTCATCTG

DMD 31
                                    (SEQ ID NO: 40)
FWD: GAACAGGTGGTATTACTAGCCA (SEQ ID NO: 41)
REV: GGTTGCAGTGAGCTGAGATCAT

DMD 33
                                    (SEQ ID NO: 42)
FWD: GCAGAGCTAGAGAAGAATGAGAAA (SEQ ID NO: 43)
REV: TTTGTTATTGGTTGAGGTTTGCTG
```

Nested PCR were made for each meganuclease target with primers containing sequences required for Illumina procedure and tag for amplicons identification. For the nested PCR, 5 µl of the first PCR step were used that were treated as follow: 98° C. 1 min, 98° C. 5 sec, 55° C. 10 sec, 72° C. 10 sec for 5 cycles and others 28 cycles as 98° C. 5 sec, 65° C. 10 sec, 72° C. 10 sec. Amplicons were agarose gel purified with the Qiagen gel extraction kit following the manufacturer's instructions. All amplicons from different DMD targets were assayed with nanodrop and were pooled in the same proportion (final DNA concentration is 10 ng/µl) before deep sequencing analysis.

Animals

Rag-Mdx mice were from the Laval University colony. All the experiments made on these animals were approved by the Animal Protection Committee of Laval University.

Electroporation

40 µg total of plasmids, i.e., 20 µg of the target plasmid and 20 µg of the meganuclease or 30 µg of the target plasmid and 10 µg of the meganuclease (either I-SceI or Rag1) were injected to a final volume of 40 µL in the mouse muscle for electroporation. As a negative control, the target plasmid (20 µg) was injected alone and as positive control, 40 µg of the original micro-dystrophin/V5 plasmid (without target) was injected alone. A single longitudinal injection was made into the Tibialis anterior (Ta) and the "Electrode Electrolyte" cream (Teca Corporation, Pleasantville, N.Y.) was applied on the skin to induce the spreading of the electric current between two metal plaques. The parameters were: 10 pulses of 200 V/cm, duration of 25 ms and delay of 300 ms. The electrotransfered muscles were harvested two weeks after the experiment and were rapidly frozen in liquid nitrogen. Serial 12 µm cryostat sections were prepared throughout the entire muscle.

Immunohistochemical Detection of Micro-Dystrophin/V5 in Mouse Tibialis Anterior Muscle Immunohistological analyses were performed with mouse anti-V5 antibody (1:200, Invitrogen) followed by incubation with a biotinylated anti-mouse antibody (1:300, Dako, Mississauga, Canada) and Streptavidin-Cy3 (1:300, Sigma). Afterwards, the sections were mounted in PBS-Glycerol (1:1). The presence of GFP proteins and the immunohistological staining were observed under fluorescence using an Axiophot microscope (Zeiss, Oberkochen, Germany).

EXAMPLE 2

Results

Meganucleases RAG1, I-SceI Design and their Specific Target within the Dog Micro-Dystrophin/V5

As shown in FIG. 1A, the meganucleases (MGNs) RAG1 and I-SceI were under control of elongation EF1 alpha gene promoter fused to exon1 and intron1 of EF1 gene. The MGN cDNA were followed at their 5' end by nucleotides coding for the HA-tag and for a nuclear localization signal (NLS). The expected molecular weight (MW) for MGN RAG1 and I-SceI with the HA-tag and the NLS were respectively 42.3 kDa and 31.24 kDa. The transcription unit of MGN RAG1 and I-SceI were contained respectively in a plasmid size of 5.51 kb and 5.15 kb.

A sequence of 29 nucleotides including the specific target (24 nucleotides) for RAG1 or I-SceI MGN was inserted within the dog micro-dystrophin/V5 cDNA near of the NheI site as described in FIG. 1B. The insertion of this sequence in the micro-dystrophin/V5 cDNA changed the reading frame of the part of the dystrophin gene located after the inserted sequence; this resulted in the presence of premature stop codons. The wild type and the mutated micro-dystrophin/V5 were under a CMV promoter and introduced in a plasmid pLenti6/V5 containing a puromycin gene resistance. A wild type dog micro-dystrophin/V5 (FIG. 1B) without a MGN target insertion was used as control to evaluate the efficiency of micro-dystrophin expression in the Applicants analysis system.

Expression of Micro-Dystrophin/V5 Following Co-Transfection of an Appropriate Meganuclease Plasmid with the Corresponding Micro-Dystrophin-V5 Target Plasmid The inventors developed a plasmid based gene repair assay involving the two components (a plasmid target and a meganuclease plasmid) described in FIGS. 1 A and B, to verify the capacity of a meganuclease to modify the reading frame of the mutated micro-dystrophin/V5 containing specific target for RAG1 or I-SceI leading to some expression of the mutated micro-dystrophin/V5. The micro-dystrophin/V5 containing a MGN target (mutated dystrophin) was co-transfected with the corresponding MGN plasmid in 293FT cells and 48 hours after transfection, the total proteins were extracted from the cells to be analyzed by Western blot using an anti-V5 antibody to detect the expression of micro-dystrophin/V5 and a goat antibody against the HA-tag to detect the expression of the meganuclease protein. As expected, the presence of micro-dystrophin/V5 (MW of 175 kDa) and of the MGN RAG1 (FIG. 2A, lanes 1-4)) or of the MGN I-SceI (FIG. 2B, lanes 1-4) were detected in the same protein extracts. In both experiments in which MGN RAG1 or I-SceI were co-transfected with micro-dystrophin/V5 containing their specific target, western blot analysis for the presence of HA-tag showed the expression of the MGN protein with the expected MW of 42 kDa for MGN RAG1 and 31 kDa for MGN I-SceI (FIGS. 2A and B). As expected, micro-dystrophin/V5 was more strongly expressed when the MGN co-transfection was done with a higher amount of target plasmid (1200 ng) (FIGS. 2A and B, lanes 3 and 4) than with a lower amount of target plasmid (200 ng) (FIGS. 2A and B, lanes 1 and 2). However, a reduced amount of MGN had no effect on the micro-dystrophin/V5 expression (lanes 1 and 2 vs lanes 3 and 4 in FIGS. 2A and B). As shown in FIGS. 2 A and B, lanes 5, no micro-dystrophin/V5 expression was detected in the cells co-transfected with a EGFP plasmid (instead of a MGN plasmid) and the plasmid containing micro-dystrophin/V5 inserted with a target for RAG1 or for I-SceI. From this last observation, co-transfection with a EGFP plasmid resulted in high transfection efficiency as 100% 293FT cells were fluorescent green (results not shown). This indicates that the co-transfection did not prevent us from obtaining good transfection efficiency in these cells. Finally, the transfection in 293FT cells of 2 different amounts of the Wild type micro-dystrophin/V5 protein plasmid (positive control without a MGN target) produced different expression levels in function of the amount of plasmid used (FIG. 2A, lanes 5 and 6 and FIG. 2B, lanes 6 and 7). Interestingly by Western blot analysis, the expression levels observed for the corrected mutated dystrophin in lanes 3 and 4 (FIGS. 2A and B) were a substantial proportion of the positive controls in lanes 6 and 7 (FIGS. 2A and B) suggesting that the correction of the micro-dystrophin/V5 gene was substantial.

Mutation Detection by Surveyor® Nuclease of Episomal Plasmid Mutated Micro-Dystrophin/V5 in 293FT Cells Treated with MGNs RAG1 and I-SceI The inventors then tried to confirm that the expression of the micro-dystrophin/V5 following co-transfection of the target plasmid and of a MGN plasmid was really due to the modification by the MGN endonuclease activity of the target sequence inserted in the mutated micro-dystrophin/V5. A DSB induced by a MGN can be repaired by an error-prone non-homologous end joining (NHEJ) and the resulting DNA often contains small insertions or deletions ("indel" mutations) near of the DSB site. To confirm the presence of indels in the episomal targeted plasmids, the genomic DNA of the transfected cells was extracted (containing also the episomal target plasmid) and amplified by PCR using primers located within the micro-dystrophin/V5 gene before and after the meganuclease target nucleotide sequence, as described in materials and methods section. In vitro, the indel mutations can be detected by treatment of amplified DNA fragments (amplicons) with mismatch-sensitive Surveyor® enuclease according to the protocol described in the method section. Amplicons treated with Surveyor® nuclease were analyzed by agarose gel electrophoresis. Only one band of 681 bp (lane 1) and 657 bp (FIGS. 3 A and B, lane 4) were observed in the cells transfected respectively only with the target plasmid or only with the wild type plasmid, indicating that the Surveyor® nuclease did not cut these amplicons because there were no heteroduplex. However, two fragments of ~400 and ~320 bp (FIG. 3A, lanes 2 and 3) for RAG1 or I-SceI (FIG. 3B, lanes 2 and 3) were generated when the Surveyor® nuclease was used to cleave amplicons obtained from the cells transfected with the target plasmid with the right meganuclease mixed with amplicons derived from cells transfected with the target plasmid alone (without MGNs). This indicated that the Surveyor® nuclease cut some amplicons because their 2 nucleotide strands were different due to the presence of some indels induced by the meganucleases. As positive control, a mixing of equal amount of amplicons from wild type plasmid and mutated plasmid without MGN treatment was digested with the Surveyor® nuclease giving a similar digestion profile showing two fragments of ~370 and ~300 bp (FIGS. 3A and B, lane 5). The slight differences in the size of the fragments observed in lanes 1, 2 and 3 in comparison to lanes 4 and 5 as shown in FIGS. 3A and B are the results of the presence of the insertion target (FIG. 3C, black box) within the mutated micro-dystrophin. All the observations done from 293FT cells co-transfected with the target plasmid and the right MGN indicate that both MGNs, RAG1 and I-SceI, induced sequence changes in the target of mutated dystrophin, leading to the restoration of the dystrophin expression.

Sequencing of the Targeted Area Confirmed the Presence of Indels and the Restoration of the Reading Frame for MGN RAG1

The Applicants next wanted to confirm not only the presence of indels but also the presence of indels that restored the normal reading frame of the micro-dystrophin-Rag1/V5 plasmid. The preparation of genomic DNA from 293FT cells co-transfected with 1200 ng of target micro-dystrophin-Rag1/V5 and 2.8 mg of MGN RAG1 has been described in materials and methods section. The amplicons generated by PCR amplification of this DNA were cloned in DH5a and sequenced. As presented in the FIG. 4B, indels were detected in 6 of the 15 clones randomly picked. Moreover, four of these 6 clones had indels that restored the reading frame (amino acids sequence (FIG. 4A) of the micro-dystrophin-Rag1 target/V5 transgene. This demonstrates that NHEJ was able to efficiently restore the expression of an out of frame-mutated dystrophin within 293FT cells.

Restoration of Micro-Dystrophin Reading Frame in Muscle Fibers

Figure 5E:
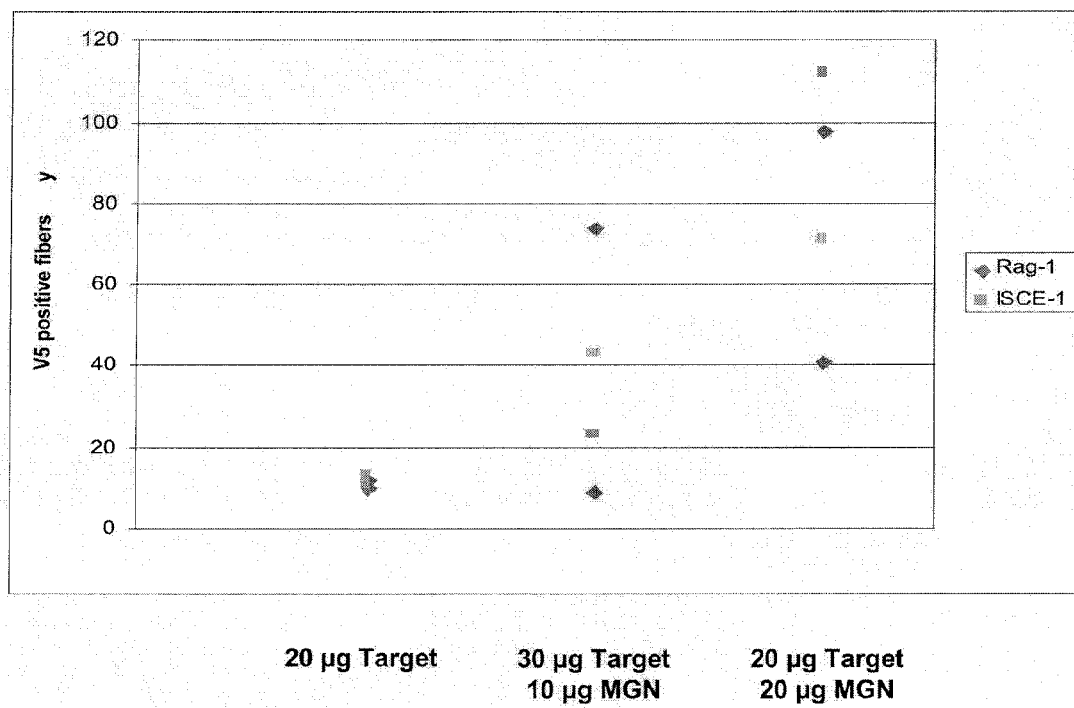

All of the previous experiments have been done in 293FT cells because they are easy to transfect. However, for an eventual clinical application, it is the dystrophin gene located in muscle fibers that will have to be targeted. Will meganuclease induce indels in muscle fibers? To answer this question, the Applicants electroporated the micro-dystrophin-/V5 plasmid with or without an insertion with or without an appropriate meganuclease plasmid in the Tibialis anterior (TA)

muscles of Rag-mdx mice. As negative control, the Applicants have only electroporated the target plasmid with an inserted sequence that changed the reading frame. Two weeks later, the mice were sacrificed and the TA muscles were prepared for immunohistochemistry analysis of the micro-dystrophin/V5 expression as described in materials and methods section. The expression of the V5 flag was detected in the membrane of rare weakly labeled muscle fibers (FIG. 5A). As a positive control, other muscles were electroporated with the micro-dystrophin/V5 plasmid, not containing any sequence that changed the reading frame. The expression of micro-dystrophin was detected in abundant muscle fibers (FIG. 5B). Finally, muscles were co-electroporated with the micro-dystrophin/V5 plasmid containing the target sequence of either Rag1 or I-SceI and with the plasmid coding for the appropriate meganuclease. FIGS. 5C and D illustrate the expression of the recombinant protein in fibers of muscles co-electroporated respectively with the micro-dystrophin/V5 with a target for Rag1 or I-SceI and with the appropriate meganuclease. These co-electroporations led to the restoration of the normal micro-dystrophin reading frame and thus to its presence in many muscle fibers 5C for Rag1 and FIG. 5D for I-SceI). FIG. 5E summarizes the results obtained with the 2 meganucleases at 2 concentrations. For both MGNs there were more V5 positive fibers when the ratio of MGN plasmid to the targeted plasmid was higher.

This restoration of the normal micro-dystrophin open reading frame and the restoration of functional micro-dystrophin expression is due to mutation of the targeted plasmids as illustrated in FIG. 6. DNA was extracted from the electroporated muscles 15 days after the electroporation and the plasmid region targeted by the meganuclease I-SceI was amplified. The amplicons were then digested with the Surveyor® enzyme. The presence of the two bands at 300 and 370 bp seen in FIG. 6 are due to the presence of some hetero-duplexes that were cut by the Surveyor® enzyme confirming that the I-SceI meganuclease had caused NHEJ in the micro-dystrophin target plasmids.

Restoration of Micro-Dystrophin Reading Frame in Myoblasts Containing an Integrated Micro-Dystrophin Gene with a Target Sequence for Rag1 or I-SceI Lentivirus vectors were made as specified in FIG. 7 legend; said lentivirus vectors contained under a CMV promoter, either a mutated micro-dystrophin/V5 gene with a inserted target sequence for Rag1 (m-dyst/V5$_{Rag1}$) or a mutated micro-dystrophin/V5 gene with a inserted target sequence for I-SceI (m-dyst/V5$_{I-SceI}$). These lentiviruses also contained a puromycin resistance gene under a SV40 promoter. These lentivirus were used to infect human myoblasts. The infected cells were selected with puromycin and allowed to propagate. Some selected myoblasts were than nucleofected with a plasmid coding either for the Rag1 meganuclease or the I-SceI meganuclease. Control myoblasts were not nucleofected with a meganuclease. Three days later DNA was extracted from all myoblasts. The region coding of the micro-dystrophin construct targeted by Rag1 or I-SceI were amplified by PCR with the same primers used in the experiments in 293FT cells/mice. These amplicons were then digested with the Surveyor® enzyme to verify the presence of heterodimers due to insertions or deletions produced by NHEJ following the creation of a DSB by the meganuclease in the genome integrated micro-dystrophin V5 gene. FIG. 7 illustrates the results of the Surveyor® reactions. These results confirm that the meganucleases are able to mutate the micro-dystrophin gene integrated in the cell genome so as to restore function.

Inducement of NHEJ in the Endogenous Dystrophin Gene of 293Ft Cells by Meganucleases Six meganucleases derived from I-CreI and targeting three different introns of dystrophin (two variants for each of the targeted site) were used to demonstrate that meganucleases could induce NHEJ in the endogenous, i.e. chromosomal, dystrophin gene of 293FT cells.

TABLE 1

Meganuclease targets

| Meganuclease name or reference | Target sequence | Position on dystrophin gene |
|---|---|---|
| DMD21 2874 (SEQ ID NO: 44) | GAAACCTCAAGTACCAAATGTAAA | Intron38 |
| DMD21 3387 (SEQ ID NO: 45) | (SEQ ID NO: 50) | nt 993350-993373 |
| DMD31 3631 (SEQ ID NO: 46) | AATGTCTGATGTTCAATGTGTTGA | Intron44 |
| DMD31 3633 (SEQ ID NO: 47) | (SEQ ID NO: 51) | nt1125314-1125337 |
| DMD33 3326 (SEQ ID NO: 48) | AAATCCTGCCTTAAAGTATCTCAT | Intron42 |
| DMD33 3330 (SEQ ID NO: 49) | (SEQ ID NO: 52) | nt1031834-10931857 |

The plasmids coding for these meganucleases, namely pCLS2874 (SEQ ID NO: 53), pCLS3387 (SEQ ID NO: 54), pCLS3631 (SEQ ID NO: 55), pCLS3633 (SEQ ID NO: 56), pCLS3326 (SEQ ID NO: 57), and pCLS3330 (SEQ ID NO: 58), were transfected in 293FT human cells. The expression of the meganucleases was detected by Western blot using a C-terminal 6-His tagged polyclonal rabbit antibody against the I-CreI meganuclease. This antibody reacts with the constant part of the meganucleases and thus reacts with DMD21, DMD31 and DMD33 meganucleases. All three meganucleases proteins were detected by Western blot (see FIG. 8: DMD21 (lanes 2874 and 3387), DMD31 (lanes 3631 and 3633), DMD33 (lanes 3326 and 3330)).

The presence of mutations was detected by using the Deep sequencing technique: INDELs were detected with all six meganucleases targeting the endogenous dystrophin gene in 293FT cells (Table 2). Between 30,000 and 50,000 amplicons were sequenced for each meganuclease. The frequency of INDELs varied between 0.14 to 1.60% depending on the MGN. A meganuclease targeting Rag was taken as a control and mutates 6.40% of the target gene.

TABLE 2

Percentage of deletion or insertion obtained by meganucleases

| | DMD21 | | | DMD31 | | | DMD33 | | | | |
|---|---|---|---|---|---|---|---|---|---|---|---|
| | Ctrl | 2874 | 3387 | Ctrl | 3631 | 3633 | Ctrl | 3326 | 3330 | Ctrl | RAG |
| Deletion | 0.03% | 1.30% | 1% | 0.00% | 1.60% | 1% | 0.02% | 0.20% | 0.1% | 0.00% | 6.40% |
| Insertion | 0.00% | 0.11% | 0.015% | 0% | 0.19% | 0.09% | 0.02% | 0.14% | 0.04% | 0.00% | 0.15% |

These results thus demonstrate that meganucleases can mutate the real dystrophin gene in its real location on the X chromosome.

REFERENCES

1. Trimarco, A, Torella, A, Piluso, G, Maria Ventriglia, V, Politano, L, and Nigro, V (2008). Log-PCR: a new tool for immediate and cost-effective diagnosis of up to 85% of dystrophin gene mutations. *Clin Chem* 54: 973-981.
2. Hoffman, E P, Brown, R H, Jr., and Kunkel, L M (1987). Dystrophin: the protein product of the Duchenne muscular dystrophy locus. *Cell* 51: 919-928.
3. England, S B, et al. (1990). Very mild muscular dystrophy associated with the deletion of 46% of dystrophin. *Nature* 343: 180-182.
4. Odom, G L, Gregorevic, P, Allen, J M, Finn, E, and Chamberlain, J S (2008). Microutrophin delivery through rAAV6 increases lifespan and improves muscle function in dystrophic dystrophin/utrophin-deficient mice. *Mol Ther* 16: 1539-1545.
5. Wang, Z, et al. (2007). Sustained AAV-mediated dystrophin expression in a canine model of Duchenne muscular dystrophy with a brief course of immunosuppression. *Mol Ther* 15: 1160-1166.
6. Lai, Y, Yue, Y, Liu, M, and Duan, D (2006). Synthetic intron improves transduction efficiency of trans-splicing adeno-associated viral vectors. *Hum Gene Ther* 17: 1036-1042.
7. Liu, M, Yue, Y, Harper, S Q, Grange, R W, Chamberlain, J S, and Duan, D (2005). Adeno-associated virus-mediated microdystrophin expression protects young mdx muscle from contraction-induced injury. *Mol Ther* 11: 245-256.
8. Ohshima, S, et al. (2009). Transduction efficiency and immune response associated with the administration of AAV8 vector into dog skeletal muscle. *Mol Ther* 17: 73-80.
9. Harper, S Q, et al. (2002). Modular flexibility of dystrophin: Implications for gene therapy of Duchenne muscular dystrophy. *Nat Med* 8: 253-261.
10. Skuk, D, et al. (2007). First test of a "high-density injection" protocol for myogenic cell transplantation throughout large volumes of muscles in a Duchenne muscular dystrophy patient: eighteen months follow-up. *Neuromuscul Disord* 17: 38-46.
11. Skuk, D, et al. (2006). Dystrophin expression in muscles of duchenne muscular dystrophy patients after high-density injections of normal myogenic cells. *J Neuropathol Exp Neurol* 65: 371-386.
12. Sampaolesi, M, et al. (2006). Mesoangioblast stem cells ameliorate muscle function in dystrophic dogs. *Nature* 444: 574-579.
13. Ikemoto, M, et al. (2007). Autologous Transplantation of SM/C-2.6(+) Satellite Cells Transduced with Micro-dystrophin CS1 cDNA by Lentiviral Vector into mdx Mice. *Mol Ther.*
14. Deasy, B M, Jankowski, R J, and Huard, J (2001). Muscle-derived stem cells: characterization and potential for cell-mediated therapy. *Blood Cells Mol Dis* 27: 924-933.
15. Peault, B, et al. (2007). Stem and progenitor cells in skeletal muscle development, maintenance, and therapy. *Mol Ther* 15: 867-877.
16. Wilton, S (2007). PTC124, nonsense mutations and Duchenne muscular dystrophy. *Neuromuscul Disord* 17: 719-720.
17. Welch, E M, et al. (2007). PTC124 targets genetic disorders caused by nonsense mutations. *Nature* 447: 87-91.
18. Yokota, T, Duddy, W, and Partridge, T (2007). Optimizing exon skipping therapies for DMD. *Acta Myol* 26: 179-184.
19. Jearawiriyapaisarn, N, et al. (2008). Sustained dystrophin expression induced by peptide-conjugated morpholino oligomers in the muscles of mdx mice. *Mol Ther* 16: 1624-1629.
20. Williams, J H, Schray, R C, Sirsi, S R, and Lutz, G J (2008). Nanopolymers improve delivery of exon skipping oligonucleotides and concomitant dystrophin expression in skeletal muscle of mdx mice. *BMC Biotechnol* 8: 35.
21. Adams, A M, Harding, P L, Iversen, P L, Coleman, C, Fletcher, S, and Wilton, S D (2007). Antisense oligonucleotide induced exon skipping and the dystrophin gene transcript: cocktails and chemistries. *BMC Mol Biol* 8: 57.
22. Urnov, F D, et al. (2005). Highly efficient endogenous human gene correction using designed zinc-finger nucleases. *Nature* 435: 646-651.
23. Lombardo, A, et al. (2007). Gene editing in human stem cells using zinc finger nucleases and integrase-defective lentiviral vector delivery. *Nature biotechnology* 25: 1298-1306.
24. Grizot, S, et al. (2009). Efficient targeting of a SCID gene by an engineered single-chain homing endonuclease. *Nucleic Acids Res.*
25. Stoddard, B L (2005). Homing endonuclease structure and function. *Q Rev Biophys* 38: 49-95.
26. Rouet, P, Smih, F, and Jasin, M (1994). Introduction of double-strand breaks into the genome of mouse cells by expression of a rare-cutting endonuclease. *Mol Cell Biol* 14: 8096-8106.
27. Choulika, A, Perrin, A, Dujon, B, and Nicolas, J F (1995). Induction of homologous recombination in mammalian chromosomes by using the I-SceI system of *Saccharomyces cerevisiae*. *Mol Cell Biol* 15: 1968-1973.
28. Paques, F, and Duchateau, P (2007). Meganucleases and DNA double-strand break-induced recombination: perspectives for gene therapy. *Curr Gene Ther* 7: 49-66.
29. Boothroyd, C E, et al. (2009). A yeast-endonuclease-generated DNA break induces antigenic switching in *Trypanosoma brucei*. *Nature* 459: 278-281.
30. Paques, F, and Haber, J E (1999). Multiple pathways of recombination induced by double-strand breaks in *Saccharomyces cerevisiae*. *Microbiol Mol Biol Rev* 63: 349-404.

31. Arnould, S, et al. (2006). Engineering of large numbers of highly specific homing endonucleases that induce recombination on novel DNA targets. *Journal of molecular biology* 355: 443-458.
32. Ashworth, J, et al. (2006). Computational redesign of endonuclease DNA binding and cleavage specificity. *Nature* 441: 656-659.
33. Doyon, J B, Pattanayak, V, Meyer, C B, and Liu, D R (2006). Directed evolution and substrate specificity profile of homing endonuclease I-SceI. *Journal of the American Chemical Society* 128: 2477-2484.
34. Smith, J, et al. (2006). A combinatorial approach to create artificial homing endonucleases cleaving chosen sequences. *Nucleic Acids Res* 34: e149.
35. Arnould, S, et al. (2007). Engineered I-CreI derivatives cleaving sequences from the human XPC gene can induce highly efficient gene correction in mammalian cells. *Journal of molecular biology* 371: 49-65.
36. Redondo, P, et al. (2008). Molecular basis of xeroderma pigmentosum group C DNA recognition by engineered meganucleases. *Nature* 456: 107-111.
37. Wang, B, et al. (2008). A canine minidystrophin is functional and therapeutic in mdx mice. *Gene Ther* 15: 1099-1106.
38. Chapdelaine, P, Vignola, K, and Fortier, M A (2001). Protein estimation directly from SDS-PAGE loading buffer for standardization of samples from cell lysates or tissue homogenates before Western blot analysis. *Biotechniques* 31: 478, 480, 482.
39. Chapdelaine, P, Delahaye, S, Gauthier, E, Tremblay, R R, and Dube, J Y (1993). A one-hour procedure for the preparation of genomic DNA from frozen tissues. *Biotechniques* 14: 163-164.
40. Chauhan, A, Tikoo, A, Kapur, A K, and Singh, M (2007). The taming of the cell penetrating domain of the HIV Tat: myths and realities. *J Control Release* 117: 148-162.
41. Schwarze, S R, Ho, A, Vocero-Akbani, A, and Dowdy, S F (1999). In vivo protein transduction: delivery of a biologically active protein into the mouse [see comments]. *Science* 285: 1569-1572.
42. Dietz, G P, and Bahr, M (2004). Delivery of bioactive molecules into the cell: the Trojan horse approach. *Mol Cell Neurosci* 27: 85-131.
43. Zhao, Y, Lou, D, Burkett, J, and Kohler, H (2001). Chemical engineering of cell penetrating antibodies. *J Immunol Methods* 254: 137-145.
44. Kokryakov, V N, et al. (1993). Protegrins: leukocyte antimicrobial peptides that combine features of corticostatic defensins and tachyplesins. *FEBS Lett* 327: 231-236.
45. Jans, D A (1994). Nuclear signaling pathways for polypeptide ligands and their membrane receptors? *Faseb J* 8: 841-847.
46. Chang, M, Zhang, L, Tam, J P, and Sanders-Bush, E (2000). Dissecting G protein-coupled receptor signaling pathways with membrane-permeable blocking peptides. Endogenous 5-HT(2C) receptors in choroid plexus epithelial cells. *J Biol Chem* 275: 7021-7029.
47. Lavigne, M D, Yates, L, Coxhead, P, and Gorecki, D C (2008). Nuclear-targeted chimeric vector enhancing non-viral gene transfer into skeletal muscle of Fabry mice in vivo. *Faseb J* 22: 2097-2107.
48. Caron, N J, et al. (2001). Intracellular delivery of a Tat-eGFP fusion protein into muscle cells. *Mol Ther* 3: 310-318.
49. Xiong, F, et al. (2007). Enhanced effect of microdystrophin gene transfection by HSV-VP22 mediated intercellular protein transport. *BMC Neurosci* 8: 50.
50. Sonnemann, K J, Heun-Johnson, H, Turner, A J, Baltgalvis, K A, Lowe, D A, and Ervasti, J M (2009). Functional substitution by TAT-utrophin in dystrophin-deficient mice. *PLoS Med* 6: e1000083.
51. Kinoshita, I, Vilquin, J T, Asselin, I, Chamberlain, J, and Tremblay, J P (1998). Transplantation of myoblasts from a transgenic mouse overexpressing dystrophin produced only a relatively small increase of dystrophin-positive membrane. *Muscle Nerve* 21: 91-103.
52. Cathomen, T, and Joung, J K (2008). Zinc-finger nucleases: the next generation emerges. *Mol Ther* 16: 1200-1207.
53. Bock, H H, Herz, J, and May, P (2007). Conditional animal models for the study of lipid metabolism and lipid disorders. *Handb Exp Pharmacol*: 407-439.
54. Spillmann, L (2006). From perceptive fields to Gestalt. *Prog Brain Res* 155: 67-92.
55. May, P, Herz, J, and Bock, H H (2005). Molecular mechanisms of lipoprotein receptor signalling. *Cell Mol Life Sci* 62: 2325-2338.
56. Durai, S, Mani, M, Kandavelou, K, Wu, J, Porteus, M H, and Chandrasegaran, S (2005). Zinc finger nucleases: custom-designed molecular scissors for genome engineering of plant and mammalian cells. *Nucleic Acids Res* 33: 5978-5990.

The invention claimed is:

1. A method of cleaving a human dystrophin gene comprising administering to an isolated cell comprising a human dystrophin gene at least one meganuclease polypeptide, which recognizes and cleaves a target site in the human dystrophin gene, wherein said meganuclease polypeptide comprises an amino acid sequence selected from the group consisting of SEQ ID NOs: 13, 18, and 44-49.

2. The method of claim 1, wherein said meganuclease polypeptides or a set thereof, which each recognize and cleave a different target site in the human dystrophin gene, is administered to the isolated cell.

3. The method of claim 1, wherein said target site is comprised in the nucleotide sequence of SEQ ID NO: 50.

4. The method of claim 1, wherein said target site is comprised in the nucleotide sequence of SEQ ID NO: 51.

5. The method of claim 1, wherein said target site is comprised in the nucleotide sequence of SEQ ID NO: 52.

6. The method of claim 1, wherein said meganuclease oak/peptide further comprises a protein transduction domain.

7. The method of claim 6, wherein the protein transduction domain comprises the amino acid sequence set forth in SEQ ID NO: 12.

8. The method of claim 1, wherein said meganuclease polypeptide is encoded by at least one purified nucleic acid molecule.

* * * * *

SEQUENCE LISTING

```
<160> NUMBER OF SEQ ID NOS: 81

<210> SEQ ID NO 1
<211> LENGTH: 31
<212> TYPE: DNA
<213> ORGANISM: Homo sapiens

<400> SEQUENCE: 1
aagttaacaa aatgtacaag gaccgacaag g                              31

<210> SEQ ID NO 2
<211> LENGTH: 51
<212> TYPE: DNA
<213> ORGANISM: Homo sapiens

<400> SEQUENCE: 2
agggtgaagc tacaggaagc tctctcccag cttgatttcc aatgggaaaa a        51
```

<210> SEQ ID NO 3
<211> LENGTH: 84
<212> TYPE: DNA
<213> ORGANISM: Homo sapiens

<400> SEQUENCE: 3
tggctaacag aagctgaaca gtttctcaga aagacacaaa ttcctgagaa ttgggaacat     60
gctaaataca aatggtatct taag                                           84

<210> SEQ ID NO 4
<211> LENGTH: 53
<212> TYPE: DNA
<213> ORGANISM: Homo sapiens

<400> SEQUENCE: 4
gaactccagg atggcattgg gcagcggcaa actgttgtca gaacattgaa tgc            53

<210> SEQ ID NO 5
<211> LENGTH: 67
<212> TYPE: DNA
<213> ORGANISM: Homo sapiens

<400> SEQUENCE: 5
aactggggaa gaaataattc agcaatcctc aaaaacagat gccagtattc tacaggaaaa     60
attggga                                                              67

<210> SEQ ID NO 6
<211> LENGTH: 54
<212> TYPE: DNA
<213> ORGANISM: Homo sapiens

<400> SEQUENCE: 6
cctgaatctg cggtggcagg aggtctgcaa acagctgtca gacagaaaaa agag           54

<210> SEQ ID NO 7
<211> LENGTH: 53
<212> TYPE: DNA
<213> ORGANISM: Homo sapiens

<400> SEQUENCE: 7
gtttccagag ctttacctga gaaacaagga gaaattgaag ctcaaataaa aga            53

<210> SEQ ID NO 8
<211> LENGTH: 31
<212> TYPE: DNA
<213> ORGANISM: Homo sapiens

<400> SEQUENCE: 8
ctcctactca gactgttact ctggtgacac a                                    31

<210> SEQ ID NO 9
<211> LENGTH: 19
<212> TYPE: DNA
<213> ORGANISM: Homo sapiens

<400> SEQUENCE: 9
acctgtggtt actaaggaa                                                  19

<210> SEQ ID NO 10
<211> LENGTH: 55
<212> TYPE: DNA

<213> ORGANISM: Homo sapiens

<400> SEQUENCE: 10
gctagaagaa caaaagaata tcttgtcaga atttcaaaga gatttaaatg aattt     55

<210> SEQ ID NO 11
<211> LENGTH: 70
<212> TYPE: DNA
<213> ORGANISM: Homo sapiens

<400> SEQUENCE: 11
ttgaaagaat tcagaatcag tgggatgaag tacaagaaca ccttcagaac cggaggcaac     60
agttgaatga     70

<210> SEQ ID NO 12
<211> LENGTH: 11
<212> TYPE: PRT
<213> ORGANISM: Human immunodeficiency virus

<400> SEQUENCE: 12

Tyr Gly Arg Lys Lys Arg Arg Gln Arg Arg Arg
1               5                   10

<210> SEQ ID NO 13
<211> LENGTH: 260
<212> TYPE: PRT
<213> ORGANISM: Artificial
<220> FEATURE:
<223> OTHER INFORMATION: Modified I-SceI with HA tag and NLS

<400> SEQUENCE: 13

Met Tyr Pro Tyr Asp Val Pro Asp Tyr Ala Gly Phe Ala Ser Ala Pro
1               5                   10                  15

Lys Lys Lys Arg Lys Val Ala Lys Asn Ile Lys Lys Asn Gln Val Met
                20                  25                  30

Asn Leu Gly Pro Asn Ser Lys Leu Leu Lys Glu Tyr Lys Ser Gln Leu
            35                  40                  45

Ile Glu Leu Asn Ile Glu Gln Phe Glu Ala Gly Ile Gly Leu Ile Leu
        50                  55                  60

Gly Asp Ala Tyr Ile Arg Ser Arg Asp Glu Gly Lys Thr Tyr Cys Met
65                  70                  75                  80

Gln Phe Glu Trp Lys Asn Lys Ala Tyr Met Asp His Val Cys Leu Leu
                85                  90                  95

Tyr Asp Gln Trp Val Leu Ser Pro Pro His Lys Glu Arg Val Asn
                100                 105                 110

His Leu Gly Asn Leu Val Ile Thr Trp Gly Ala Gln Thr Phe Lys His
            115                 120                 125

Gln Ala Phe Asn Lys Leu Ala Asn Leu Phe Ile Val Asn Asn Lys Lys
        130                 135                 140

Thr Ile Pro Asn Asn Leu Val Glu Asn Tyr Leu Thr Pro Met Ser Leu
145                 150                 155                 160

Ala Tyr Trp Phe Met Asp Asp Gly Gly Lys Trp Asp Tyr Asn Lys Asn
                165                 170                 175

Ser Thr Asn Lys Ser Ile Val Leu Asn Thr Gln Ser Phe Thr Phe Glu
            180                 185                 190

Glu Val Glu Tyr Leu Val Lys Gly Leu Arg Asn Lys Phe Gln Leu Asn
        195                 200                 205

Cys Tyr Val Lys Ile Asn Lys Asn Lys Pro Ile Ile Tyr Ile Asp Ser

```
                210                 215                 220
Met Ser Tyr Leu Ile Phe Tyr Asn Leu Ile Lys Pro Tyr Leu Ile Pro
225                 230                 235                 240

Gln Met Met Tyr Lys Leu Pro Asn Thr Ile Ser Ser Glu Thr Phe Leu
            245                 250                 255

Lys Ala Ala Asp
        260

<210> SEQ ID NO 14
<211> LENGTH: 25
<212> TYPE: DNA
<213> ORGANISM: Artificial
<220> FEATURE:
<223> OTHER INFORMATION: MGN RAG1 target

<400> SEQUENCE: 14
ttgttctcag gtacctcagc cagca                                              25

<210> SEQ ID NO 15
<211> LENGTH: 24
<212> TYPE: DNA
<213> ORGANISM: Artificial
<220> FEATURE:
<223> OTHER INFORMATION: MGN ISce-1 target

<400> SEQUENCE: 15
cacgctaggg ataacagggt aata                                               24

<210> SEQ ID NO 16
<211> LENGTH: 25
<212> TYPE: DNA
<213> ORGANISM: Artificial
<220> FEATURE:
<223> OTHER INFORMATION: Forward primer

<400> SEQUENCE: 16
gacagttatc aaacagcttt ggaag                                              25

<210> SEQ ID NO 17
<211> LENGTH: 26
<212> TYPE: DNA
<213> ORGANISM: Artificial
<220> FEATURE:
<223> OTHER INFORMATION: Reverse primer

<400> SEQUENCE: 17
gtaatctgtg ggtgtcttgt aaaaga                                             26

<210> SEQ ID NO 18
<211> LENGTH: 376
<212> TYPE: PRT
<213> ORGANISM: Artificial
<220> FEATURE:
<223> OTHER INFORMATION: SC RAG1 with HA tag and NLS

<400> SEQUENCE: 18

Met Tyr Pro Tyr Asp Val Pro Asp Tyr Ala Gly Phe Ala Ser Ala Pro
1               5                   10                  15

Lys Lys Lys Arg Lys Val Gly Ala Asn Thr Lys Tyr Asn Glu Glu Phe
            20                  25                  30

Leu Leu Tyr Leu Ala Gly Phe Val Asp Gly Asp Gly Ser Ile Ile Ala
        35                  40                  45

Gln Ile Asn Pro Asn Gln Ser Ser Lys Phe Lys His Arg Leu Arg Leu
```

```
                50                   55                   60
Thr Phe Tyr Val Thr Gln Lys Thr Gln Arg Arg Trp Phe Leu Asp Lys
 65                  70                  75                  80

Leu Val Asp Glu Ile Gly Val Gly Tyr Val Arg Asp Ser Gly Ser Val
                 85                  90                  95

Ser Gln Tyr Val Leu Ser Glu Ile Lys Pro Leu His Asn Phe Leu Thr
                100                 105                 110

Gln Leu Gln Pro Phe Leu Glu Leu Lys Gln Lys Gln Ala Asn Leu Val
            115                 120                 125

Leu Lys Ile Ile Glu Gln Leu Pro Ser Ala Lys Glu Ser Pro Asp Lys
130                 135                 140

Phe Leu Glu Val Cys Thr Trp Val Asp Gln Ile Ala Ala Leu Asn Asp
145                 150                 155                 160

Ser Lys Thr Arg Lys Thr Thr Ser Glu Thr Val Arg Ala Val Leu Asp
                165                 170                 175

Ser Leu Ser Gly Lys Lys Lys Ser Ser Pro Ala Ala Gly Gly Ser Asp
                180                 185                 190

Lys Tyr Asn Gln Ala Leu Ser Lys Tyr Asn Gln Ala Leu Ser Lys Tyr
            195                 200                 205

Asn Gln Ala Leu Ser Gly Gly Gly Ser Asn Lys Lys Phe Leu Leu
210                 215                 220

Tyr Leu Ala Gly Phe Val Asp Ser Asp Gly Ser Ile Ile Ala Gln Ile
225                 230                 235                 240

Lys Pro Arg Gln Ser Asn Lys Phe Lys His Gln Leu Ser Leu Thr Phe
                245                 250                 255

Ala Val Thr Gln Lys Thr Gln Arg Arg Trp Phe Leu Asp Lys Leu Val
                260                 265                 270

Asp Arg Ile Gly Val Gly Tyr Val Tyr Asp Ser Gly Ser Val Ser Asp
            275                 280                 285

Tyr Arg Leu Ser Glu Ile Lys Pro Leu His Asn Phe Leu Thr Gln Leu
290                 295                 300

Gln Pro Phe Leu Lys Leu Lys Gln Lys Gln Ala Asn Leu Val Leu Lys
305                 310                 315                 320

Ile Ile Glu Gln Leu Pro Ser Ala Lys Glu Ser Pro Asp Lys Phe Leu
                325                 330                 335

Glu Val Cys Thr Trp Val Asp Gln Ile Ala Ala Leu Asn Asp Ser Lys
                340                 345                 350

Thr Arg Lys Thr Thr Ser Glu Thr Val Arg Ala Val Leu Asp Ser Leu
            355                 360                 365

Ser Glu Lys Lys Lys Ser Ser Pro
370                 375

<210> SEQ ID NO 19
<211> LENGTH: 1131
<212> TYPE: DNA
<213> ORGANISM: Artificial
<220> FEATURE:
<223> OTHER INFORMATION: SC RAG1 coding sequence

<400> SEQUENCE: 19
atgtatcctt atgacgttcc tgattacgct ggatttgcta gcgcccccaa gaagaagagg      60
aaggtgggcg ccaataccaa atataacgaa gagttcctgc tgtacctggc cggctttgtg     120
gacggtgacg gtagcatcat cgctcagatt aatccaaaacc agtcttctaa gtttaaacat     180
cgtctacgtt tgaccttta tgtgactcaa aagacccagc gccgttggtt tctggacaaa     240
```

```
ctagtggatg aaattggcgt tggttacgta cgtgattctg gatccgtttc ccagtacgtt    300
ttaagcgaaa tcaagccgct gcacaacttc ctgactcaac tgcagccgtt tctggaactg    360
aaacagaaac aggcaaacct ggttctgaaa attatcgaac agctgccgtc tgcaaaagaa    420
tccccggaca aattcctgga agtttgtacc tgggtggatc agattgcagc tctgaacgat    480
tctaagacgc gtaaaaccac ttctgaaacc gttcgtgctg tgctggacag cctgagcggg    540
aagaagaaat cctccccggc ggccggtgga tctgataagt ataatcaggc tctgtctaaa    600
tacaaccaag cactgtccaa gtacaatcag gccctgtctg gtggaggcgg ttccaacaaa    660
aagttcctgc tgtatcttgc tggatttgtg gattctgatg gctccatcat tgctcagata    720
aaaccacgtc aatctaacaa gttcaaacac cagctctcct tgacttttgc agtcactcag    780
aagacacaaa gaaggtggtt cttggacaaa ttggttgata ggattggtgt gggctatgtc    840
tatgacagtg gctctgtgtc agactaccgc ctgtctgaaa ttaagcctct tcataacttt    900
ctcacccaac tgcaaccctt cttgaagctc aaacagaagc aagcaaatct ggttttgaaa    960
atcatcgagc aactgccatc tgccaaggag tcccctgaca gtttcttga agtgtgtact   1020 tgggtggatc agattgctgc cttgaatgac tccaagacca gaaaaaccac ctctgagact   1080
gtgagggcag ttctggatag cctctctgag aagaaaaagt cctctcctta g            1131
```

<210> SEQ ID NO 20
<211> LENGTH: 5510
<212> TYPE: DNA
<213> ORGANISM: Artificial
<220> FEATURE:
<223> OTHER INFORMATION: pCLS2262

<400> SEQUENCE: 20

```
gacggatcgg gagatctaaa gctaactgta ggactgagtc tattctaaac tgaaagcctg    60
gacatctgga gtaccagggg gagatgacgt gttacgggct tccataaaag cagctggctt   120
tgaatggaag gagccaagag gccagcacag gagcggattc gtcgctttca cggccatcga   180
gccgaacctc tcgcaagtcc gtgagccgtt aaggaggccc ccagtcccga cccttcgccc    240
caagcccctc ggggtccccg ggcctggtac tccttgccac acgggagggg cgcggaagcc   300
ggggcggagg aggagccaac cccgggctgg gctgagaccc gcagaggaag acgctctagg   360
gatttgtccc ggactagcga gatggcaagg ctgaggacgg gaggctgatt gagaggcgaa   420
ggtacaccct aatctcaata caaccctttgg agctaagcca gcaatggtag agggaagatt   480
ctgcacgtcc cttccaggcg gcctccccgt caccaccccc cccaacccgc cccgaccgga   540
gctgagagta attcatacaa aaggactcgc ccctgccttg gggaatccca gggaccgtcg    600
ttaaactccc actaacgtag aacccagaga tcgctgcgtt cccgcccct cacccgcccg    660 ctctcgtcat cactgaggtg gagaagagca tgcgtgaggc tccggtgccc gtcagtgggc   720
agagcgcaca tcgcccacag tccccgagaa gttgggggga gggtcggca attgaaccgg   780 tgcctagaga aggtggcgcg gggtaaactg ggaaagtgat gtcgtgtact ggctccgcct   840
ttttcccgag ggtgggggag aaccgtatat aagtgcagta gtcgccgtga acgttctttt   900
tcgcaacggg tttgccgcca gaacacaggt aagtgccgtg tgtggttccc gcgggcctgg   960
cctctttacg ggttatggcc cttgcgtgcc ttgaattact ccacgccccc tggctgcagt   1020
acgtgattct tgatcccgag cttcgggttg aagtgggtg ggagagttcg aggccttgcg   1080
cttaaggagc cccttcgcct cgtgcttgag ttgaggcctg gcttgggcgc tggggccgcc   1140
```

```
gcgtgcgaat ctggtggcac cttcgcgcct gtctcgctgc tttcgataag tctctagcca    1200
tttaaaattt ttgatgacct gctgcgacgc ttttttttctg gcaagatagt cttgtaaatg   1260
cgggccaaga tcgatctgca cactggtatt tcggtttttg gggccgcggg cggcgacggg    1320
gcccgtgcgt cccagcgcac atgttcggcg aggcggggcc tgcgagcgcg gccaccgaga    1380
atcggacggg ggtagtctca agctggccgg cctgctctgg tgcctggcct cgcgccgccg    1440
tgtatcgccc cgccctgggc ggcaaggctg gcccggtcgg caccagttgc gtgagcggaa    1500
agatggccgc ttcccggccc tgctgcaggg agctcaaaat ggaggacgcg gcgctcggga    1560
gagcgggcgg gtgagtcacc cacacaaagg aaaagggcct ttccgtcctc agccgtcgct    1620
tcatgtgact ccacggagta ccgggcgccg tccaggcacc tcgattagtt ctcgagcttt    1680
tggagtacgt cgtctttagg ttgggggggag gggttttatg cgatggagtt tccccacact   1740
gagtgggtgg agactgaagt taggccagct tggcacttga tgtaattctc cttggaattt    1800 gcccttttttg agtttggatc ttggttcatt ctcaagcctc agacagtggt tcaaagtttt   1860
tttcttccat ttcaggtgtc gtggaattcg ccgccatgta tccttatgac gttcctgatt    1920
acgctggatt tgctagcgcc cccaagaaga agaggaaggt gggcgccaat accaaatata    1980
acgaagagtt cctgctgtac ctggccggct tgtggacgg tgacgtagc atcatcgctc      2040 agattaatcc aaaccagtct tctaagttta aacatcgtct acgtttgacc ttttatgtga    2100
ctcaaaagac ccagcgccgt tggttttctgg acaaactagt ggatgaaatt ggcgttggtt   2160
acgtacgtga ttctggatcc gttttcccagt acgttttaag cgaaatcaag ccgctgcaca   2220
acttcctgac tcaactgcag ccgtttctgg aactgaaaca gaaacaggca aacctggttc    2280
tgaaaattat cgacagctg ccgtctgcaa aagaatcccc ggacaaattc ctggaagttt     2340
gtacctgggt ggatcagatt gcagctctga acgattctaa gacgcgtaaa accacttctg    2400
aaaccgttcg tgctgtgctg gacagcctga gcgggaagaa gaaatcctcc ccggcggccg    2460
gtggatctga taagtataat caggctctgt ctaaatacaa ccaagcactg tccaagtaca    2520
atcaggccct gtctggtgga ggcggttcca acaaaaagtt cctgctgtat cttgctggat    2580
ttgtggattc tgatggctcc atcattgctc agataaaacc acgtcaatct aacaagttca    2640
aacaccagct ctccttgact tttgcagtca ctcagaagac acaaagaagg tggttcttgg    2700
acaaattggt tgataggatt ggtgtgggct atgtctatga cagtggctct gtgtcagact    2760
accgcctgtc tgaaattaag cctcttcata actttctcac ccaactgcaa cccttcttga    2820
agctcaaaca gaagcaagca aatctggttt tgaaaatcat cgagcaactg ccatctgcca    2880
aggagtcccc tgacaagttt cttgaagtgt gtacttgggt ggatcagatt gctgccttga    2940
atgactccaa gaccagaaaa accacctctg agactgtgag ggcagttctg gatagcctct    3000
ctgagaagaa aaagtcctct ccttagttcg aaatgaccga ccaagcgacg cccaacctgc    3060
catcacgaga tttcgattcc accgccgcct tctatgaaag gttgggcttc ggaatcgttt    3120
tccgggacgc cggctggatg atcctccagc gcggggatct catgctggag ttcttcgccc   3180
accccaactt gtttattgca gcttataatg gttacaaata aagcaatagc atcacaaatt    3240
tcacaaataa agcattttttt tcactgcatt ctagttgtgg tttgtccaaa ctcatcaatg   3300
tatcttatca tgtctgtata ccgtcgacct ctagctagag cttggcgtaa tcatggtcat    3360 agctgttttcc tgtgtgaaat tgttatccgc tcacaattcc acacaacata cgagccggaa   3420
gcataaagtg taaagcctgg ggtgcctaat gagtgagcta actcacatta attgcgttgc    3480
gctcactgcc cgctttccag tcgggaaacc tgtcgtgcca gctgcattaa tgaatcggcc    3540
```

```
aacgcgcggg gagaggcggt ttgcgtattg ggcgctcttc cgcttcctcg ctcactgact   3600
cgctgcgctc ggtcgttcgg ctgcggcgag cggtatcagc tcactcaaag gcggtaatac   3660
ggttatccac agaatcaggg gataacgcag gaaagaacat gtgagcaaaa ggccagcaaa   3720
aggccaggaa ccgtaaaaag gccgcgttgc tggcgttttt ccataggctc cgcccccctg   3780
acgagcatca caaaaatcga cgctcaagtc agaggtggcg aaacccgaca ggactataaa   3840
gataccaggc gtttccccct ggaagctccc tcgtgcgctc tcctgttccg accctgccgc   3900
ttaccggata cctgtccgcc tttctccctt cgggaagcgt ggcgctttct catagctcac   3960
gctgtaggta tctcagttcg gtgtaggtcg ttcgctccaa gctgggctgt gtgcacgaac   4020
cccccgttca gcccgaccgc tgcgccttat ccggtaacta tcgtcttgag tccaacccgg   4080
taagacacga cttatcgcca ctggcagcag ccactggtaa caggattagc agagcgaggt   4140
atgtaggcgg tgctacagag ttcttgaagt ggtggcctaa ctacggctac actagaagaa   4200
cagtatttgg tatctgcgct ctgctgaagc cagttacctt cggaaaaaga gttggtagct   4260
cttgatccgg caaacaaacc accgctggta gcggtttttt tgtttgcaag cagcagatta   4320
cgcgcagaaa aaaaggatct caagaagatc ctttgatctt ttctacgggg tctgacgctc   4380
agtggaacga aaactcacgt taagggattt tggtcatgag attatcaaaa aggatcttca   4440
cctagatcct tttaaattaa aaatgaagtt ttaaatcaat ctaaagtata tatgagtaaa   4500
cttggtctga cagttaccaa tgcttaatca gtgaggcacc tatctcagcg atctgtctat   4560
ttcgttcatc catagttgcc tgactccccg tcgtgtagat aactacgata cgggagggct   4620
taccatctgg ccccagtgct gcaatgatac cgcgagaccc acgctcaccg gctccagatt   4680
tatcagcaat aaaccagcca gccggaaggg ccgagcgcag aagtggtcct gcaactttat   4740
ccgcctccat ccagtctatt aattgttgcc gggaagctag agtaagtagt tcgccagtta   4800
atagtttgcg caacgttgtt gccattgcta caggcatcgt ggtgtcacgc tcgtcgtttg   4860
gtatggcttc attcagctcc ggttcccaac gatcaaggcg agttacatga tcccccatgt   4920
tgtgcaaaaa agcggttagc tccttcggtc ctccgatcgt tgtcagaagt aagttggccg   4980
cagtgttatc actcatggtt atggcagcac tgcataattc tcttactgtc atgccatccg   5040
taagatgctt ttctgtgact ggtgagtact caaccaagtc attctgagaa tagtgtatgc   5100
ggcgaccgag ttgctcttgc ccggcgtcaa tacgggataa taccgcgcca catagcagaa   5160
ctttaaaagt gctcatcatt ggaaaacgtt cttcggggcg aaaactctca aggatcttac   5220
cgctgttgag atccagttcg atgtaaccca ctcgtgcacc caactgatct tcagcatctt   5280
ttactttcac cagcgtttct gggtgagcaa aaacaggaag gcaaaatgcc gcaaaaaagg   5340
gaataagggc gacacggaaa tgttaatac tcatactctt cctttttcaa tattattgaa   5400
gcatttatca gggttattgt ctcatgagcg gatacatatt tgaatgtatt tagaaaaata   5460
aacaaatagg ggttccgcgc acatttcccc gaaaagtgcc acctgacgtc                5510
```

<210> SEQ ID NO 21
<211> LENGTH: 783
<212> TYPE: DNA
<213> ORGANISM: Artificial
<220> FEATURE:
<223> OTHER INFORMATION: I-SceI with HA tag and NLS coding sequence

<400> SEQUENCE: 21

```
atgtatcctt atgacgttcc tgattacgct ggatttgcta gcgccccaa gaagaagagg       60
```

```
aaggtggcca aaaacatcaa aaaaaaccag gtaatgaacc tgggtccgaa ctctaaactg      120
ctgaaagaat acaaatccca gctgatcgaa ctgaacatcg aacagttcga agcaggtatc      180
ggtctgatcc tgggtgatgc ttacatccgt tctcgtgatg aaggtaaaac ctactgtatg      240
cagttcgagt ggaaaaacaa agcatacatg gaccacgtat gtctgctgta cgatcagtgg      300
gtactgtccc cgccgcacaa aaagaacgt gttaaccacc tgggtaacct ggtaatcacc        360
tggggcgccc agactttcaa acaccaagct ttcaacaaac tggctaacct gttcatcgtt      420
aacaacaaaa aaaccatccc gaacaacctg gttgaaaact acctgacccc gatgtctctg      480
gcatactggt tcatggatga tggtggtaaa tgggattaca caaaaactc taccaacaaa       540 tcgatcgtac tgaacaccca gtctttcact ttcgaagaag tagaatacct ggttaagggt      600
ctgcgtaaca aattccaact gaactgttac gtaaaaatca caaaaacaa accgatcatc       660 tacatcgatt ctatgtctta cctgatcttc tacaacctga tcaaaccgta cctgatcccg      720
cagatgatgt acaaactgcc gaacactatc tcctccgaaa ctttcctgaa agcggccgac      780
taa                                                                    783

<210> SEQ ID NO 22
<211> LENGTH: 5171
<212> TYPE: DNA
<213> ORGANISM: Artificial
<220> FEATURE:
<223> OTHER INFORMATION: pCLS2209

<400> SEQUENCE: 22
gacggatcgg gagatctaaa gctaactgta ggactgagtc tattctaaac tgaaagcctg       60
gacatctgga gtaccagggg gagatgacgt gttacgggct tccataaaag cagctggctt      120
tgaatggaag gagccaagag gccagcacag gagcggattc gtcgctttca cggccatcga      180
gccgaacctc tcgcaagtcc gtgagccgtt aaggaggccc ccagtcccga cccttcgccc      240
caagcccctc ggggtccccg ggctggtac tccttgccac acgggagggg cgcggaagcc       300
ggggcggagg aggagccaac cccgggctgg gctgagaccc gcagaggaag acgctctagg      360
gatttgtccc ggactagcga gatggcaagg ctgaggacgg gaggctgatt gagaggcgaa      420
ggtacaccct aatctcaata caaccctttgg agctaagcca gcaatggtag agggaagatt      480
ctgcacgtcc cttccaggcg gcctccccgt caccacccc cccaacccgc cccgaccgga       540
gctgagagta attcatacaa aaggactcgc ccctgccttg gggaatccca gggaccgtcg      600
ttaaactccc actaacgtag aacccagaga tcgctgcgtt cccgcccccct cacccgcccg    660 ctctcgtcat cactgaggtg gagaagagca tgcgtgaggc tccggtgccc gtcagtgggc      720
agagcgcaca tcgcccacag tccccgagaa gttgggggga ggggtcggca attgaaccgg      780
tgcctagaga aggtggcgcg gggtaaactg ggaaagtgat gtcgtgtact ggctccgcct      840 tttttcccgag ggtgggggag aaccgtatat aagtgcagta gtcgccgtga acgttctttt     900
tcgcaacggg tttccgccgca gaacacaggt aagtgccgtg tgtggttccc gcgggcctgg    960
cctctttacg ggttatggcc cttgcgtgcc ttgaattact ccacgccccc tggctgcagt     1020
acgtgattct tgatcccgag cttcgggttg aagtgggtg ggagagttcg aggccttgcg      1080
cttaaggagc cccttcgcct cgtgcttgag ttgaggcctg gcttgggcgc tggggccgcc    1140
gcgtgcgaat ctggtggcac cttgcgcgcct gtctcgctgc tttcgataag tctctagcca   1200
tttaaaattt ttgatgacct gctgcgacgc ttttttttctg gcaagatagt cttgtaaatg   1260
cgggccaaga tcgatctgca cactggtatt tcggttttttg gggccgcggg cggcgacggg   1320
```

```
gcccgtgcgt cccagcgcac atgttcggcg aggcggggcc tgcgagcgcg gccaccgaga    1380
atcggacggg ggtagtctca agctggccgg cctgctctgg tgcctggcct cgcgccgccg    1440
tgtatcgccc cgccctgggc ggcaaggctg gcccggtcgg caccagttgc gtgagcggaa    1500
agatggccgc ttcccggccc tgctgcaggg agctcaaaat ggaggacgcg cgctcgggaa    1560
gagcgggcgg gtgagtcacc cacacaaagg aaaagggcct ttccgtcctc agccgtcgct    1620
tcatgtgact ccacggagta ccgggcgccg tccaggcacc tcgattagtt ctcgagcttt    1680
tggagtacgt cgtctttagg ttgggggggag gggttttatg cgatggagtt ccccacact    1740 gagtgggtgg agactgaagt taggccagct tggcacttga tgtaattctc cttggaattt    1800 gcccttttg agtttggatc ttggttcatt ctcaagcctc agacagtggt tcaaagtttt    1860
tttcttccat ttcaggtgtc gtggaattcg ccgccatgta tccttatgac gttcctgatt    1920
acgctggatt tgctagcgcc cccaagaaga agaggaaggt ggccaaaaac atcaaaaaaa    1980
accaggtaat gaacctgggt ccgaactcta aactgctgaa agaatacaaa tcccagctga    2040
tcgaactgaa catcgaacag ttcgaagcag gtatcggtct gatcctgggt gatgcttaca    2100
tccgttctcg tgatgaaggt aaaacctact gtatgcagtt cgagtggaaa aacaaagcat    2160
acatggacca cgtatgtctg ctgtacgatc agtgggtact gtccccgccg cacaaaaaag    2220
aacgtgttaa ccacctgggt aacctggtaa tcacctgggg cgcccagact ttcaaacacc    2280 aagcttttcaa caaactggct aacctgttca tcgttaacaa caaaaaaacc atcccgaaca    2340
acctggttga aaactacctg accccgatgt ctctggcata ctggttcatg gatgatggtg    2400
gtaaatggga ttacaacaaa aactctacca acaaatcgat cgtactgaac cccagtctt    2460 tcactttcga agaagtagaa tacctggtta agggtctgcg taacaaattc caactgaact    2520
gttacgtaaa aatcaacaaa aacaaaccga tcatctacat cgattctatg tcttacctga    2580
tcttctacaa cctgatcaaa ccgtacctga tcccgcagat gatgtacaaa ctgccgaaca    2640
ctatctcctc cgaaactttc ctgaaagcgg ccgactaagc tagctgattc gaaatgaccg    2700
accaagcgac gcccaacctg ccatcacgag atttcgattc caccgccgcc ttctatgaaa    2760
ggttgggctt cggaatcgtt ttccgggacg ccggctggat gatcctccag cgcggggatc    2820
tcatgctgga gttcttcgcc caccccaact tgtttattgc agcttataat ggttacaaat    2880
aaagcaatag catcacaaat ttcacaaata agcattttt ttcactgcat tctagttgtg    2940
gtttgtccaa actcatcaat gtatcttatc atgtctgtat accgtcgacc tctagctaga    3000
gcttggcgta atcatggtca tagctgtttc ctgtgtgaaa ttgttatccg ctcacaattc    3060
cacacaacat acgagccgga agcataaagt gtaaagcctg gggtgcctaa tgagtgagct    3120
aactcacatt aattgcgttg cgctcactgc ccgctttcca gtcgggaaac ctgtcgtgcc    3180
agctgcatta atgaatcggc caacgcgcgg ggagaggcgg tttgcgtatt gggcgctctt    3240
ccgcttcctc gctcactgac tcgctgcgct cggtcgttcg gctgcggcga gcggtatcag    3300
ctcactcaaa ggcggtaata cggttatcca cagaatcagg ggataacgca ggaaagaaca    3360
tgtgagcaaa aggccagcaa aaggccagga accgtaaaaa ggccgcgttg ctggcgtttt    3420
tccataggct ccgcccccct gacgagcatc acaaaaatcg acgctcaagt cagaggtggc    3480
gaaacccgac aggactataa agataccagg cgtttccccc tggaagctcc ctcgtgcgct    3540
ctcctgttcc gaccctgccg cttaccggat acctgtccgc ctttctccct cgggaagcg    3600 tggcgctttc tcatagctca cgctgtaggt atctcagttc ggtgtaggtc gttcgctcca    3660
```

```
agctgggctg tgtgcacgaa ccccccgttc agcccgaccg ctgcgcctta tccggtaact    3720
atcgtcttga gtccaacccg gtaagacacg acttatcgcc actggcagca gccactggta    3780
acaggattag cagagcgagg tatgtaggcg gtgctacaga gttcttgaag tggtggccta    3840
actacggcta cactagaaga acagtatttg gtatctgcgc tctgctgaag ccagttacct    3900
tcggaaaaag agttggtagc tcttgatccg gcaaacaaac caccgctggt agcggttttt    3960
ttgtttgcaa gcagcagatt acgcgcagaa aaaaaggatc tcaagaagat cctttgatct    4020
tttctacggg gtctgacgct cagtggaacg aaaactcacg ttaagggatt ttggtcatga    4080
gattatcaaa aaggatcttc acctagatcc ttttaaatta aaaatgaagt tttaaatcaa    4140
tctaaagtat atatgagtaa acttggtctg acagttacca atgcttaatc agtgaggcac    4200
ctatctcagc gatctgtcta tttcgttcat ccatagttgc ctgactcccc gtcgtgtaga    4260
taactacgat acgggagggc ttaccatctg gccccagtgc tgcaatgata ccgcgagacc    4320
cacgctcacc ggctccagat ttatcagcaa taaaccagcc agccggaagg gccgagcgca    4380
gaagtggtcc tgcaacttta tccgcctcca tccagtctat taattgttgc cgggaagcta    4440
gagtaagtag ttcgccagtt aatagtttgc gcaacgttgt tgccattgct acaggcatcg    4500
tggtgtcacg ctcgtcgttt ggtatggctt cattcagctc cggttcccaa cgatcaaggc    4560
gagttacatg atcccccatg ttgtgcaaaa aagcggttag ctccttcggt cctccgatcg    4620
ttgtcagaag taagttggcc gcagtgttat cactcatggt tatggcagca ctgcataatt    4680
ctcttactgt catgccatcc gtaagatgct tttctgtgac tggtgagtac tcaaccaagt    4740
cattctgaga atagtgtatg cggcgaccga gttgctcttg cccggcgtca atacgggata    4800
ataccgcgcc acatagcaga actttaaaag tgctcatcat tggaaaacgt tcttcggggc    4860
gaaaactctc aaggatctta ccgctgttga gatccagttc gatgtaaccc actcgtgcac    4920
ccaactgatc ttcagcatct tttactttca ccagcgtttc tgggtgagca aaaacaggaa    4980
ggcaaaatgc cgcaaaaaag ggaataaggg cgacacggaa atgttgaata ctcatactct    5040
tcctttttca atattattga agcatttatc agggttattg tctcatgagc ggatacatat    5100
ttgaatgtat ttagaaaaat aaacaaatag gggttccgcg cacatttccc cgaaaagtgc    5160
cacctgacgt c                                                         5171
```

<210> SEQ ID NO 23
<211> LENGTH: 3840
<212> TYPE: DNA
<213> ORGANISM: Artificial
<220> FEATURE:
<223> OTHER INFORMATION: Dog Micro-Dystrophin cDNA

<400> SEQUENCE: 23

```
atgctttggt gggaagaagt agaggactgt tatgaaagag aagatgttca aaagaaaaca      60
ttcacaaaat ggataaatgc acagttttct aagtttggga agcagcacat agagaacctc     120
ttcagtgacc tacaggatgg gagacgcctc ctagaccttt tggaaggcct gacagggcaa     180
aaactgccaa agaaaaagg atccacaaga gttcatgccc tgaacaatgt caacaaggca     240
ctgcgcgtct tgcagaaaaa taatgttgat ttagtgaaca ttggaagtac tgacatagta     300
gatggaaatc acaaactgac tcttggtttg atttggaata ataatcctcca ctggcaggtc     360 aaaaatgtaa tgaaaatat catggctgga ttgcaacaaa ccaacagtga aaagattctc     420
ctgagctggg tccgacaatc aactcgtaat tatccacagg ttaatgtcat taacttcacc     480
accagctggt ctgatggcct ggctttgaac gctctcatcc acagtcatag gccagacctg     540
```

```
tttgattgga atagtgtggt ttgccagcag tcagccacac aacgcctgga acatgcattc    600
aacattgcca aatatcaatt aggcatagag aaactgcttg atcctgaaga tgttgccacc    660
acttatccag ataagaagtc catcttaatg tatatcacat cactcttcca agttttgcct    720
caacaagtga gcattgaagc catccaggaa gtggaaatgt tgccaaggcc atcaaaagtt    780
actagagaag aacattttca attacatcat caaatgcact attctcaaca gatcacagtc    840
agtctagcac agggctatga acgagcccct cctctcata agcctcggtt caagagctat     900
gcctacacac aggctgctta tgtcaccact tctgacccca cacggagccc acttccttca    960
cagcatttgg aaactcctga agacaagtca tttggccggt cattgacaga gaccgaagca   1020
aacctggaca gttatcaaac agctttggaa gaagtactct cgtggcttct ttcagctgag   1080
gatgcactgc aagcccaagg agagatttct aatgatgtcg aagaagtgaa agaacaattt   1140
catactcatg agggatatat gatggacttg acatcccatc agggacgggt cggtaatgtt   1200
ctccaactgg gaagtcaact gattggaaca gggaaattat cagaagatga agaaaccgaa   1260
gtgcaggaac aaatgaatct cctcaattca agatgggaat gcctcagggt agctagcatg   1320
gaaaaacaaa gcaatttaca taaagttcta atggatctcc agaatcagca actgaaagag   1380
ttaaatgact ggctaaccaa aacagaagag agaacaagga aaatggagaa ggagcccctt   1440
ggacctgata ttgaagacct aaaacgccaa gtacaacaac ataaggtgct tcaagaagac   1500
ttagaacagg aacaagtcag ggtcaattcc ctcactcata tggtggtggt agtcgatgaa   1560
tctagtggag accatgcaac tgctgctttg aagaacaac ttaaggtact gggagatcga    1620
tgggcaaaca tctgtaggtg gacagaagat cgctgggttc ttttacaaga cacccacaga   1680
ttactgcaac agttcccctt ggacctggag aagttccttg cctggcttac agaagccgaa   1740
acaactgcca acgtcctgca ggatgccacc cataaggaaa ggcttctaga agattccaag   1800
ggagtaagag agctgatgaa acaatggcaa gatctccaag gagaaatcga agctcacaca   1860
gatatctatc acaacctgga cgaaaatggc caaaaagtcc tgagatccct ggaaggttct   1920
gacgatgcag ccttgttgca agacgttttg gataacatga acttcaagtg gagcgaactt   1980
cggaaaaagt ctctcaacat taggtctcac ttggaagcca gttctgacca gtggaagcgt   2040
ctgcaccttt ctcttcagga acttctggta tggctccagc tgaaagatga tgagttaagc   2100
cggcaggcac ccattggagg agactttcca gcggtgcaga agcagaatga tgtacacagg   2160
gccttcaaga gggaattgaa aacgaaagaa cctgtaatca tgagtactct tgagactgta   2220
cgaatatttc tgacagagca gcctttagaa ggactagaga aactctacca ggagcccaga   2280
gagctgcctc ctgaagagag agcccagaat gtcacacggc tcctacgaaa gcaagctgag   2340
gaggtcaaca ctcagtggga aaaactgaac gtgcactctg cagactggca gagaaaaata   2400
gacgaggccc tcgaaagact ccaggagctt caggaagcaa cagatgagct ggatctcaaa   2460
ctacgtcagg cagaggtgat caaaggatcc tggcagcctg tgggtgatct cctcattgac   2520
tctctccaag atcacctcga aaaagtcaag gcgcttcgag agaaattac acctctgaaa    2580 gagaatgtca gctacgtcaa tgaccttgct cgccaactca ctacgttggg cattcagctg   2640
tcaccatata acctcaacac tctggaagac ctgaacacca gatggaagct tctgcaggtg   2700
gccattgagg accgcatcag gcagctgcat gaagcgcaca gggactttgg accagcctcc   2760
cagcacttcc tttccacttc tgtccagggt ccctgggaga gagccatctc accaaacaaa   2820
gtgccctact atatcaacca cgagacccaa acaacttgct gggaccatcc caaaatgaca   2880
```

-continued

| | |
|---|---|
| gagctctacc agtctttagc tgacctgaat aatgtcagat tctcagctta caggactgcc | 2940 |
| atgaaactcc gaagactgca gaaggccctt tgcttggatc tcttgagcct atcggctgca | 3000 |
| tgcgatgcct tggaccagca aacctcaag caaaatgacc agcccatgga tatcctgcag | 3060 |
| gtcattaact gtctgaccac tatttatgat cgcctagagc aagagcacaa caatctggtc | 3120 |
| aacgtccctc tctgcgtgga tatgtgtctc aattggctgc tgaatgttta tgacacggga | 3180 |
| cgaacgggga ggatccgggt cctgtctttt aaaactggca tcatttctct gtgtaaagcc | 3240 |
| catttggaag acaagtacag atacctcttc aagcaagtgg caagttcgac aggattttgt | 3300 |
| gaccagcgca ggctgggcct cctcctgcat gactctatcc agatcccaag acagttgggt | 3360 |
| gaagtcgcat cgttcggggg cagtaacatt gagccgagtg tcaggagctg cttccagttt | 3420 |
| gctaataata agcctgagat cgaagcggcc ctcttcctag actggatgcg cctggagccc | 3480 |
| cagtccatgg tgtggctgcc tgtcctgcac cgagtggctg ccgcggaaac tgccaagcac | 3540 |
| caggccaagt gcaacatctg caaggagtgt cccatcatcg gattcaggta caggagtcta | 3600 |
| aagcacttta attatgacat ctgccaaagt tgcttttttt ctggtcgagt tgcaaaaggc | 3660 |
| cataaaatgc actatcccat ggtggaatac tgcactccga ctacatcggg agaagatgtc | 3720 |
| cgtgactttg ccaaggtact aaaaaacaaa tttcgaacca aaaggtattt tgcgaagcat | 3780 |
| ccccgaatgg gctacctgcc agtgcagact gtcttagagg gggacaacat ggaaacttag | 3840 |

<210> SEQ ID NO 24
<211> LENGTH: 9042
<212> TYPE: DNA
<213> ORGANISM: Artificial
<220> FEATURE:
<223> OTHER INFORMATION: AAV1dog micro-dystrophin

<400> SEQUENCE: 24

| | |
|---|---|
| aattcccatc atcaataata taccttattt tggattgaag ccaatatgat aatgagggggg | 60 |
| tggagtttgt gacgtggcgc ggggcgtggg aacggggcgg gtgacgtagt agtctctaga | 120 |
| ggtccccagc gaccttgacg ggcatctgcc cggcatttct gacagctttg tgaactgggt | 180 |
| ggccgagaag gaatgggagt tgccgccaga ttctgacatg gatctgaatc tgattgagca | 240 |
| ggcacccctg accgtggccg agaagctgca tcgctggcgt aatagcgaag aggcccgcac | 300 |
| cgatcgccct tcccaacagt tgcgcagcct gaatggcgaa tggaattcca cgacgattgag | 360 |
| cgtcaaaatg taggtatttc catgagcgtt tttcctgttg caatggctgg cggtaatatt | 420 |
| gttctggata ttaccagcaa ggccgatagt ttgagttctt ctactcaggc aagtgatgtt | 480 |
| attactaatc aaagaagtat tgcgacaacg gttaatttgc gtgatggaca gactcttttta | 540 |
| ctcggtggcc tcactgatta taaaaacact tctcaggatt ctggcgtacc gttcctgtct | 600 |
| aaaatccctt taatcggcct cctgtttagc tcccgctctg attctaacga ggaaagcacg | 660 |
| ttatacgtgc tcgtcaaagc aaccatagta cgcgccctgt agcggcgcat taagcgcggc | 720 |
| gggtgtggtg gttacgcgca gcgtgaccgc tacacttgcc agcgccctag cgcccgctcc | 780 |
| tttcgctttc ttcccttcct ttctcgccac gttcgccggc tttccccgtc aagctctaaa | 840 |
| tcggggctc cctttagggt tccgatttag tgctttacgg cacctcgacc ccaaaaaact | 900 |
| tgattagggt gatggttcac gtagtgggcc atcgccctga tagacggttt ttcgcccttt | 960 |
| gacgttggag tccacgttct ttaatagtgg actcttgttc caaactggaa caacactcaa | 1020 |
| ccctatctcg gtctattctt ttgatttata agggattttg ccgatttcgg cctattggtt | 1080 |
| aaaaaatgag ctgatttaac aaaaatttaa cgcgaatttt aacaaaatat taacgtttac | 1140 |

```
aatttaaata tttgcttata caatcttcct gttttttgggg cttttctgat tatcaaccgg    1200
ggtacatatg attgacatgc tagttttacg attaccgttc atcgcctgca ggggggggggg    1260 ggggggggtt ggccactccc tctctgcgcg ctcgctcgct cactgaggcc gggcgaccaa    1320
aggtcgcccg acgcccgggc tttgcccggg cggcctcagt gagcgagcga gcgcgcagag    1380
agggagtggc caactccatc actaggggtt cctagatctg aattcggtac ccgttacata    1440
acttacggta aatggcccgc ctggctgacc gcccaacgac ccccgcccat tgacgtcaat    1500
aatgacgtat gttcccatag taacgccaat agggactttc cattgacgtc aatgggtgga    1560
gtatttacgg taaactgccc acttggcagt acatcaagtg tatcatatgc caagtacgcc    1620
ccctattgac gtcaatgacg gtaaatggcc cgcctggcat tatgcccagt acatgacctt    1680
atgggacttt cctacttggc agtacatcta cgtattagtc atcgctatta ccatggtgat    1740
gcggttttgg cagtacatca atgggcgtgg atagcggttt gactcacggg gatttccaag    1800
tctccacccc attgacgtca atgggagttt gttttggcac caaaatcaac gggactttcc    1860
aaaatgtcgt aacaactccg ccccattgac gcaaatgggc ggtaggcgtg tacggtggga    1920
ggtctatata agcagagctc gtttagtgaa ccgtcagatc gcctggagac gccatccacg    1980
ctgttttgac ctccatagaa gacaccggga ccgatccagc ctccggactc tagaggatcc    2040
ggtactcgag gccgctctag aactagtgga tcccccgggc tgcaggaatt cgatgccacc    2100
atgctttggt gggaagaagt agaggactgt tatgaaagag aagatgttca aagaaaaca    2160 ttcacaaaat ggataaatgc acagtttttct aagtttggga agcagcacat agagaacctc    2220
ttcagtgacc tacaggatgg gagacgcctc ctagaccttt tggaaggcct gacagggcaa    2280
aaactgccaa agaaaaagg atccacaaga gttcatgccc tgaacaatgt caacaaggca    2340
ctgcgcgtct tgcagaaaaa taatgttgat ttagtgaaca ttggaagtac tgacatagta    2400 gatgaaatc acaaactgac tcttggtttg atttggaata taatcctcca ctggcaggtc    2460
aaaaatgtaa tgaaaatat catggctgga ttgcaacaaa ccaacagtga aaagattctc    2520
ctgagctggg tccgacaatc aactcgtaat tatccacagg ttaatgtcat taacttcacc    2580
accagctggt ctgatggcct ggctttgaac gctctcatcc acagtcatag gccagacctg    2640
tttgattgga atagtgtggt ttgccagcag tcagccacac aacgcctgga acatgcattc    2700
aacattgcca aatatcaatt aggcatagag aaactgcttg atcctgaaga tgttgccacc    2760
acttatccag ataagaagtc catcttaatg tatatcacat cactcttcca agttttgcct    2820
caacaagtga gcattgaagc catccaggaa gtggaaatgt tgccaaggcc atcaaaagtt    2880
actagagaag aacattttca attacatcat caaatgcact attctcaaca gatcacagtc    2940
agtctagcac agggctatga acgagcccct tcctctcata agcctcggtt caagagctat    3000
gcctacacac aggctgctta tgtcaccact tctgacccca cacggagccc acttccttca    3060
cagcatttgg aaactcctga agacaagtca tttggccggt cattgacaga gccgaagca    3120 aacctggaca gttatcaaac agctttggaa gaagtactct cgtggcttct ttcagctgag    3180
gatgcactgc aagcccaagg agagatttct aatgatgtcg aagaagtgaa agaacaattt    3240
catactcatg agggatatat gatggacttg acatcccatc agggacgggt cggtaatgtt    3300
ctccaactgg gaagtcaact gattggaaca gggaaattat cagaagatga agaaaccgaa    3360
gtgcaggaac aaatgaatct cctcaattca agatgggaat gcctcagggt agctagcatg    3420
gaaaaacaaa gcaatttaca taagttcta atggatctcc agaatcagca actgaaagag    3480
```

```
ttaaatgact ggctaaccaa acagaagag agaacaagga aaatggagaa ggagcccctt    3540
ggacctgata ttgaagacct aaaacgccaa gtacaacaac ataaggtgct tcaagaagac    3600
ttagaacagg aacaagtcag ggtcaattcc ctcactcata tggtggtggt agtcgatgaa    3660
tctagtggag accatgcaac tgctgctttg gaagaacaac ttaaggtact gggagatcga    3720
tgggcaaaca tctgtaggtg gacagaagat cgctgggttc ttttacaaga cacccacaga    3780
ttactgcaac agttcccctt ggacctggag aagttccttg cctggcttac agaagccgaa    3840
acaactgcca acgtcctgca ggatgccacc cataaggaaa ggcttctaga agattccaag    3900
ggagtaagag agctgatgaa acaatggcaa gatctccaag gagaaatcga agctcacaca    3960
gatatctatc acaacctgga cgaaaatggc caaaaagtcc tgagatccct ggaaggttct    4020
gacgatgcag ccttgttgca agacgtttg gataacatga acttcaagtg gagcgaactt    4080
cggaaaaagt ctctcaacat taggtctcac ttggaagcca gttctgacca gtggaagcgt    4140
ctgcaccttt ctcttcagga acttctggta tggctccagc tgaaagatga tgagttaagc    4200
cggcaggcac ccattggagg agactttcca gcggtgcaga agcagaatga tgtacacagg    4260
gccttcaaga gggaattgaa acgaaagaa cctgtaatca tgagtactct tgagactgta    4320
cgaatatttc tgacagagca gcctttagaa ggactagaga actctaccca ggagcccaga    4380
gagctgcctc ctgaagagag agcccagaat gtcacacggc tcctacgaaa gcaagctgag    4440
gaggtcaaca ctcagtggga aaaactgaac gtgcactctg cagactggca gagaaaaata    4500
gacgaggccc tcgaaagact ccaggagctt caggaagcaa cagatgagct ggatctcaaa    4560
ctacgtcagg cagaggtgat caaaggatcc tggcagcctg tgggtgatct cctcattgac    4620
tctctccaag atcacctcga aaaagtcaag gcgcttcgag agaaattac acctctgaaa    4680 gagaatgtca gctacgtcaa tgaccttgct cgccaactca ctacgttggg cattcagctg    4740
tcaccatata acctcaacac tctggaagac ctgaacacca gatggaagct tctgcaggtg    4800
gccattgagg accgcatcag gcagctgcat gaagcgcaca gggactttgg accagcctcc    4860
cagcacttcc tttccacttc tgtccagggt ccctgggaga gagccatctc accaaacaaa    4920
gtgccctact atatcaacca cgagacccaa acaacttgct gggaccatcc caaaatgaca    4980
gagctctacc agtctttagc tgacctgaat aatgtcagat ctcagcttac aggactgcc    5040 atgaaactcc gaagactgca gaaggccctt gcttggatc tcttgagcct atcggctgca    5100
tgcgatgcct ggaccagca caacctcaag caaaatgacc agcccatgga tatcctgcag    5160
gtcattaact gtctgaccac tatttatgat cgcctagagc aagagcacaa caatctggtc    5220
aacgtccctc tctgcgtgga tatgtgtctc aattggctgc tgaatgttta tgacacggga    5280
cgaacgggga ggatccgggt cctgtctttt aaaactggca tcatttctct gtgtaaagcc    5340
catttggaag acaagtacag ataccctcttc aagcaagtgg caagttcgac aggattttgt    5400
gaccagcgca ggctgggcct cctcctgcat gactctatcc agatcccaag acagttgggt    5460
gaagtcgcat cgttcggggg cagtaacatt gagccgagtg tcaggagctg cttccagttt    5520
gctaataata agcctgagat cgaagcggcc ctcttcctag actggatgcg cctggagccc    5580
cagtccatgg tgtggctgcc tgtcctgcac cgagtggctg ccgcggaaac tgccaagcac    5640
caggccaagt gcaacatctg caaggagtgt cccatcatcg gattcaggta caggagtcta    5700
aagcacttta attatgacat ctgccaaagt tgctttttt ctggtcgagt tgcaaaggc    5760 cataaaatgc actatcccat ggtggaatac tgcactccga ctacatcggg agaagatgtc    5820
cgtgactttg ccaaggtact aaaaaacaaa tttcgaacca aaaggtattt tgcgaagcat    5880
```

```
ccccgaatgg gctacctgcc agtgcagact gtcttagagg gggacaacat ggaaacttag      5940
atcaagctta tcgataccgt cgatcgacta gagctcgctg atcagcctcg actgtgcctt      6000
ctagttgcca gccatctgtt gtttgcccct ccccgtgcc ttccttgacc ctggaaggtg       6060
ccactcccac tgtcctttcc taataaaatg aggaaattgc atcgcattgt ctgagtaggt      6120
gtcattctat tctgggggt ggggtggggc aggacagcaa gggggaggat tgggaagaca       6180
atagcaggca tgctggggag agatctagga accctagtg atggagttgg ccactccctc       6240
tctgcgcgct cgctcgctca ctgaggccgc ccgggcaaag cccgggcgtc gggcgacctt      6300
tggtcgcccg gcctcagtga gcgagcgagc gcgcagagag ggagtggcca accccccccc      6360
ccccccccct gcaggcgatt ctcttgtttg ctccagactc tcaggcaatg acctgatagc      6420
ctttgtagag acctctcaaa aatagctacc ctctccggca tgaatttatc agctagaacg      6480
gttgaatatc atattgatgg tgatttgact gtctccggcc tttctcaccc gtttgaatct      6540
ttacctacac attactcagg cattgcattt aaaatatatg agggttctaa aaattttat      6600 ccttgcgttg aaataaaggc ttctcccgca aaagtattac agggtcataa tgttttggt       6660 acaaccgatt tagctttatg ctctgaggct ttattgctta attttgctaa ttctttgcct      6720
tgcctgtatg atttattgga tgttggaatt cctgatgcgg tatttctcc ttacgcatct       6780 gtgcggtatt tcacaccgca tatggtgcac tctcagtaca atctgctctg atgccgcata     6840
gttaagccag ccccgacacc cgccaacacc cgctgacgcg ccctgacggg cttgtctgct      6900
cccggcatcc gcttacagac aagctgtgac cgtctccggg agctgcatgt gtcagaggtt     6960
ttcaccgtca tcaccgaaac gcgcgagacg aaagggcctc gtgatacgcc tatttttata     7020
ggttaatgtc atgataataa tggtttctta gacgtcaggt ggcacttttc ggggaaatgt     7080
gcgcggaacc cctatttgtt tatttttcta atacattca aatatgtatc cgctcatgag       7140
acaataaccc tgataaatgc ttcaataata ttgaaaaagg aagagtatga gtattcaaca     7200
tttccgtgtc gcccttattc ccttttttgc ggcattttgc cttcctgttt ttgctcaccc      7260
agaaacgctg gtgaaagtaa aagatgctga agatcagttg ggtgcacgag tgggttacat     7320
cgaactggat ctcaacagcg gtaagatcct tgagagtttt cgccccgaag aacgttttcc     7380
aatgatgagc acttttaaag ttctgctatg tggcgcggta ttatcccgta ttgacgccgg     7440
gcaagagcaa ctcggtcgcc gcatacacta ttctcagaat gacttggttg agtactcacc     7500
agtcacagaa aagcatctta cggatggcat gacagtaaga gaattatgca gtgctgccat     7560
aaccatgagt gataacactg cggccaactt acttctgaca acgatcggag gaccgaagga     7620
gctaaccgct tttttgcaca acatggggga tcatgtaact cgccttgatc gttgggaacc     7680
ggagctgaat gaagccatac caaacgacga gcgtgacacc acgatgcctg tagcaatggc      7740
aacaacgttg cgcaaactat taactggcga actacttact ctagcttccc ggcaacaatt      7800
aatagactgg atgaggcgg ataaagttgc aggaccactt ctgcgctcgg cccttccggc       7860
tggctggttt attgctgata aatctggagc cggtgagcgt gggtctcgcg gtatcattgc      7920
agcactgggg ccagatggta agccctcccg tatcgtagtt atctacacga cggggagtca      7980
ggcaactatg atgaacgaa atagacagat cgctgagata ggtgcctcac tgattaagca       8040
ttggtaactg tcagaccaag tttactcata tactttag attgatttaa aacttcattt        8100
ttaatttaaa aggatctagg tgaagatcct ttttgataat ctcatgacca aaatccctta      8160
acgtgagttt tcgttccact gagcgtcaga ccccgtagaa aagatcaaag gatcttcttg      8220
```

```
agatcctttt tttctgcgcg taatctgctg cttgcaaaca aaaaaaccac cgctaccagc    8280
ggtggtttgt ttgccggatc aagagctacc aactcttttt ccgaaggtaa ctggcttcag    8340
cagagcgcag ataccaaata ctgtccttct agtgtagccg tagttaggcc accacttcaa    8400
gaactctgta gcaccgccta catacctcgc tctgctaatc ctgttaccag tggctgctgc    8460
cagtggcgat aagtcgtgtc ttaccgggtt ggactcaaga cgatagttac cggataaggc    8520
gcagcggtcg ggctgaacgg ggggttcgtg cacacagccc agcttggagc gaacgaccta    8580
caccgaactg agatacctac agcgtgagct atgagaaagc gccacgcttc ccgaagggag    8640
aaaggcggac aggtatccgg taagcggcag ggtcggaaca ggagagcgca cgagggagct    8700
tccaggggga aacgcctggt atctttatag tcctgtcggg tttcgccacc tctgacttga    8760
gcgtcgattt ttgtgatgct cgtcaggggg cggagccta tggaaaaacg ccagcaacgc    8820
ggccttttta cggttcctgg ccttttgctg ccttttgct cacatgttct ttcctgcgtt    8880
atcccctgat tctgtggata accgtattac cgcctttgag tgagctgata ccgctcgccg    8940
cagccgaacg accgagcgca gcgagtcagt gagcgaggaa gcggaagagc gcccaatacg    9000
caaaccgcct ctccccgcgc gttggccgat tcattaatgc ag                      9042

<210> SEQ ID NO 25
<211> LENGTH: 25
<212> TYPE: DNA
<213> ORGANISM: Artificial
<220> FEATURE:
<223> OTHER INFORMATION: Primer forward

<400> SEQUENCE: 25
gacagttatc aaacagcttt ggaag                                           25

<210> SEQ ID NO 26
<211> LENGTH: 26
<212> TYPE: DNA
<213> ORGANISM: Artificial
<220> FEATURE:
<223> OTHER INFORMATION: Primer Reverse

<400> SEQUENCE: 26
gtaatctgtg ggtgtcttgt aaaaga                                          26

<210> SEQ ID NO 27
<211> LENGTH: 14069
<212> TYPE: DNA
<213> ORGANISM: Homo sapiens

<400> SEQUENCE: 27
cgttaaatgc aaacgctgct ctggctcatg tgtttgctcc gaggtatagg ttttgttcga      60
ctgacgtatc agatagtcag agtggttacc acaccgacgt tgtagcagct gcataataaa     120
tgactgaaag aatcatgtta ggcatgccca cctaacctaa cttgaatcat gcgaaagggg     180
agctgttgga attcaaatag actttctggt tcccagcagt cggcagtaat agaatgcttt     240
caggaagatg acagaatcag gagaaagatg ctgttttgca ctatcttgat ttgttacagc     300
agccaactta ttggcatgat ggagtgacag gaaaaacagc tggcatggaa gatgaaagag     360
aagatgttca aagaaaaaca ttcacaaaat gggtaaatgc acaattttct aagtttggga     420
agcagcatat tgagaacctc ttcagtgacc tacaggatgg gaggcgcctc ctagacctcc     480
tcgaaggcct gacagggcaa aaactgccaa agaaaaagg atccacaaga gttcatgccc     540
tgaacaatgt caacaaggca ctgcgggttt tgcagaacaa taatgttgat ttagtgaata     600
```

```
ttggaagtac tgacatcgta gatggaaatc ataaactgac tcttggtttg atttggaata   660
taatcctcca ctggcaggtc aaaaatgtaa tgaaaaatat catggctgga ttgcaacaaa   720
ccaacagtga aaagattctc ctgagctggg tccgacaatc aactcgtaat tatccacagg   780
ttaatgtaat caacttcacc accagctggt ctgatggcct ggctttgaat gctctcatcc   840
atagtcatag gccagaccta tttgactgga atagtgtggt ttgccagcag tcagccacac   900
aacgactgga acatgcattc aacatcgcca gatatcaatt aggcatagag aaactactcg   960
atcctgaaga tgttgatacc acctatccag ataagaagtc catcttaatg tacatcacat  1020
cactcttcca agttttgcct caacaagtga gcattgaagc catccaggaa gtggaaatgt  1080
tgccaaggcc acctaaagtg actaagaag aacattttca gttacatcat caaatgcact  1140
attctcaaca gatcacggtc agtctagcac agggatatga gagaacttct tcccctaagc  1200
ctcgattcaa gagctatgcc tacacacagg ctgcttatgt caccacctct gaccctacac  1260
ggagcccatt tccttcacag catttggaag ctcctgaaga caagtcattt ggcagttcat  1320
tgatggagag tgaagtaaac ctggaccgtt atcaaacagc tttagaagaa gtattatcgt  1380
ggcttctttc tgctgaggac acattgcaag cacaaggaga gatttctaat gatgtggaag  1440
tggtgaaaga ccagtttcat actcatgagg ggtacatgat ggatttgaca gcccatcagg  1500
gccgggttgg taatattcta caattgggaa gtaagctgat tggaacagga aaattatcag  1560
aagatgaaga aactgaagta caagagcaga tgaatctcct aaattcaaga tgggaatgcc  1620
tcagggtagc tagcatggaa aaacaaagca atttacatag agttttaatg gatctccaga  1680
atcagaaact gaaagagttg aatgactggc taacaaaaac agaagaaaga acaaggaaaa  1740
tggaggaaga gcctcttgga cctgatcttg aagacctaaa acgccaagta caacaacata  1800
aggtgcttca agaagatcta gaacaagaac aagtcagggt caattctctc actcacatgg  1860
tggtggtagt tgatgaatct agtggagatc acgcaactgc tgctttggaa gaacaactta  1920
aggtattggg agatcgatgg gcaaacatct gtagatggac agaagaccgc tgggttcttt  1980
tacaagacat ccttctcaaa tggcaacgtc ttactgaaga acagtgcctt tttagtgcat  2040
ggctttcaga aaaagaagat gcagtgaaca agattccacac aactggcttt aaagatcaaa  2100
atgaaatgtt atcaagtctt caaaaactgg ccgtttaaaa gcggatcta gaaagaaaa   2160 agcaatccat gggcaaactg tattcactca aacaagatct tctttcaaca ctgaagaata  2220
agtcagtgac ccagaagacg gaagcatggc tggataactt tgcccggtgt tgggataatt  2280
tagtccaaaa acttgaaaag agtacagcac agatttcaca ggctgtcacc accactcagc  2340
catcactaac acagacaact gtaatggaaa cagtaactac ggtgaccaca agggaacaga  2400
tcctggtaaa gcatgctcaa gaggaacttc caccaccacc tccccaaaag aagaggcaga  2460
ttactgtgga ttctgaaatt aggaaaaggt tggatgttga tataactgaa cttcacagct  2520
ggattactcg ctcagaagct gtgttgcaga gtcctgaatt tgcaatcttt cggaaggaag  2580
gcaacttctc agacttaaaa gaaaaagtca atgccataga gcgagaaaaa gctgagaagt  2640
tcagaaaact gcaagatgcc agcagatcag ctcaggccct ggtggaacag atggtgaatg  2700
agggtgttaa tgcagatagc atcaaacaag cctcagaaca actgaacagc cggtggatcg  2760
aattctgcca gttgctaagt gagagactta actggctgga gtatcagaac aacatcatcg  2820 cttttctataa tcagctacaa caattggagc agatgacaac tactgctgaa aactggttga  2880
aaatccaacc caccaccccca tcagagccaa cagcaattaa aagtcagtta aaaatttgta  2940
```

```
aggatgaagt caaccggcta tcaggtcttc aacctcaaat tgaacgatta aaaattcaaa    3000
gcatagccct gaaagagaaa ggacaaggac ccatgttcct ggatgcagac tttgtggcct    3060
ttacaaatca ttttaagcaa gtcttttctg atgtgcaggc cagagagaaa gagctacaga    3120
caattttttga cactttgcca ccaatgcgct atcaggagac catgagtgcc atcaggacat    3180
gggtccagca gtcagaaacc aaactctcca tacctcaact tagtgtcacc gactatgaaa    3240
tcatggagca gagactcggg gaattgcagg ctttacaaag ttctctgcaa gagcaacaaa    3300
gtggcctata ctatctcagc accactgtga aagagatgtc gaagaaagcg ccctctgaaa    3360
ttagccggaa atatcaatca gaatttgaag aaattgaggg acgctggaag aagctctcct    3420
cccagctggt tgagcattgt caaaagctag aggagcaaat gaataaactc cgaaaaattc    3480
agaatcacat acaaaccctg aagaaatgga tggctgaagt tgatgttttt ctgaaggagg    3540
aatggcctgc ccttggggat tcagaaattc taaaaaagca gctgaaacag tgcagacttt    3600
tagtcagtga tattcagaca attcagccca gtctaaacag tgtcaatgaa ggtgggcaga    3660
agataaagaa tgaagcagag ccagagtttg cttcgagact tgagacagaa ctcaaagaac    3720
ttaacactca gtgggatcac atgtgccaac aggtctatgc cagaaaggag gccttgaagg    3780
gaggtttgga gaaaactgta agcctccaga agatctatc agagatgcac gaatggatga    3840
cacaagctga agaagagtat cttgagagag attttgaata taaaactcca gatgaattac    3900
agaaagcagt tgaagagatg aagagagcta agaagaggcc caacaaaaa gaagcgaaag    3960
tgaaactcct tactgagtct gtaaatagtg tcatagctca agctccacct gtagcacaag    4020
aggccttaaa aaggaacttt gaaactctaa ccaccaacta ccagtggctc tgcactaggc    4080
tgaatgggaa atgcaagact ttggaagaag tttgggcatg ttggcatgag ttattgtcat    4140
acttggagaa agcaaacaag tggctaaatg aagtagaatt taaacttaaa accactgaaa    4200
acattcctgg cggagctgag gaaatctctg aggtgctaga ttcacttgaa aatttgatgc    4260
gacattcaga ggataaccca atcagattc gcatattggc acagacccta acagatggcg    4320
gagtcatgga tgagctaatc aatgaggaac ttgagacatt taattctcgt tggagggaac    4380
tacatgaaga ggctgtaagg aggcaaaagt tgcttgaaca gagcatccag tctgcccagg    4440
agactgaaaa atccttacac ttaatccagg agtccctcac attcattgac aagcagttgg    4500
cagcttatat tgcagacaag gtggacgcag ctcaaatgcc tcaggaagcc cagaaaatcc    4560
aatctgattt gacaagtcat gagatcagtt tagaagaaat gaagaaacat aatcagggga    4620
aggaggctgc ccaaagagtc ctgtctcaga ttgatgttgc acagaaaaaa ttacaagatg    4680
tctccatgaa gtttcgatta ttccagaaac cagccaattt tgagcagcgt ctacaagaaa    4740
gtaagatgat tttagatgaa gtgaagatgc acttgcctgc attggaaaca aagagtgtgg    4800
aacaggaagt agtacagtca cagctaaatc attgtgtgaa cttgtataaa agtctgagtg    4860
aagtgaagtc tgaagtggaa atggtgataa agactggacg tcagattgta cagaaaaagc    4920
agacggaaaa tcccaaagaa cttgatgaaa gagtaacagc tttgaaattg cattataatg    4980
agctgggagc aaaggtaaca gaaagaaagc aacagttgga gaaatgcttg aaattgtccc    5040
gtaagatgcg aaaggaaatg aatgtcttga cagaatggct ggcagctaca gatatggaat    5100
tgacaaagag atcagcagtt gaaggaatgc ctagtaattt ggattctgaa gttgcctggg    5160
gaaaggctac tcaaaagag attgagaac agaaggtgca cctgaagagt atcacagagg    5220
taggagaggc cttgaaaaca gttttgggca agaaggagac gttggtggaa gataaactca    5280
gtcttctgaa tagtaactgg atagctgtca cctcccgagc agaagagtgg ttaaatcttt    5340
```

```
tgttggaata ccagaaacac atggaaactt ttgaccagaa tgtggaccac atcacaaagt    5400
ggatcattca ggctgacaca cttttggatg aatcagagaa aaagaaaccc cagcaaaaag    5460
aagacgtgct taagcgttta aaggcagaac tgaatgacat acgcccaaag gtggactcta    5520
cacgtgacca agcagcaaac ttgatggcaa accgcggtga ccactgcagg aaattagtag    5580
agccccaaat ctcagagctc aaccatcgat ttgcagccat ttcacacaga attaagactg    5640
gaaaggcctc cattcctttg aaggaattgg agcagtttaa ctcagatata caaaaattgc    5700
ttgaaccact ggaggctgaa attcagcagg gggtgaatct gaaagaggaa gacttcaata    5760
aagatatgaa tgaagacaat gagggtactg taaaagaatt gttgcaaaga ggagacaact    5820
tacaacaaag aatcacagat gagagaaagc gagaggaaat aaagataaaa cagcagctgt    5880
tacagacaaa acataatgct ctcaaggatt tgaggtctca aagaagaaaa aaggctctag    5940
aaatttctca tcagtggtat cagtacaaga ggcaggctga tgatctcctg aaatgcttgg    6000
atgacattga aaaaaaatta gccagcctac ctgagcccag agatgaaagg aaaataaagg    6060
aaattgatcg ggaattgcag aagaagaaag aggagctgaa tgcagtgcgt aggcaagctg    6120
agggcttgtc tgaggatggg gccgcaatgg cagtggagcc aactcagatc cagctcagca    6180
agcgctggcg ggaaattgag agcaaatttg ctcagtttcg aagactcaac tttgcacaaa    6240
ttcacactgt ccgtgaagaa acgatgatgg tgatgactga agacatgcct ttggaaattt    6300
cttatgtgcc ttctacttat ttgactgaaa tcactcatgt ctcacaagcc ctattagaag    6360
tggaacaact tctcaatgct cctgacctct gtgctaagga cttgaagat ctctttaagc    6420 aagaggagtc tctgaagaat ataaaagata gtctacaaca aagctcaggt cggattgaca    6480
ttattcatag caagaagaca gcagcattgc aaagtgcaac gcctgtggaa agggtgaagc    6540
tacaggaagc tctctcccag cttgatttcc aatgggaaaa agttaacaaa atgtacaagg    6600
accgacaagg gcgatttgac agatctgttg agaaatggcg gcgttttcat tatgatataa    6660
agatatttaa tcagtggcta acagaagctg aacagtttct cagaaagaca caaattcctg    6720
agaattggga acatgctaaa tacaaatggt atcttaagga actccaggat ggcattgggc    6780
agcggcaaac tgttgtcaga acattgaatg caactggggga agaaataatt cagcaatcct    6840
caaaaacaga tgccagtatt ctacaggaaa aattgggaag cctgaatctg cggtggcagg    6900
aggtctgcaa acagctgtca gacagaaaaa agaggctaga agaacaaaag aatatcttgt    6960
cagaatttca aagagattta aatgaatttg ttttatggtt ggaggaagca gataacattg    7020
ctagtatccc acttgaacct ggaaaagagc agcaactaaa agaaaagctt gagcaagtca    7080
agttactggt ggaagagttg cccctgcgcc agggaattct caaacaatta aatgaaactg    7140
gaggacccgt gcttgtaagt gctcccataa gcccagaaga gcaagataaa cttgaaaata    7200
agctcaagca gacaaatctc cagtggataa aggtttccag agctttacct gagaaacaag    7260
gagaaattga agctcaaata aaagaccttg ggcagcttga aaaaaagctt gaagaccttg    7320
aagagcagtt aaatcatctg ctgctgtggt tatctcctat taggaatcag ttggaaattt    7380
ataaccaacc aaaccaagaa ggaccatttg acgttcagga aactgaaata gcagttcaag    7440
ctaaacaacc ggatgtggaa gagattttgt ctaaagggca gcatttgtac aaggaaaaac    7500
cagccactca gccagtgaag aggaagttag aagatctgag ctctgagtgg aaggcggtaa    7560
accgtttact tcaagagctg agggcaaagc agcctgacct agctcctgga ctgaccacta    7620
ttggagcctc tcctactcag actgttactc tggtgacaca acctgtggtt actaaggaaa    7680
```

```
ctgccatctc caaactagaa atgccatctt ccttgatgtt ggaggtacct gctctggcag    7740
atttcaaccg ggcttggaca gaacttaccg actggctttc tctgcttgat caagttataa    7800
aatcacagag ggtgatggtg ggtgaccttg aggatatcaa cgagatgatc atcaagcaga    7860
aggcaacaat gcaggatttg aacagaggc gtccccagtt ggaagaactc attaccgctg     7920
cccaaaattt gaaaacaag accagcaatc aagaggctag aacaatcatt acggatcgaa     7980
ttgaaagaat tcagaatcag tgggatgaag tacaagaaca ccttcagaac cggaggcaac    8040
agttgaatga aatgttaaag gattcaacac aatggctgga agctaaggaa gaagctgagc    8100
aggtcttagg acaggccaga gccaagcttg agtcatggaa ggagggtccc tatacagtag    8160
atgcaatcca aaagaaaatc acagaaacca agcagttggc caaagacctc cgccagtggc    8220
agacaaatgt agatgtggca aatgacttgg ccctgaaact tctccgggat tattctgcag    8280
atgataccag aaaagtccac atgataacag agaatatcaa tgcctcttgg agaagcattc    8340
ataaaagggt gagtgagcga gaggctgctt tggaagaaac tcatagatta ctgcaacagt    8400 tcccccctgga cctgaaaaag tttcttgcct ggcttacaga agctgaaaca actgccaatg   8460
tcctacagga tgctacccgt aaggaaaggc tcctagaaga ctccaaggga gtaaaagagc    8520
tgatgaaaca atggcaagac ctccaaggtg aaattgaagc tcacacagat gtttatcaca    8580
acctggatga aaacagccaa aaaatcctga gatccctgga aggttccgat gatgcagtcc    8640
tgttacaaag acgtttggat aacatgaact caagtggag tgaacttcgg aaaaagtctc      8700
tcaacattag gtcccatttg gaagccagtt ctgaccagtg gaagcgtctg cacctttctc    8760
tgcaggaact tctggtgtgg ctacagctga aagatgatga attaagccgg caggcaccta    8820
ttggaggcga ctttccagca gttcagaagc agaacgatgt acatagggcc ttcaagaggg    8880
aattgaaaac taaagaacct gtaatcatga gtactcttga gactgtacga atatttctga    8940
cagagcagcc tttggaagga ctagagaaac tctaccagga gcccagagag ctgcctcctg    9000
aggagagagc ccagaatgtc actcggcttc tacgaaagca ggctgaggag gtcaatactg    9060
agtgggaaaa attgaacctg cactccgctg actggcagag aaaaatagat gagacccttg    9120
aaagactcca ggaacttcaa gaggccacgg atgagctgga cctcaagctg cgccaagctg    9180
aggtgatcaa gggatcctgg cagcccgtgg gcgatctcct cattgactct ctccaagatc    9240
acctcgagaa agtcaaggca cttcgaggag aaattgcgcc tctgaaagag aacgtgagcc    9300
acgtcaatga ccttgctcgc cagcttacca ctttgggcat tcagctctca ccgtataacc    9360
tcagcactct ggaagacctg aacaccagat ggaagcttct gcaggtggcc gtcgaggacc    9420
gagtcaggca gctgcatgaa gcccacaggg actttggtcc agcatctcag cactttcttt    9480
ccacgtctgt ccagggtccc tgggagagag ccatctcgcc aaacaaagtg ccctactata    9540
tcaaccacga gactcaaaca acttgctggg accatcccaa aatgacagag ctctaccagt    9600
ctttagctga cctgaataat gtcagattct cagcttatag gactgccatg aaactccgaa    9660
gactgcagaa ggcccctttgc ttggatctct tgagcctgtc agctgcatgt gatgccttgg   9720
accagcacaa cctcaagcaa aatgaccagc ccatggatat cctgcagatt attaattgtt    9780
tgaccactat ttatgaccgc ctggagcaag agcacaacaa tttggtcaac gtccctctct    9840
gcgtggatat gtgtctgaac tggctgctga atgtttatga tacgggacga acagggagga    9900
tccgtgtcct gtcttttaaa actggcatca tttccctgtg taaagcacat ttggaagaca    9960
agtacagata ccttttcaag caagtggcaa gttcaacagg attttgtgac cagcgcaggc    10020
tgggcctcct tctgcatgat tctatccaaa ttccaagaca gttgggtgaa gttgcatcct    10080
```

```
ttgggggcag taacattgag ccaagtgtcc ggagctgctt ccaatttgct aataataagc    10140
cagagatcga agcggccctc ttcctagact ggatgagact ggaacccag tccatggtgt     10200 ggctgcccgt cctgcacaga gtggctgctg cagaaactgc aagcatcag gccaaatgta     10260 acatctgcaa agagtgtcca atcattggat tcaggtacag gagtctaaag cactttaatt    10320
atgacatctg ccaaagctgc ttttttctg gtcgagttgc aaaaggccat aaaatgcact     10380
atcccatggt ggaatattgc actccgacta catcaggaga gatgttcga gactttgcca    10440 aggtactaaa aaacaaattt cgaaccaaaa ggtattttgc gaagcatccc cgaatgggct    10500
acctgccagt gcagactgtc ttagagggg acaacatgga aactcccgtt actctgatca    10560
acttctggcc agtagattct gcgcctgcct cgtcccctca gctttcacac gatgatactc    10620
attcacgcat tgaacattat gctagcaggc tagcagaaat ggaaaacagc aatggatctt    10680
atctaaatga tagcatctct cctaatgaga gcatagatga tgaacatttg ttaatccagc    10740
attactgcca aagtttgaac caggactccc ccctgagcca gcctcgtagt cctgcccaga    10800
tcttgatttc cttagagagt gaggaaagag gggagctaga gagaatccta gcagatcttg    10860
aggaagaaaa caggaatctg caagcagaat atgaccgtct aaagcagcag cacgaacata    10920
aaggcctgtc cccactgccg tcccctcctg aaatgatgcc cacctctccc cagagtcccc    10980
gggatgctga gctcattgct gaggccaagc tactgcgtca acacaaaggc cgcctggaag    11040
ccaggatgca aatcctggaa gaccacaata aacagctgga gtcacagtta cacaggctaa    11100
ggcagctgct ggagcaaccc caggcagagg ccaaagtgaa tggcacaacg gtgtcctctc    11160
cttctacctc tctacagagg tccgacagca gtcagcctat gctgctccga gtggttggca    11220
gtcaaacttc ggactccatg ggtgaggaag atcttctcag tcctccccag gacacaagca    11280
cagggttaga ggaggtgatg gagcaactca acaactcctt ccctagttca agaggaagaa    11340 ataccctgg aaagccaatg agagaggaca caatgtagga agtctttcc acatggcaga     11400 tgatttgggc agagcgatgg agtccttagt atcagtcatg acagatgaag aaggagcaga    11460
ataaatgttt tacaactcct gattcccgca tggttttat aatattcata caacaaagag    11520
gattagacag taagagttta caagaaataa atctatattt ttgtgaaggg tagtggtatt    11580
atactgtaga tttcagtagt ttctaagtct gttattgttt tgttaacaat ggcaggtttt    11640
acacgtctat gcaattgtac aaaaaagtta taagaaaact acatgtaaaa tcttgatagc    11700
taaataactt gccatttctt tatatggaac gcattttggg ttgtttaaaa atttataaca    11760
gttataaaga aagattgtaa actaaagtgt gctttataaa aaaagttgt ttataaaaac     11820 ccctaaaaac aaaacaaaca cacacacaca cacatacaca cacacacaca aaactttgag    11880
gcagcgcatt gttttgcatc cttttggcgt gatatccata tgaaattcat ggcttttct     11940 ttttttgcat attaaagata agacttcctc taccaccaca ccaaatgact actacacact    12000
gctcatttga gaactgtcag ctgagtgggg caggcttgag ttttcatttc atatatctat    12060
atgtctataa gtatataaat actatagtta tatagataaa gagatacgaa tttctataga    12120 ctgactttt ccattttta aatgttcatg tcacatccta atagaaagaa attacttcta      12180
gtcagtcatc caggcttacc tgcttggtct agaatggatt tttcccggag ccggaagcca    12240
ggaggaaact acaccacact aaaacattgt ctacagctcc agatgtttct cattttaaac    12300
aactttccac tgcaacgaa agtaaagtaa agtattggat ttttttaaag ggaacatgtg     12360
aatgaataca caggacttat tatatcagag tgagtaatcg gttggttggt tgattgattg    12420
```

| | | |
|---|---|---|
| attgattgat acattcagct tcctgctgct agcaatgcca cgatttagat ttaatgatgc | 12480 |
| ttcagtggaa atcaatcaga aggtattctg accttgtgaa catcagaagg tatttttaa | 12540 |
| ctcccaagca gtagcaggac gatgataggg ctggagggct atggattccc agcccatccc | 12600 |
| tgtgaaggag taggccactc tttaagtgaa ggattggatg attgttcata atacataaag | 12660 |
| ttctctgtaa ttacaactaa attattatgc cctcttctca cagtcaaaag gaactgggtg | 12720 |
| gtttggtttt tgttgctttt ttagatttat tgtcccatgt gggatgagtt tttaaatgcc | 12780 |
| acaagacata atttaaaata aataaacttt gggaaaaggt gtaaacagt agccccatca | 12840 |
| catttgtgat actgacaggt atcaacccag aagcccatga actgtgtttc catcctttgc | 12900 |
| atttctctgc gagtagttcc acacaggttt gtaagtaagt aagaaagaag gcaaattgat | 12960 |
| tcaaatgtta caaaaaaacc cttcttggtg gattagacag gttaaatata taaacaaaca | 13020 |
| aacaaaaatt gctcaaaaaa gaggagaaaa gctcaagagg aaaagctaag gactggtagg | 13080 |
| aaaaagcttt actctttcat gccattttat ttcttttga ttttaaatc attcattcaa | 13140 |
| tagataccac cgtgtgacct ataattttgc aaatctgtta cctctgacat caagtgtaat | 13200 |
| tagcttttgg agagtgggct gacatcaagt gtaattagct tttggagagt gggttttgtc | 13260 |
| cattattaat aattaattaa ttaacatcaa acacggcttc tcatgctatt tctacctcac | 13320 |
| tttggttttg gggtgttcct gataattgtg cacacctgag ttcacagctt caccacttgt | 13380 |
| ccattgcgtt attttctttt tcctttataa ttctttcttt ttccttcata attttcaaaa | 13440 |
| gaaaacccaa agctctaagg taacaaatta ccaaattaca tgaagatttg gttttgtct | 13500 |
| tgcattttt tcctttatgt gacgctggac cttttcttta cccaaggatt tttaaaactc | 13560 |
| agatttaaaa caaggggtta ctttacatcc tactaagaag tttaagtaag taagtttcat | 13620 |
| tctaaaatca gaggtaaata gagtgcataa ataattttgt tttaatcttt ttgtttttct | 13680 |
| tttagacaca ttagctctgg agtgagtctg tcataatatt tgaacaaaaa ttgagagctt | 13740 |
| tattgctgca ttttaagcat aattaatttg gacattattt cgtgttgtgt tctttataac | 13800 |
| caccaagtat taaactgtaa atcataatgt aactgaagca taaacatcac atggcatgtt | 13860 |
| ttgtcattgt tttcaggtac tgagttctta cttgagtatc ataatatatt gtgttttaac | 13920 |
| accaacactg taacatttac gaattatttt tttaaacttc agttttactg cattttcaca | 13980 |
| acatatcaga cttcaccaaa tatatgcctt actattgtat tatagtactg ctttactgtg | 14040 |
| tatctcaata aagcacgcag ttatgttac | 14069 |

```
<210> SEQ ID NO 28
<211> LENGTH: 17
<212> TYPE: DNA
<213> ORGANISM: Homo sapiens

<400> SEQUENCE: 28
agcttgagca agtcaag                                                  17

<210> SEQ ID NO 29
<211> LENGTH: 30
<212> TYPE: DNA
<213> ORGANISM: Homo sapiens

<400> SEQUENCE: 29
caactaaaag aaaagcttga gcaagtcaag                                    30

<210> SEQ ID NO 30
<211> LENGTH: 38
```

```
<212> TYPE: DNA
<213> ORGANISM: Homo sapiens

<400> SEQUENCE: 30
aaaataagct caagcagaca aatctccagt ggataaag                               38

<210> SEQ ID NO 31
<211> LENGTH: 14
<212> TYPE: DNA
<213> ORGANISM: Homo sapiens

<400> SEQUENCE: 31
catttgacgt tcag                                                        14

<210> SEQ ID NO 32
<211> LENGTH: 93
<212> TYPE: DNA
<213> ORGANISM: Homo sapiens

<400> SEQUENCE: 32
cagttaaatc atctgctgct gtggttatct cctattagga atcagttgga aatttataac      60
caaccaaacc aagaaggacc atttgacgtt cag                                   93

<210> SEQ ID NO 33
<211> LENGTH: 53
<212> TYPE: DNA
<213> ORGANISM: Homo sapiens

<400> SEQUENCE: 33
tgtctaaagg gcagcatttg tacaaggaaa aaccagccac tcagccagtg aag             53

<210> SEQ ID NO 34
<211> LENGTH: 22
<212> TYPE: DNA
<213> ORGANISM: Homo sapiens

<400> SEQUENCE: 34
ggactgacca ctattggagc ct                                               22

<210> SEQ ID NO 35
<211> LENGTH: 71
<212> TYPE: DNA
<213> ORGANISM: Homo sapiens

<400> SEQUENCE: 35
ttactaagga aactgccatc tccaaactag aaatgccatc ttccttgatg ttggaggtac      60
ctgctctggc a                                                           71

<210> SEQ ID NO 36
<211> LENGTH: 74
<212> TYPE: DNA
<213> ORGANISM: Homo sapiens

<400> SEQUENCE: 36
gcaacaatgc aggatttgga acagaggcgt ccccagttgg aagaactcat taccgctgcc      60
caaaatttga aaaa                                                        74

<210> SEQ ID NO 37
<211> LENGTH: 28
<212> TYPE: DNA
<213> ORGANISM: Homo sapiens
```

<400> SEQUENCE: 37
caagaccagc aatcaagagg ctagaaca                                    28

<210> SEQ ID NO 38
<211> LENGTH: 22
<212> TYPE: DNA
<213> ORGANISM: Artificial sequence
<220> FEATURE:
<223> OTHER INFORMATION: PCR primer

<400> SEQUENCE: 38
tcttgcagcc taaaggaaca aa                                          22

<210> SEQ ID NO 39
<211> LENGTH: 22
<212> TYPE: DNA
<213> ORGANISM: Artificial sequence
<220> FEATURE:
<223> OTHER INFORMATION: PCR primer

<400> SEQUENCE: 39
tcctctcgct ttctctcatc tg                                          22

<210> SEQ ID NO 40
<211> LENGTH: 22
<212> TYPE: DNA
<213> ORGANISM: Artificial sequence
<220> FEATURE:
<223> OTHER INFORMATION: PCR primer

<400> SEQUENCE: 40
gaacaggtgg tattactagc ca                                          22

<210> SEQ ID NO 41
<211> LENGTH: 22
<212> TYPE: DNA
<213> ORGANISM: Artificial sequence
<220> FEATURE:
<223> OTHER INFORMATION: PCR primer

<400> SEQUENCE: 41
ggttgcagtg agctgagatc at                                          22

<210> SEQ ID NO 42
<211> LENGTH: 24
<212> TYPE: DNA
<213> ORGANISM: Artificial sequence
<220> FEATURE:
<223> OTHER INFORMATION: PCR primer

<400> SEQUENCE: 42
gcagagctag agaagaatga gaaa                                        24

<210> SEQ ID NO 43
<211> LENGTH: 24
<212> TYPE: DNA
<213> ORGANISM: Artificial sequence
<220> FEATURE:
<223> OTHER INFORMATION: PCR primer

<400> SEQUENCE: 43
tttgttattg gttgaggttt gctg                                        24

<210> SEQ ID NO 44
<211> LENGTH: 354

<212> TYPE: PRT
<213> ORGANISM: artificial sequence
<220> FEATURE:
<223> OTHER INFORMATION: DMD21 2874

<400> SEQUENCE: 44

```
Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Ser Tyr Lys Phe Lys His Gln Leu Glu Leu Thr Phe Thr Val Gly Gln
        35                  40                  45

Lys Thr Gln Arg Arg Trp Phe Leu Asp Lys Leu Val Asp Glu Ile Gly
    50                  55                  60

Val Gly Tyr Val Thr Asp Ser Gly Ser Met Ser Ala Tyr Arg Leu Ser
65                  70                  75                  80

Lys Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Asn Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Arg Pro Asn Gln Ser Ala
210                 215                 220

Lys Phe Lys His Tyr Leu Gln Leu Thr Phe Gln Val Thr Gln Lys Thr
225                 230                 235                 240

Gln Arg Arg Trp Phe Leu Asp Lys Leu Val Asp Arg Ile Gly Val Gly
                245                 250                 255

Tyr Val Arg Asp Ser Gly Ser Val Ser Asp Tyr Lys Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 45
<211> LENGTH: 354
<212> TYPE: PRT

<213> ORGANISM: artificial sequence
<220> FEATURE:
<223> OTHER INFORMATION: DMD21 3387

<400> SEQUENCE: 45

```
Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Arg Gln
                20                  25                  30

Ser Tyr Lys Phe Lys His Gln Leu Glu Leu Thr Phe Thr Val Gly Gln
            35                  40                  45

Lys Thr Gln Arg Arg Trp Phe Leu Asp Lys Leu Val Asp Glu Ile Gly
50                  55                  60

Val Gly Tyr Val Thr Asp Ser Gly Ser Met Ser Ala Tyr Arg Leu Ser
65                  70                  75                  80

Lys Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Asn Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Arg Pro Asn Gln Ser Ala
210                 215                 220

Lys Phe Lys His Tyr Leu Gln Leu Thr Phe Gln Val Thr Gln Lys Thr
225                 230                 235                 240

Gln Arg Arg Trp Phe Leu Asp Lys Leu Val Asp Arg Ile Gly Val Gly
                245                 250                 255

His Val Arg Asp Ser Gly Ser Val Ser Asp Tyr Lys Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 46
<211> LENGTH: 354
<212> TYPE: PRT
<213> ORGANISM: artificial sequence

<220> FEATURE:
<223> OTHER INFORMATION: DMD31 3631

<400> SEQUENCE: 46

Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro His Gln
            20                  25                  30

Thr Cys Lys Phe Lys His Arg Leu Ser Leu Thr Phe Ala Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Tyr Tyr Thr Leu Ser
65                  70                  75                  80

Lys Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Gln Ser Arg
210                 215                 220

Lys Phe Lys His Gln Leu Glu Leu Thr Phe Leu Val Thr Gln Lys Thr
225                 230                 235                 240

Gln Arg Arg Trp Phe Leu Asp Lys Leu Ala Asp Arg Val Gly Val Gly
                245                 250                 255

Tyr Val Arg Asp Ala Gly Ser Val Ser Asn Tyr Arg Leu Ser Lys Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Ala
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Gly Glu Lys Lys Lys Ser
            340                 345                 350

Ser Pro

<210> SEQ ID NO 47
<211> LENGTH: 354
<212> TYPE: PRT
<213> ORGANISM: artificial sequence
<220> FEATURE:

<223> OTHER INFORMATION: DMD31 3633

<400> SEQUENCE: 47

```
Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro His Gln
            20                  25                  30

Thr Cys Lys Phe Lys His Arg Leu Ser Leu Thr Phe Ala Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Tyr Tyr Thr Leu Ser
65                  70                  75                  80

Lys Ile Lys Pro Leu His Asn Phe Leu Thr Gln Leu Gln Pro Phe Leu
                85                  90                  95

Glu Leu Lys Gln Lys Gln Ala Asn Leu Ala Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Gln Ser Arg
210                 215                 220

Lys Phe Lys His Gln Leu Glu Leu Thr Phe Leu Val Thr Gln Lys Thr
225                 230                 235                 240

Gln Arg Arg Trp Phe Leu Asp Lys Leu Ala Asp Arg Val Gly Val Gly
                245                 250                 255

Tyr Val Arg Asp Ala Gly Ser Val Ser Asn Tyr Arg Leu Ser Lys Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Ala
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Gly Glu Lys Lys Lys Ser
            340                 345                 350

Ser Pro
```

<210> SEQ ID NO 48
<211> LENGTH: 354
<212> TYPE: PRT
<213> ORGANISM: artificial sequence
<220> FEATURE:
<223> OTHER INFORMATION: DMD33 3326

<400> SEQUENCE: 48

```
Met Ala Asn Thr Lys Tyr Asn Glu Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Ala Asn Lys Phe Lys His Gln Leu Glu Leu Thr Phe Thr Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Lys Tyr Gln Leu Ser
65                  70                  75                  80

Lys Ile Lys Pro Leu His Asn Phe Leu Thr Gln Leu Gln Pro Phe Leu
                85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Ser Asp Gly Ser Ile Ile Ala Gln Ile Lys Pro Asn Gln Gly His
    210                 215                 220

Lys Phe Lys His Gln Leu Ser Leu Thr Phe Lys Val Thr Gln Lys Thr
225                 230                 235                 240

Gln Arg Arg Trp Phe Leu Asp Lys Leu Val Asp Arg Ile Gly Val Gly
                245                 250                 255

Tyr Val Tyr Asp Ser Gly Ser Val Ser Tyr Tyr Asn Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

```
<210> SEQ ID NO 49
<211> LENGTH: 354
<212> TYPE: PRT
<213> ORGANISM: artificial sequence
<220> FEATURE:
<223> OTHER INFORMATION: DMD33 3330
```

<400> SEQUENCE: 49

```
Met Ala Asn Thr Lys Tyr Asn Glu Glu Phe Leu Leu Tyr Leu Ala Gly
1               5                   10                  15

Phe Val Asp Ser Asp Gly Ser Ile Ile Ala Gln Ile Lys Pro Arg Gln
            20                  25                  30

Ala Asn Lys Phe Lys His Gln Leu Glu Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Arg Tyr Thr Leu Ser
65                  70                  75                  80

Lys Ile Lys Pro Leu His Asn Phe Leu Thr Gln Leu Gln Pro Phe Leu
            85                  90                  95

Glu Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Gly Gly Ser Asp Lys Tyr Asn Gln Ala Leu
                165                 170                 175

Ser Lys Tyr Asn Gln Ala Leu Ser Lys Tyr Asn Gln Ala Leu Ser Gly
            180                 185                 190

Gly Gly Gly Ser Asn Lys Lys Phe Leu Leu Tyr Leu Ala Gly Phe Val
        195                 200                 205

Asp Gly Asp Gly Ser Ile Ile Ala Gln Ile Lys Pro Asn Gln Gly His
    210                 215                 220

Lys Phe Lys His Gln Leu Ser Leu Thr Phe Lys Val Thr Gln Lys Thr
225                 230                 235                 240

Gln Arg Arg Trp Phe Leu Asp Lys Leu Val Asp Arg Ile Gly Val Gly
                245                 250                 255

Tyr Val Tyr Asp Ser Gly Ser Val Ser Asp Tyr Lys Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Val Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 50
<211> LENGTH: 24
<212> TYPE: DNA
<213> ORGANISM: Artificial sequence
<220> FEATURE:
<223> OTHER INFORMATION: DMD31 target sequence

<400> SEQUENCE: 50

<210> SEQ ID NO 51
<211> LENGTH: 24
<212> TYPE: DNA
<213> ORGANISM: Artificial sequence
<220> FEATURE:
<223> OTHER INFORMATION: DMD31 target sequence

<400> SEQUENCE: 51
aatgtctgat gttcaatgtg ttga                                          24

<210> SEQ ID NO 52
<211> LENGTH: 24
<212> TYPE: DNA
<213> ORGANISM: Artificial sequence
<220> FEATURE:
<223> OTHER INFORMATION: DMD33 target sequence

<400> SEQUENCE: 52
aaatcctgcc ttaaagtatc tcat                                          24

<210> SEQ ID NO 53
<211> LENGTH: 6233
<212> TYPE: DNA
<213> ORGANISM: Artificial sequence
<220> FEATURE:
<223> OTHER INFORMATION: pCLS2874

<400> SEQUENCE: 53
taactcgagc gctagcaccc agctttcttg tacaaagtgg tgatctagag ggcccgcggt      60
tcgaaggtaa gcctatccct aaccctctcc tcggtctcga ttctacgcgt accggttagt     120
aatgagttta acggggggag gctaactgaa acacggaagg agacaatacc ggaaggaacc     180
cgcgctatga cggcaataaa aagacagaat aaaacgcacg ggtgttgggt cgtttgttca     240
taaacgcggg gttcggtccc agggctggca ctctgtcgat accccaccga dacccccattg    300 gggccaatac gcccgcgttt cttccttttc cccaccccac cccccaagtt cgggtgaagg     360
cccagggctc gcagccaacg tcggggcggc aggccctgcc atagcagatc tgcgcagctg     420
gggctctagg gggtatcccc acgcgccctg tagcggcgca ttaagcgcgg cgggtgtggt     480
ggttacgcgc agcgtgaccg ctacacttgc cagcgcccta gcgcccgctc ctttcgcttt     540
cttcccttcc tttctcgcca cgttcgccgg ctttccccgt caagctctaa atcggggcat     600
ccctttaggg ttccgattta gtgctttacg gcacctcgac cccaaaaaac ttgattaggg     660
tgatggttca cgtagtgggc catcgccctg atagacggtt tttcgccctt tgacgttgga     720
gtccacgttc tttaatagtg gactcttgtt ccaaactgga acaacactca acctatctc      780 ggtctattct tttgatttat aagggatttt ggggatttcg gcctattggt taaaaaatga     840
gctgatttaa caaaaattta acgcgaatta attctgtgga atgtgtgtca gttagggtgt     900
ggaaagtccc caggctcccc agcaggcaga agtatgcaaa gcatgcatct caattagtca     960
gcaaccaggt gtggaaagtc cccaggctcc ccagcaggca gaagtatgca aagcatgcat    1020
ctcaattagt cagcaaccat agtcccgccc ctaactccgc ccatcccgcc ctaactccg     1080 cccagttccg cccattctcc gccccatggc tgactaattt ttttttattta tgcagaggcc    1140 gaggccgcct ctgcctctga gctattccag aagtagtgag gaggcttttt tggaggccta    1200
ggcttttgca aaaagctccc gggagcttgt atatccattt tcggatctga tcagcacgtg    1260

```
ttgacaatta atcatcggca tagtatatcg gcatagtata atacgacaag gtgaggaact    1320
aaaccatggc caagcctttg tctcaagaag aatccaccct cattgaaaga gcaacggcta    1380
caatcaacag catccccatc tctgaagact acagcgtcgc cagcgcagct ctctctagcg    1440
acggccgcat cttcactggt gtcaatgtat atcattttac tggggggacct tgtgcagaac   1500
tcgtggtgct gggcactgct gctgctgcgg cagctggcaa cctgacttgt atcgtcgcga    1560
tcggaaatga aacagggggc atcttgagcc cctgcggacg gtgccgacag gtgcttctcg    1620
atctgcatcc tgggatcaaa gccatagtga aggacagtga tggacagccg acggcagttg    1680
ggattcgtga attgctgccc tctggttatg tgtgggaggg ctaagcactt cgtgccgag     1740
gagcaggact gacacgtgct acgagatttc gattccaccg ccgccttcta tgaaaggttg    1800
ggcttcggaa tcgttttccg ggacgccggc tggatgatcc tccagcgcgg ggatctcatg    1860
ctggagttct tcgcccaccc caacttgttt attgcagctt ataatggtta caaataaagc    1920
aatagcatca caaatttcac aaataaagca tttttttcac tgcattctag ttgtggtttg    1980
tccaaactca tcaatgtatc ttatcatgtc tgtataccgt cgacctctag ctagagcttg    2040
gcgtaatcat ggtcatagct gtttcctgtg tgaaattgtt atccgctcac aattccacac    2100
aacatacgag ccggaagcat aaagtgtaaa gcctggggtg cctaatgagt gagctaactc    2160
acattaattg cgttgcgctc actgcccgct ttccagtcgg gaaacctgtc gtgccagctg    2220
cattaatgaa tcggccaacg cgcggggaga ggcggtttgc gtattgggcg ctcttccgct    2280
tcctcgctca ctgactcgct gcgctcggtc gttcggctgc ggcgagcggt atcagctcac    2340
tcaaaggcgg taatacggtt atccacagaa tcaggggata acgcaggaaa gaacatgtga    2400
gcaaaaggcc agcaaaaggc caggaaccgt aaaaaggccg cgttgctggc gttttttccat   2460
aggctccgcc ccctgacga gcatcacaaa aatcgacgct caagtcagag gtggcgaaac     2520
ccgacaggac tataaagata ccaggcgttt ccccctggaa gctccctcgt gcgctctcct    2580
gttccgaccc tgccgcttac cggatacctg tccgcctttc tcccttcggg aagcgtggcg    2640
ctttctcata gctcacgctg taggtatctc agttcggtgt aggtcgttcg ctccaagctg    2700
ggctgtgtgc acgaaccccc cgttcagccc gaccgctgcg ccttatccgg taactatcgt    2760
cttgagtcca acccggtaag acacgactta tcgccactgg cagcagccac tggtaacagg    2820
attagcagag cgaggtatgt aggcggtgct acagagttct tgaagtggtg cctaactac     2880
ggctacacta gaagaacagt atttggtatc tgcgctctgc tgaagccagt taccttcgga    2940
aaaagagttg gtagctcttg atccggcaaa caaaccaccg ctggtagcgg tttttttgtt    3000
tgcaagcagc agattacgcg cagaaaaaaa ggatctcaag aagatccttt gatcttttct    3060
acggggtctg acgctcagtg gaacgaaaac tcacgttaag ggattttggt catgagatta    3120
tcaaaaagga tcttcaccta gatcctttta aattaaaaat gaagttttaa atcaatctaa    3180
agtatatatg agtaaacttg gtctgacagt taccaatgct taatcagtga ggcacctatc    3240
tcagcgatct gtctatttcg ttcatccata gttgcctgac tccccgtcgt gtagataact    3300
acgatacggg agggcttacc atctggcccc agtgctgcaa tgataccgcg agacccacgc    3360
tcaccggctc cagatttatc agcaataaac cagccagccg gaagggccga gcgcagaagt    3420
ggtcctgcaa ctttatccgc ctccatccag tctattaatt gttgccggga agctagagta    3480
agtagttcgc cagttaatag tttgcgcaac gttgttgcca ttgctacagg catcgtggtg    3540
tcacgctcgt cgtttggtat ggcttcattc agctccggtt cccaacgatc aaggcgagtt    3600
acatgatccc ccatgttgtg caaaaaagcg gttagctcct tcggtcctcc gatcgttgtc    3660
```

```
agaagtaagt tggccgcagt gttatcactc atggttatgg cagcactgca taattctctt    3720
actgtcatgc catccgtaag atgctttttct gtgactggtg agtactcaac caagtcattc   3780
tgagaatagt gtatgcggcg accgagttgc tcttgcccgg cgtcaatacg ggataatacc    3840
gcgccacata gcagaacttt aaaagtgctc atcattggaa aacgttcttc ggggcgaaaa    3900
ctctcaagga tcttaccgct gttgagatcc agttcgatgt aacccactcg tgcacccaac    3960
tgatcttcag catcttttac tttcaccagc gtttctgggt gagcaaaaac aggaaggcaa    4020
aatgccgcaa aaagggaat aagggcgaca cggaaatgtt gaatactcat actcttcctt     4080
tttcaatatt attgaagcat ttatcagggt tattgtctca tgagcggata catatttgaa    4140
tgtatttaga aaataaaca aatagggggtt ccgcgcacat ttccccgaaa agtgccacct    4200
gacgtcgacg gatcgggaga tctcccgatc ccctatggtg cactctcagt acaatctgct    4260
ctgatgccgc atagttaagc cagtatctgc tccctgcttg tgtgttggag gtcgctgagt    4320
agtgcgcgag caaaatttaa gctacaacaa ggcaaggctt gaccgacaat tgcatgaaga    4380
atctgcttag ggttaggcgt tttgcgctgc ttcgcgatgt acgggccaga tatacgcgtt    4440
gacattgatt attgactagt tattaatagt aatcaattac ggggtcatta gttcatagcc    4500
catatatgga gttccgcgtt acataactta cggtaaatgg cccgcctggc tgaccgccca    4560
acgaccccg cccattgacg tcaataatga cgtatgttcc catagtaacg ccaatagga     4620
cttttccattg acgtcaatgg gtggagtatt tacggtaaac tgcccacttg gcagtacatc   4680
aagtgtatca tatgccaagt acgccccccta ttgacgtcaa tgacggtaaa tggcccgcct   4740
ggcattatgc ccagtacatg accttatggg actttcctac ttggcagtac atctacgtat    4800
tagtcatcgc tattaccatg gtgatgcggt tttggcagta catcaatggg cgtggatagc    4860
ggtttgactc acggggattt ccaagtctcc accccattga cgtcaatggg agtttgtttt    4920
ggcaccaaaa tcaacgggac tttccaaaat gtcgtaacaa ctccgcccca ttgacgcaaa    4980
tgggcggtag gcgtgtacgg tgggaggtct atataagcag agctctctgg ctaactagag    5040
aacccactgc ttactggctt atcgaaatga attcgactca ctgttgggag acccaagctg    5100
gctagttaag ctatcacaag tttgtacaaa aaagcaggct ggcgcgccta cacagcggcc    5160
ttgccaccat ggccaatacc aaatataacg aagagttcct gctgtacctg gccggctttg    5220
tggacggtga cggtagcatc atcgctcaga ttaaaccacg tcagtcttat aagtttaaac    5280
atcagctaga attgaccttt accgtgggtc aaaagaccca gcgccgttgg tttctggaca    5340
aactagtgga tgaaattggc gttggttacg taaccgattc cggtagcatg tccgcatacc    5400
gtttaagcaa aatcaagccg ctgcacaact tcctgactca actgcagccg tttctggaac    5460
tgaaacagaa acaggcaaac ctggttctga aaattatcga acagctgccg tctgcaaaag    5520
aatccccgga caaattcctg gaagtttgta cctgggtgga tcaggtggca gctctgaacg    5580
attctaagac gcgtaaaacc acttctgaaa ccgttcgtgc tgtgctggac aacctgagcg    5640
agaagaagaa atcctccccg gcggccggtg gatctgataa gtataatcag gctctgtcta    5700
aatacaacca agcactgtcc aagtacaatc aggccctgtc tggtggaggc ggttccaaca    5760
aaaaattcct gctgtatctt gctggatttg tggattccga tggctccatc attgctcaga    5820
tacgtccaaa tcaatctgca aagttcaaac actacctcca gttgaccttt caagtcactc    5880
agaagacaca aagaaggtgg ttcttggaca aattggttga tcgtattggt gtgggctatg    5940
tcagagactc cggctctgtg tcagactaca aactgtctga aattaagcct cttcataact    6000
```

```
ttctcaccca actgcaaccc ttcttgaagc tcaaacagaa gcaagcaaat ctggttttga    6060
aaatcatcga gcaactgcca tctgccaagg agtcccctga caagtttctt gaagtgtgta    6120
cttgggtgga tcaggtggct gccttgaatg actccaagac cagaaaaacc acctctgaga    6180
ctgtgagggc agttctggat agcctctctg agaagaaaaa gtcctctcct tag           6233

<210> SEQ ID NO 54
<211> LENGTH: 6233
<212> TYPE: DNA
<213> ORGANISM: Artificial sequence
<220> FEATURE:
<223> OTHER INFORMATION: pCLS3387

<400> SEQUENCE: 54
taactcgagc gctagcaccc agctttcttg tacaaagtgg tgatctagag ggcccgcggt      60
tcgaaggtaa gcctatccct aaccctctcc tcggtctcga ttctacgcgt accggttagt     120
aatgagttta acggggggag gctaactgaa acacggaagg agacaatacc ggaaggaacc     180
cgcgctatga cggcaataaa aagacagaat aaaacgcacg ggtgttgggt cgtttgttca     240
taaacgcggg gttcggtccc agggctggca ctctgtcgat accccaccga gaccccattg     300
gggccaatac gcccgcgttt cttccttttc cccaccccac cccccaagtt cgggtgaagg     360
cccagggctc gcagccaacg tcggggcggc aggccctgcc atagcagatc tgcgcagctg     420
gggctctagg gggtatcccc acgcgccctg tagcggcgca ttaagcgcgg cgggtgtggt     480
ggttacgcgc agcgtgaccg ctacacttgc cagcgcccta gcgcccgctc ctttcgcttt     540
cttcccttcc tttctcgcca cgttcgccgg ctttccccgt caagctctaa atcggggcat     600 cccttttaggg ttccgattta gtgctttacg gcacctcgac cccaaaaaac ttgattaggg     660
tgatggttca cgtagtgggc catcgccctg atagacggtt tttcgccctt tgacgttgga     720
gtccacgttc tttaatagtg gactcttgtt ccaaactgga acaacactca accctatctc     780
ggtctattct tttgatttat aagggatttt ggggatttcg gcctattggt taaaaaatga     840
gctgatttaa caaaaattta cgcgaatta attctgtgga atgtgtgtca gttagggtgt     900
ggaaagtccc caggctcccc agcaggcaga agtatgcaaa gcatgcatct caattagtca     960
gcaaccaggt gtggaaagtc cccaggctcc ccagcaggca gaagtatgca aagcatgcat    1020
ctcaattagt cagcaaccat agtcccgccc ctaactccgc ccatcccgcc cctaactccg    1080
cccagttccg cccattctcc gccccatggc tgactaattt ttttttattta tgcagaggcc    1140 gaggccgcct ctgcctctga gctattccag aagtagtgag gaggcttttt tggaggccta    1200
ggcttttgca aaaagctccc gggagcttgt atatccattt tcggatctga tcagcacgtg    1260
ttgacaatta atcatcggca tagtatatcg gcatagtata atacgacaag gtgaggaact    1320
aaaccatggc caagcctttg tctcaagaag aatccaccct cattgaaaga gcaacggcta    1380
caatcaacag catccccatc tctgaagact acagcgtcgc cagcgcagct ctctctagcg    1440
acggccgcat cttcactggt gtcaatgtat atcattttac tgggggacct tgtgcagaac    1500
tcgtggtgct gggcactgct gctgctgcgg cagctggcaa cctgacttgt atcgtcgcga    1560
tcggaaatga aacagggggc atcttgagcc cctgcggacg tgccgacagt gcttctcg    1620 atctgcatcc tgggatcaaa gccatagtga aggacagtga tggacagccg acggcagttg    1680
ggattcgtga attgctgccc tctggttatg tgtgggaggg ctaagcactt cgtggccgag    1740
gagcaggact gacacgtgct acgagatttc gattccaccg ccgccttcta tgaaaggttg    1800
ggcttcggaa tcgttttccg gacgccggc tggatgatcc tccagcgcgg ggatctcatg    1860
```

```
ctggagttct tcgcccaccc caacttgttt attgcagctt ataatggtta caaataaagc    1920
aatagcatca caaatttcac aaataaagca ttttttttcac tgcattctag ttgtggtttg   1980
tccaaactca tcaatgtatc ttatcatgtc tgtataccgt cgacctctag ctagagcttg    2040
gcgtaatcat ggtcatagct gtttcctgtg tgaaattgtt atccgctcac aattccacac    2100
aacatacgag ccggaagcat aaagtgtaaa gcctggggtg cctaatgagt gagctaactc    2160
acattaattg cgttgcgctc actgcccgct ttccagtcgg gaaacctgtc gtgccagctg    2220
cattaatgaa tcggccaacg cgcggggaga ggcggtttgc gtattgggcg ctcttccgct    2280
tcctcgctca ctgactcgct gcgctcggtc gttcggctgc ggcgagcggt atcagctcac    2340
tcaaaggcgg taatacggtt atccacagaa tcaggggata acgcaggaaa gaacatgtga    2400
gcaaaaggcc agcaaaaggc caggaaccgt aaaaaggccg cgttgctggc gtttttccat    2460
aggctccgcc cccctgacga gcatcacaaa aatcgacgct caagtcagag gtggcgaaac    2520
ccgacaggac tataaagata ccaggcgttt ccccctggaa gctccctcgt gcgctctcct    2580
gttccgaccc tgccgcttac cggatacctg tccgcctttc tcccttcggg aagcgtggcg    2640
ctttctcata gctcacgctg taggtatctc agttcggtgt aggtcgttcg ctccaagctg    2700
ggctgtgtgc acgaaccccc cgttcagccc gaccgctgcg ccttatccgg taactatcgt    2760
cttgagtcca acccggtaag acacgactta tcgccactgg cagcagccac tggtaacagg    2820
attagcagag cgaggtatgt aggcggtgct acagagttct tgaagtggtg cctaactac     2880 ggctacacta agaacagt atttggtatc tgcgctctgc tgaagccagt taccttcgga     2940
aaaagagttg gtagctcttg atccggcaaa caaaccaccg ctggtagcgg tttttttgtt    3000
tgcaagcagc agattacgcg cagaaaaaaa ggatctcaag aagatccttt gatcttttct    3060
acggggtctg acgctcagtg aacgaaaac tcacgttaag ggattttggt catgagatta     3120
tcaaaaagga tcttcaccta gatccttta aattaaaaat gaagttttaa atcaatctaa     3180
agtatatatg agtaaacttg gtctgacagt taccaatgct taatcagtga ggcacctatc    3240
tcagcgatct gtctatttcg ttcatccata gttgcctgac tccccgtcgt gtagataact    3300
acgatacggg agggcttacc atctggcccc agtgctgcaa tgataccgcg agacccacgc    3360
tcaccggctc cagatttatc agcaataaac cagccagccg aagggccga gcgcagaagt     3420 ggtcctgcaa ctttatccgc ctccatccag tctattaatt gttgccggga agctagagta    3480
agtagttcgc cagttaatag tttgcgcaac gttgttgcca ttgctacagg catcgtggtg    3540
tcacgctcgt cgtttggtat ggcttcattc agctccggtt cccaacgatc aaggcgagtt    3600
acatgatccc ccatgttgtg caaaaaagcg gttagctcct tcggtcctcc gatcgttgtc    3660
agaagtaagt tggccgcagt gttatcactc atggttatgg cagcactgca taattctctt    3720
actgtcatgc catccgtaag atgcttttct gtgactggtg agtactcaac caagtcattc    3780
tgagaatagt gtatgcggcg accgagttgc tcttgcccgg cgtcaatacg gataatacc     3840 gcgccacata gcagaacttt aaaagtgctc atcattggaa aacgttcttc ggggcgaaaa    3900
ctctcaagga tcttaccgct gttgagatcc agttcgatgt aacccactcg tgcacccaac    3960
tgatcttcag catcttttac tttcaccagc gtttctggga gcaaaaaac aggaaggcaa     4020 aatgccgcaa aaaagggaat aagggcgaca cggaaatgtt gaatactcat actcttcctt    4080
tttcaatatt attgaagcat ttatcagggt tattgtctca tgagcggata catatttgaa    4140
tgtatttaga aaaataaaca aataggggtt ccgcgcacat ttccccgaaa agtgccacct    4200
```

```
gacgtcgacg gatcgggaga tctcccgatc cctatggtg cactctcagt acaatctgct    4260
ctgatgccgc atagttaagc cagtatctgc tccctgcttg tgtgttggag gtcgctgagt    4320
agtgcgcgag caaaatttaa gctacaacaa ggcaaggctt gaccgacaat tgcatgaaga    4380
atctgcttag ggttaggcgt tttgcgctgc ttcgcgatgt acgggccaga tatacgcgtt    4440
gacattgatt attgactagt tattaatagt aatcaattac ggggtcatta gttcatagcc    4500
catatatgga gttccgcgtt acataactta cggtaaatgg cccgcctggc tgaccgccca    4560
acgacccccg cccattgacg tcaataatga cgtatgttcc catagtaacg ccaataggga    4620
ctttccattg acgtcaatgg gtggagtatt tacggtaaac tgcccacttg gcagtacatc    4680
aagtgtatca tatgccaagt acgccccta ttgacgtcaa tgacggtaaa tggcccgcct    4740
ggcattatgc ccagtacatg accttatggg actttcctac ttggcagtac atctacgtat    4800
tagtcatcgc tattaccatg gtgatgcggt tttggcagta catcaatggg cgtggatagc    4860
ggtttgactc acggggattt ccaagtctcc accccattga cgtcaatggg agtttgtttt    4920
ggcaccaaaa tcaacgggac tttccaaaat gtcgtaacaa ctccgcccca ttgacgcaaa    4980
tgggcggtag gcgtgtacgg tgggaggtct atataagcag agctctctgg ctaactagag    5040
aacccactgc ttactggctt atcgaaatga attcgactca ctgttgggag acccaagctg    5100
gctagttaag ctatcacaag tttgtacaaa aaagcaggct ggcgcgccta cacagcggcc    5160
ttgccaccat ggccaatacc aaatataacg aagagttcct gctgtacctg gccggctttg    5220
tggacggtga cggtagcatc atcgctcaga ttaaaccacg tcagtcttat aagtttaaac    5280
atcagctaga attgaccttt accgtgggtc aaaagaccca gcgccgttgg tttctggaca    5340
aactagtgga tgaaattggc gttggttacg taaccgatag cggtagcatg tccgcatacc    5400
gtttaagcaa aatcaagccg ctgcacaact tcctgactca actgcagccg tttctggaac    5460
tgaaacagaa acaggcaaac ctggttctga aaattatcga acagctgccg tctgcaaaag    5520
aatccccgga caaattcctg gaagtttgta cctgggtgga tcaggttgca gctctgaacg    5580
attctaagac gcgtaaaacc acttctgaaa ccgttcgtgc tgtgctggac aacctgagcg    5640
agaagaagaa atcctccccg gcggccggtg gatctgataa gtataatcag gctctgtcta    5700
aatacaacca agcactgtcc aagtacaatc aggccctgtc tggtggaggc ggttccaaca    5760
aaaaattcct gctgtatctt gctggatttg tggatagcga tggctccatc attgctcaga    5820
tacgtccaaa tcaatctgca aagttcaaac actacctcca gttgaccttt caagtcactc    5880
agaagacaca aagaaggtgg ttcttggaca aattggttga tcgtattggt gtgggccacg    5940
tcagagacag cggctctgtg tcagactaca aactgtctga aattaagcct cttcataact    6000
ttctcaccca actgcaaccc ttcttgaagc tcaaacagaa gcaagcaaat ctggttttga    6060
aaatcatcga gcaactgcca tctgccaagg agtccctga caagtttctt gaagtgtgta    6120
cttgggtgga tcaggttgct gccttgaatg actccaagac cagaaaaacc acctctgaga    6180
ctgtgagggc agttctggat agcctctctg agaagaaaaa gtcctctcct tag           6233
```

<210> SEQ ID NO 55
<211> LENGTH: 6233
<212> TYPE: DNA
<213> ORGANISM: Artificial sequence
<220> FEATURE:
<223> OTHER INFORMATION: pCLS3631

<400> SEQUENCE: 55

```
taactcgagc gctagcaccc agctttcttg tacaaagtgg tgatctagag ggcccgcggt      60
```

-continued

```
tcgaaggtaa gcctatccct aaccctctcc tcggtctcga ttctacgcgt accggttagt      120
aatgagttta acgggggag gctaactgaa acacggaagg agacaatacc ggaaggaacc       180
cgcgctatga cggcaataaa aagacagaat aaaacgcacg ggtgttgggt cgtttgttca      240
taaacgcggg gttcggtccc agggctggca ctctgtcgat accccaccga gaccccattg      300
gggccaatac gcccgcgttt cttccttttc cccaccccac ccccaagtt cgggtgaagg       360 cccagggctc gcagccaacg tcggggcggc aggccctgcc atagcagatc tgcgcagctg      420
gggctctagg gggtatcccc acgcgccctg tagcggcgca ttaagcgcgg cgggtgtggt      480
ggttacgcgc agcgtgaccg ctacacttgc cagcgcccta gcgcccgctc ctttcgcttt      540
cttcccttcc tttctcgcca cgttcgccgg ctttccccgt caagctctaa atcggggcat      600 cccctttaggg ttccgattta tgctttacg gcacctcgac cccaaaaaac ttgattaggg      660
tgatggttca cgtagtgggc catcgccctg atagacggtt tttcgccctt tgacgttgga      720
gtccacgttc tttaatagtg gactcttgtt ccaaactgga acaacactca accctatctc      780
ggtctattct tttgatttat aagggatttt ggggatttcg gcctattggt taaaaaatga      840
gctgatttaa caaaaattta acgcgaatta attctgtgga atgtgtgtca gttagggtgt      900
ggaaagtccc caggctcccc agcaggcaga agtatgcaaa gcatgcatct caattagtca      960
gcaaccaggt gtggaaagtc cccaggctcc ccagcaggca gaagtatgca aagcatgcat     1020
ctcaattagt cagcaaccat agtcccgccc ctaactccgc ccatcccgcc cctaactccg     1080
cccagttccg cccattctcc gccccatggc tgactaattt tttttattta tgcagaggcc     1140
gaggccgcct ctgcctctga gctattccag aagtagtgag gaggcttttt tggaggccta     1200
ggcttttgca aaaagctccc gggagcttgt atatccattt tcggatctga tcagcacgtg     1260
ttgacaatta atcatcggca tagtatatcg gcatagtata atacgacaag gtgaggaact     1320
aaaccatggc caagcctttg tctcaagaag aatccaccct cattgaaaga gcaacggcta     1380
caatcaacag catccccatc tctgaagact acagcgtcgc cagcgcagct ctctctagcg     1440
acggccgcat cttcactggt gtcaatgtat atcattttac tgggggacct tgtgcagaac     1500
tcgtggtgct gggcactgct gctgctgcgg cagctggcaa cctgacttgt atcgtcgcga     1560
tcggaaatga gaacaggggc atcttgagcc cctgcggacg tgccgacag gtgcttctcg      1620 atctgcatcc tgggatcaaa gccatagtga aggacagtga tggacagccg acggcagttg     1680
ggattcgtga attgctgccc tctggttatg tgtgggaggg ctaagcactt cgtggccgag     1740
gagcaggact gacacgtgct acgagatttc gattccaccg ccgccttcta tgaaaggttg     1800
ggcttcggaa tcgttttccg ggacgccggc tggatgatcc tccagcgcgg ggatctcatg     1860
ctggagttct tcgcccaccc caacttgttt attgcagctt ataatggtta caaataaagc     1920
aatagcatca caaatttcac aaataaagca tttttttcac tgcattctag ttgtggtttg     1980
tccaaactca tcaatgtatc ttatcatgtc tgtataccgt cgacctctag ctagagcttg     2040
gcgtaatcat ggtcatagct gtttcctgtg tgaaattgtt atccgctcac aattccacac     2100
aacatacgag ccggaagcat aaagtgtaaa gcctggggtg cctaatgagt gagctaactc     2160
acattaattg cgttgcgctc actgcccgct ttccagtcgg gaaacctgtc gtgccagctg     2220
cattaatgaa tcggccaacg cgcggggaga ggcggtttgc gtattgggcg ctcttccgct     2280
tcctcgctca ctgactcgct gcgctcggtc gttcggctgc ggcgagcggt atcagctcac     2340
tcaaaggcgg taatacggtt atccacagaa tcaggggata acgcaggaaa gaacatgtga     2400
```

```
gcaaaaggcc agcaaaaggc caggaaccgt aaaaaggccg cgttgctggc gttttttccat    2460
aggctccgcc cccctgacga gcatcacaaa aatcgacgct caagtcagag gtggcgaaac    2520
ccgacaggac tataaagata ccaggcgttt ccccctggaa gctccctcgt gcgctctcct    2580
gttccgaccc tgccgcttac cggatacctg tccgcctttc tcccttcggg aagcgtggcg    2640
ctttctcata gctcacgctg taggtatctc agttcggtgt aggtcgttcg ctccaagctg    2700
ggctgtgtgc acgaaccccc cgttcagccc gaccgctgcg ccttatccgg taactatcgt    2760
cttgagtcca acccggtaag acacgactta tcgccactgg cagcagccac tggtaacagg    2820
attagcagag cgaggtatgt aggcggtgct acagagttct tgaagtggtg cctaactac    2880
ggctacacta gaagaacagt atttggtatc tgcgctctgc tgaagccagt taccttcgga    2940
aaaagagttg gtagctcttg atccggcaaa caaaccaccg ctggtagcgg tttttttgtt    3000
tgcaagcagc agattacgcg cagaaaaaaa ggatctcaag aagatccttt gatcttttct    3060
acggggtctg acgctcagtg gaacgaaaac tcacgttaag ggattttggt catgagatta    3120
tcaaaaagga tcttcaccta gatcctttta aattaaaaat gaagttttaa atcaatctaa    3180
agtatatatg agtaaacttg gtctgacagt taccaatgct taatcagtga ggcacctatc    3240
tcagcgatct gtctatttcg ttcatccata gttgcctgac tccccgtcgt gtagataact    3300
acgatacggg agggcttacc atctggcccc agtgctgcaa tgataccgcg agacccacgc    3360
tcaccggctc cagatttatc agcaataaac cagccagccg aagggccga gcgcagaagt    3420
ggtcctgcaa cttttatccgc ctccatccag tctattaatt gttgccggga agctagagta    3480
agtagttcgc cagttaatag tttgcgcaac gttgttgcca ttgctacagg catcgtggtg    3540
tcacgctcgt cgtttggtat ggcttcattc agctccggtt cccaacgatc aaggcgagtt    3600
acatgatccc ccatgttgtg caaaaaagcg gttagctcct tcggtcctcc gatcgttgtc    3660
agaagtaagt tggccgcagt gttatcactc atggttatgg cagcactgca taattctctt    3720
actgtcatgc catccgtaag atgcttttct gtgactggtg agtactcaac caagtcattc    3780
tgagaatagt gtatgcggcg accgagttgc tcttgcccgg cgtcaatacg ggataatacc    3840
gcgccacata gcagaacttt aaaagtgctc atcattggaa aacgttcttc ggggcgaaaa    3900
ctctcaagga tcttaccgct gttgagatcc agttcgatgt aacccactcg tgcacccaac    3960
tgatcttcag catcttttac tttcaccagc gtttctgggt gagcaaaaac aggaaggcaa    4020
aatgccgcaa aaaagggaat aagggcgaca cggaaatgtt gaatactcat actcttcctt    4080
tttcaatatt attgaagcat ttatcagggt tattgtctca tgagcggata catatttgaa    4140
tgtatttaga aaaataaaca ataggggtt ccgcgcacat ttccccgaaa agtgccacct    4200
gacgtcgacg gatcgggaga tctcccgatc ccctatggtg cactctcagt acaatctgct    4260
ctgatgccgc atagttaagc cagtatctgc tccctgcttg tgtgttggag gtcgctgagt    4320
agtgcgcgag caaaatttaa gctacaacaa ggcaaggctt gaccgacaat gcatgaaga    4380
atctgcttag ggttaggcgt tttgcgctgc ttcgcgatgt acgggccaga tatacgcgtt    4440
gacattgatt attgactagt tattaatagt aatcaattac ggggtcatta gttcatagcc    4500
catatatgga gttccgcgtt acataactta cggtaaatgg cccgcctggc tgaccgccca    4560
acgacccccg cccattgacg tcaataatga cgtatgttcc catagtaacg ccaataggga    4620
ctttccattg acgtcaatgg gtggagtatt tacggtaaac tgcccacttg gcagtacatc    4680
aagtgtatca tatgccaagt acgccccta ttgacgtcaa tgacggtaaa tggcccgcct    4740
ggcattatgc ccagtacatg accttatggg actttcctac ttggcagtac atctacgtat    4800
```

```
tagtcatcgc tattaccatg gtgatgcggt tttggcagta catcaatggg cgtggatagc    4860
ggtttgactc acggggattt ccaagtctcc accccattga cgtcaatggg agtttgtttt    4920
ggcaccaaaa tcaacgggac tttccaaaat gtcgtaacaa ctccgcccca ttgacgcaaa    4980
tgggcggtag gcgtgtacgg tgggaggtct atataagcag agctctctgg ctaactagag    5040
aacccactgc ttactggctt atcgaaatga attcgactca ctgttgggag acccaagctg    5100
gctagttaag ctatcacaag tttgtacaaa aaagcaggct ggcgcgccta cacgcggcc    5160 ttgccaccat ggccaatacc aaatataacg aagagttcct gctgtacctg gccggctttg    5220
tggacggtga cggtagcatc atcgctcaga ttaaaccaca tcagacctgt aagtttaaac    5280
atcgtctaag cttgaccttt gctgtgactc aaaagaccca gcgccgttgg tttctggaca    5340
aactagtgga tgaaattggc gttggttacg tacgtgatag cggtagcgtt cctactaca    5400 ccttaagcaa aatcaagccg ctgcacaact tcctgactca actgcagccg tttctggaac    5460
tgaaacagaa acaggcaaac ctggttctga aaattatcga acagctgccg tctgcaaaag    5520
aatccccgga caaattcctg gaagtttgta cctgggtgga tcaggtggca gctctgaacg    5580
attctaagac gcgtaaaacc acttctgaaa ccgttcgtgc tgtgctggac agcctgagcg    5640
agaagaagaa atcctccccg gcggccgtg atctgataa gtataatcag gctctgtcta    5700
aatacaacca agcactgtcc aagtacaatc aggccctgtc tggtggaggc ggttccaaca    5760
aaaaattcct gctgtatctt gctggatttg tggatagcga tggctccatc attgctcaga    5820
taaaaccaaa tcaatctcgt aagttcaaac accagctcga attgaccttt ctggtcactc    5880
agaagacaca aagaaggtgg ttcttggaca aattggctga tcgtgtgggt gtgggctatg    5940
tcagagacgc tggctctgtg tcaaactacc gtctgtctaa aattaagcct cttcataact    6000
ttctcaccca actgcaaccc ttcttgaagc tcaaacagaa gcaagcaaat ctggttttga    6060
aaatcatcga gcaactgcca tctgccaagg agtcccctga caagtttctt gaagtgtgta    6120
cttgggctga tcaggtggct gccttgaatg actccaagac cagaaaaacc acctctgaga    6180
ctgtgagggc agttctggat agcctcggtg agaagaaaaa gtcctctcct tag    6233
```

<210> SEQ ID NO 56
<211> LENGTH: 6233
<212> TYPE: DNA
<213> ORGANISM: Artificial sequence
<220> FEATURE:
<223> OTHER INFORMATION: pCLS3633

<400> SEQUENCE: 56

```
taactcgagc gctagcaccc agctttcttg tacaaagtgg tgatctagag ggcccgcggt      60
tcgaaggtaa gcctatccct aaccctctcc tcggtctcga ttctacgcgt accggttagt     120
aatgagttta acggggggag gctaactgaa acacggaagg agacaatacc ggaaggaacc     180
cgcgctatga cggcaataaa aagacagaat aaaacgcacg ggtgttgggt cgtttgttca     240
taaacgcggg gttcggtccc agggctggca ctctgtcgat accccaccga daccccattg     300
gggccaatac gcccgcgttt cttcctttc cccaccccac cccccaagtt cgggtgaagg     360
cccagggctc gcagccaacg tcgggcggg aggccctgcc atagcagatc tgcgcagctg     420
gggctctagg gggtatcccc acgcgccctg tagcggcgca ttaagcgcgg cgggtgtggt     480
ggttacgcgc agcgtgaccg ctacacttgc cagcgcccta gcgcccgctc ctttcgcttt     540
cttcccttcc tttctcgcca cgttcgccgg ctttccccgt caagctctaa atcggggcat     600
```

```
cccctttaggg ttccgattta gtgctttacg gcacctcgac cccaaaaaac ttgattaggg      660
tgatggttca cgtagtgggc catcgccctg atagacggtt tttcgccctt tgacgttgga      720
gtccacgttc tttaatagtg gactcttgtt ccaaactgga acaacactca accctatctc      780
ggtctattct tttgatttat aagggatttt ggggatttcg gcctattggt taaaaaatga      840
gctgatttaa caaaaattta acgcgaatta attctgtgga atgtgtgtca gttagggtgt      900
ggaaagtccc caggctcccc agcaggcaga agtatgcaaa gcatgcatct caattagtca      960
gcaaccaggt gtggaaagtc cccaggctcc ccagcaggca gaagtatgca aagcatgcat     1020
ctcaattagt cagcaaccat agtcccgccc ctaactccgc ccatcccgcc cctaactccg     1080
cccagttccg cccattctcc gccccatggc tgactaattt tttttattta tgcagaggcc     1140
gaggccgcct ctgcctctga gctattccag aagtagtgag gaggcttttt tggaggccta     1200
ggcttttgca aaaagctccc gggagcttgt atatccattt tcggatctga tcagcacgtg     1260
ttgacaatta atcatcggca tagtatatcg gcatagtata atacgacaag gtgaggaact     1320
aaaccatggc caagcctttg tctcaagaag aatccaccct cattgaaaga gcaacggcta     1380
caatcaacag catccccatc tctgaagact acagcgtcgc cagcgcagct ctctctagcg     1440
acggccgcat cttcactggt gtcaatgtat atcattttac tggggaccct tgtgcagaac     1500
tcgtggtgct gggcactgct gctgctgcgg cagctggcaa cctgacttgt atcgtcgcga     1560
tcggaaatga acagggggc atcttgagcc cctgcgacg tgccgacag tgcttctcg        1620 atctgcatcc tgggatcaaa gccatagtga aggacagtga tggacagccg acggcagttg     1680
ggattcgtga attgctgccc tctggttatg tgtgggaggg ctaagcactt cgtggccgag     1740
gagcaggact gacacgtgct acgagatttc gattccaccg ccgccttcta tgaaaggttg     1800 ggcttcgaa tcgttttccg ggacgccggc tggatgatcc tccagcgcgg ggatctcatg      1860
ctggagttct tcgcccaccc caacttgttt attgcagctt ataatggtta caaataaagc     1920
aatagcatca caaatttcac aaataaagca tttttttcac tgcattctag ttgtggtttg     1980
tccaaactca tcaatgtatc ttatcatgtc tgtataccgt cgacctctag ctagagcttg     2040
gcgtaatcat ggtcatagct gtttcctgtg tgaaattgtt atccgctcac aattccacac     2100
aacatacgag ccggaagcat aaagtgtaaa gcctggggtg cctaatgagt gagctaactc     2160
acattaattg cgttgcgctc actgcccgct ttccagtcgg gaaacctgtc gtgccagctg     2220
cattaatgaa tcggccaacg cgcggggaga ggcggtttgc gtattgggcg ctcttccgct     2280
tcctcgctca ctgactcgct gcgctcggtc gttcggctgc ggcgagcggt atcagctcac     2340
tcaaaggcgg taatacggtt atccacagaa tcaggggata acgcaggaaa gaacatgtga     2400
gcaaaaggcc agcaaaaggc caggaaccgt aaaaaggccg cgttgctggc gtttttccat     2460
aggctccgcc cccctgacga gcatcacaaa aatcgacgct caagtcagag gtggcgaaac     2520
ccgacaggac tataaagata ccaggcgttt ccccctggaa gctccctcgt gcgctctcct     2580
gttccgaccc tgccgcttac cggatacctg tccgcctttc tcccttcggg aagcgtggcg     2640
ctttctcata gctcacgctg taggtatctc agttcggtgt aggtcgttcg ctccaagctg     2700
ggctgtgtgc acgaaccccc cgttcagccc gaccgctgcg ccttatccgg taactatcgt     2760
cttgagtcca acccggtaag acacgactta tcgccactgg cagcagccac tggtaacagg     2820
attagcagag cgaggtatgt aggcggtgct acagagttct tgaagtggtg gcctaactac     2880
ggctacacta gaagaacagt atttggtatc tgcgctctgc tgaagccagt taccttcgga     2940
aaaagagttg gtagctcttg atccggcaaa caaaccaccg ctggtagcgg tttttttgtt     3000
```

```
tgcaagcagc agattacgcg cagaaaaaaa ggatctcaag aagatccttt gatcttttct   3060
acggggtctg acgctcagtg gaacgaaaac tcacgttaag ggattttggt catgagatta   3120
tcaaaaagga tcttcaccta gatcctttta aattaaaaat gaagttttaa atcaatctaa   3180
agtatatatg agtaaacttg gtctgacagt taccaatgct taatcagtga ggcacctatc   3240
tcagcgatct gtctatttcg ttcatccata gttgcctgac tccccgtcgt gtagataact   3300
acgatacggg agggcttacc atctggcccc agtgctgcaa tgataccgcg agacccacgc   3360
tcaccggctc cagatttatc agcaataaac cagccagccg aagggccga gcgcagaagt   3420
ggtcctgcaa ctttatccgc ctccatccag tctattaatt gttgccggga agctagagta   3480
agtagttcgc cagttaatag tttgcgcaac gttgttgcca ttgctacagg catcgtggtg   3540
tcacgctcgt cgtttggtat ggcttcattc agctccggtt cccaacgatc aaggcgagtt   3600
acatgatccc ccatgttgtg caaaaaagcg gttagctcct tcggtcctcc gatcgttgtc   3660
agaagtaagt tggccgcagt gttatcactc atggttatgg cagcactgca taattctctt   3720
actgtcatgc catccgtaag atgcttttct gtgactggtg agtactcaac caagtcattc   3780
tgagaatagt gtatgcggcg accgagttgc tcttgcccgg cgtcaatacg ggataatacc   3840
gcgccacata gcagaacttt aaaagtgctc atcattggaa aacgttcttc ggggcgaaaa   3900
ctctcaagga tcttaccgct gttgagatcc agttcgatgt aacccactcg tgcacccaac   3960
tgatcttcag catcttttac tttcaccagc gtttctgggt gagcaaaaac aggaaggcaa   4020
aatgccgcaa aaaagggaat aagggcgaca cggaaatgtt gaatactcat actcttcctt   4080
tttcaatatt attgaagcat ttatcagggt tattgtctca tgagcggata catatttgaa   4140
tgtatttaga aaaataaaca ataggggtt ccgcgcacat ttccccgaaa agtgccacct   4200
gacgtcgacg gatcgggaga tctcccgatc ccctatggtg cactctcagt acaatctgct   4260
ctgatgccgc atagttaagc cagtatctgc tccctgcttg tgtgttggag gtcgctgagt   4320
agtgcgcgag caaaatttaa gctacaacaa ggcaaggctt gaccgacaat tgcatgaaga   4380
atctgcttag ggttaggcgt tttgcgctgc ttcgcgatgt acgggccaga tatacgcgtt   4440
gacattgatt attgactagt tattaatagt aatcaattac ggggtcatta gttcatagcc   4500
catatatgga gttccgcgtt acataactta cggtaaatgg cccgcctggc tgaccgccca   4560
acgacccccg cccattgacg tcaataatga cgtatgttcc catagtaacg ccaatagga   4620
cttttccattg acgtcaatgg gtggagtatt tacggtaaac tgcccacttg gcagtacatc   4680
aagtgtatca tatgccaagt acgccccta ttgacgtcaa tgacggtaaa tggcccgcct   4740
ggcattatgc ccagtacatg accttatggg actttcctac ttggcagtac atctacgtat   4800
tagtcatcgc tattaccatg gtgatgcggt tttggcagta catcaatggg cgtggatagc   4860
ggtttgactc acggggattt ccaagtctcc accccattga cgtcaatggg agtttgtttt   4920
ggcaccaaaa tcaacgggac tttccaaaat gtcgtaacaa ctccgcccca ttgacgcaaa   4980
tgggcggtag gcgtgtacgg tgggaggtct atataagcag agctctctgg ctaactagag   5040
aacccactgc ttactggctt atcgaaatga attcgactca ctgttgggag acccaagctg   5100
gctagttaag ctatcacaag tttgtacaaa aaagcaggct ggcgcgccta cacagcggcc   5160
ttgccaccat ggccaatacc aaatataacg aagagttcct gctgtacctg gccggctttg   5220
tggacggtga cggtagcatc atcgctcaga ttaaaccaca tcagacctgt aagtttaaac   5280
atcgtctaag cttgaccttt gctgtgactc aaaagaccca gcgccgttgg tttctggaca   5340
```

```
aactagtgga tgaaattggc gttggttacg tacgtgatag cggtagcgtt tcctactaca    5400
ccttaagcaa aatcaagccg ctgcacaact tcctgactca actgcagccg tttctggaac    5460
tgaaacagaa acaggcaaac ctggctctga aaattatcga acagctgccg tctgcaaaag    5520
aatccccgga caaattcctg gaagtttgta cctgggtgga tcaggtggca gctctgaacg    5580
attctaagac gcgtaaaacc acttctgaaa ccgttcgtgc tgtgctggac agcctgagcg    5640
agaagaagaa atcctcccccg gcggccggtg gatctgataa gtataatcag gctctgtcta    5700
aatacaacca agcactgtcc aagtacaatc aggccctgtc tggtggaggc ggttccaaca    5760
aaaaattcct gctgtatctt gctggatttg tggatagcga tggctccatc attgctcaga    5820
taaaaccaaa tcaatctcgt aagttcaaac accagctcga attgacccttt ctggtcactc    5880 agaagacaca aagaaggtgg ttcttggaca aattggctga tcgtgtgggt gtgggctatg    5940
tcagagacgc tggctctgtg tcaaactacc gtctgtctaa aattaagcct cttcataact    6000
ttctcaccca actgcaaccc ttcttgaagc tcaaacagaa gcaagcaaat ctggttttga    6060 aaaatcatcga gcaactgcca tctgccaagg agtcccctga caagtttctt gaagtgtgta    6120
cttgggctga tcaggtggct gccttgaatg actccaagac cagaaaaacc acctctgaga    6180
ctgtgagggc agttctggat agcctcggtg agaagaaaaa gtcctctcct tag          6233

<210> SEQ ID NO 57
<211> LENGTH: 6233
<212> TYPE: DNA
<213> ORGANISM: Artificial sequence
<220> FEATURE:
<223> OTHER INFORMATION: pCLS3326

<400> SEQUENCE: 57
taactcgagc gctagcaccc agctttcttg tacaaagtgg tgatctagag ggcccgcggt      60
tcgaaggtaa gcctatccct aaccctctcc tcggtctcga ttctacgcgt accggttagt     120
aatgagttta acggggggag gctaactgaa acacggaagg agacaatacc ggaaggaacc     180
cgcgctatga cggcaataaa aagacagaat aaaacgcacg ggtgttgggt cgtttgttca     240
taaacgcggg gttcggtccc agggctggca ctctgtcgat accccaccga daccccattg     300 ggccaatac gcccgcgttt cttcctttttc cccacccccac cccccaagtt cgggtgaagg     360
cccagggctc gcagccaacg tcggggcggc aggccctgcc atagcagatc tgcgcagctg     420
gggctctagg gggtatcccc acgcgccctg tagcggcgca ttaagcgcgg cgggtgtggt     480
ggttacgcgc agcgtgaccg ctacacttgc cagcgcccta gcgcccgctc ctttcgcttt     540
cttcccttcc tttctcgcca cgttcgccgg ctttccccgt caagctctaa atcggggcat     600
ccctttaggg ttccgattta gtgctttacg gcacctcgac cccaaaaaac ttgattaggg     660
tgatggttca cgtagtgggc catcgccctg atagacggtt tttcgccctt tgacgttgga     720
gtccacgttc tttaatagtg gactcttgtt ccaaactgga acaacactca accctatctc     780
ggtctattct tttgatttat aagggatttt ggggatttcg gcctattggt taaaaaatga     840
gctgatttaa caaaaattta acgcgaatta attctgtgga atgtgtgtca gttagggtgt     900
ggaaagtccc caggctcccc agcaggcaga agtatgcaaa gcatgcatct caattagtca     960
gcaaccaggt gtggaaagtc cccaggctcc ccagcaggca gaagtatgca aagcatgcat    1020
ctcaattagt cagcaaccat agtcccgccc ctaactccgc ccatcccgcc cctaactccg    1080
cccagttccg cccattctcc gccccatggc tgactaattt tttttattta tgcagaggcc    1140
gaggccgcct ctgcctctga gctattccag aagtagtgag gaggcttttt tggaggccta    1200
```

```
ggcttttgca aaaagctccc gggagcttgt atatccattt tcggatctga tcagcacgtg  1260
ttgacaatta atcatcggca tagtatatcg gcatagtata atacgacaag gtgaggaact  1320
aaaccatggc caagcctttg tctcaagaag aatccaccct cattgaaaga gcaacggcta  1380
caatcaacag catccccatc tctgaagact acagcgtcgc cagcgcagct ctctctagcg  1440
acggccgcat cttcactggt gtcaatgtat atcattttac tgggggacct tgtgcagaac  1500
tcgtggtgct gggcactgct gctgctgcgg cagctggcaa cctgacttgt atcgtcgcga  1560
tcggaaatga gaacaggggc atcttgagcc cctgcggacg gtgccgacag gtgcttctcg  1620
atctgcatcc tgggatcaaa gccatagtga aggacagtga tggacagccg acggcagttg  1680
ggattcgtga attgctgccc tctggttatg tgtgggaggg ctaagcactt cgtggccgag  1740
gagcaggact gacacgtgct acgagatttc gattccaccg ccgccttcta tgaaaggttg  1800
ggcttcggaa tcgttttccg ggacgccggc tggatgatcc tccagcgcgg ggatctcatg  1860
ctggagttct tcgcccaccc caacttgttt attgcagctt ataatggtta caaataaagc  1920
aatagcatca caaatttcac aaataaagca ttttttttcac tgcattctag ttgtggtttg  1980
tccaaactca tcaatgtatc ttatcatgtc tgtataccgt cgacctctag ctagagcttg  2040
gcgtaatcat ggtcatagct gtttcctgtg tgaaattgtt atccgctcac aattccacac  2100
aacatacgag ccggaagcat aaagtgtaaa gcctggggtg cctaatgagt gagctaactc  2160
acattaattg cgttgcgctc actgcccgct ttccagtcgg gaaacctgtc gtgccagctg  2220
cattaatgaa tcggccaacg cgcggggaga ggcggtttgc gtattgggcg ctcttccgct  2280
tcctcgctca ctgactcgct gcgctcggtc gttcggctgc ggcgagcggt atcagctcac  2340
tcaaaggcgg taatacggtt atccacagaa tcagggggata acgcaggaaa gaacatgtga  2400
gcaaaaggcc agcaaaaggc caggaaccgt aaaaaggccg cgttgctggc gttttttccat  2460 aggctccgcc cccctgacga gcatcacaaa aatcgacgct caagtcagag gtggcgaaac  2520
ccgacaggac tataaagata ccaggcgttt ccccctggaa gctccctcgt gcgctctcct  2580
gttccgaccc tgccgcttac cggatacctg tccgcctttc tcccttcggg aagcgtggcg  2640
ctttctcata gctcacgctg taggtatctc agttcggtgt aggtcgttcg ctccaagctg  2700
ggctgtgtgc acgaaccccc cgttcagccc gaccgctgcg ccttatccgg taactatcgt  2760
cttgagtcca acccggtaag acacgactta tcgccactgg cagcagccac tggtaacagg  2820
attagcagag cgaggtatgt aggcggtgct acagagttct tgaagtggtg gcctaactac  2880
ggctacacta gaagaacagt atttggtatc tgcgctctgc tgaagccagt taccttcgga  2940
aaaagagttg gtagctcttg atccggcaaa caaaccaccg ctggtagcgg ttttttttgtt  3000 tgcaagcagc agattacgcg cagaaaaaaa ggatctcaag aagatccttt gatcttttct  3060
acggggtctg acgctcagtg gaacgaaaac tcacgttaag ggattttggt catgagatta  3120
tcaaaaagga tcttcaccta gatccttttta aattaaaaat gaagttttaa atcaatctaa  3180
agtatatatg agtaaacttg gtctgacagt taccaatgct taatcagtga ggcacctatc  3240
tcagcgatct gtctatttcg ttcatccata gttgcctgac tccccgtcgt gtagataact  3300
acgatacggg agggcttacc atctggcccc agtgctgcaa tgataccgcg agacccacgc  3360
tcaccggctc cagatttatc agcaataaac cagccagccg aagggccga gcgcagaagt  3420 ggtcctgcaa cttatccgc ctccatccag tctattaatt gttgccggga agctagagta  3480
agtagttcgc cagttaatag tttgcgcaac gttgttgcca ttgctacagg catcgtggtg  3540
```

```
tcacgctcgt cgtttggtat ggcttcattc agctccggtt cccaacgatc aaggcgagtt    3600
acatgatccc ccatgttgtg caaaaaagcg gttagctcct tcggtcctcc gatcgttgtc    3660
agaagtaagt tggccgcagt gttatcactc atggttatgg cagcactgca taattctctt    3720
actgtcatgc catccgtaag atgcttttct gtgactggtg agtactcaac caagtcattc    3780
tgagaatagt gtatgcggcg accgagttgc tcttgcccgg cgtcaatacg ggataatacc    3840
gcgccacata gcagaacttt aaaagtgctc atcattggaa aacgttcttc ggggcgaaaa    3900
ctctcaagga tcttaccgct gttgagatcc agttcgatgt aacccactcg tgcacccaac    3960
tgatcttcag catcttttac tttcaccagc gtttctgggt gagcaaaaac aggaaggcaa    4020
aatgccgcaa aaaagggaat aagggcgaca cggaaatgtt gaatactcat actcttcctt    4080
tttcaatatt attgaagcat ttatcagggt tattgtctca tgagcggata catatttgaa    4140
tgtatttaga aaaataaaca ataggggtt ccgcgcacat ttccccgaaa agtgccacct    4200
gacgtcgacg gatcgggaga tctcccgatc ccctatggtg cactctcagt acaatctgct    4260
ctgatgccgc atagttaagc cagtatctgc tccctgcttg tgtgttggag gtcgctgagt    4320
agtgcgcgag caaaatttaa gctacaacaa ggcaaggctt gaccgacaat tgcatgaaga    4380
atctgcttag ggttaggcgt tttgcgctgc ttcgcgatgt acgggccaga tatacgcgtt    4440
gacattgatt attgactagt tattaatagt aatcaattac ggggtcatta gttcatagcc    4500
catatatgga gttccgcgtt acataactta cggtaaatgg cccgcctggc tgaccgccca    4560
acgacccccg cccattgacg tcaataatga cgtatgttcc catagtaacg ccaataggga    4620
ctttccattg acgtcaatgg gtggagtatt tacggtaaac tgcccacttg gcagtacatc    4680
aagtgtatca tatgccaagt acgccccta ttgacgtcaa tgacggtaaa tggcccgcct    4740
ggcattatgc ccagtacatg accttatggg actttcctac ttggcagtac atctacgtat    4800
tagtcatcgc tattaccatg gtgatgcggt tttggcagta catcaatggg cgtggatagc    4860
ggtttgactc acggggattt ccaagtctcc accccattga cgtcaatggg agtttgtttt    4920
ggcaccaaaa tcaacgggac tttccaaaat gtcgtaacaa ctccgcccca ttgacgcaaa    4980
tgggcggtag gcgtgtacgg tgggaggtct atataagcag agctctctgg ctaactagag    5040
aacccactgc ttactggctt atcgaaatga attcgactca ctgttgggag acccaagctg    5100
gctagttaag ctatcacaag tttgtacaaa aaagcaggct ggcgcgccta cacagcggcc    5160
ttgccaccat ggccaatacc aaatataacg aagagttcct gctgtacctg gccggctttg    5220
tggacggtga cggtagcatc atcgctcaga ttaaaccacg tcaggccaac aagtttaaac    5280
atcagctaga attgaccttt accgtgactc aaaagaccca gcgccgttgg tttctggaca    5340
aactagtgga tgaaattggc gttggttacg tatacgattc cggtagcgtt tccaaatacc    5400
agttaagcaa aatcaagccg ctgcacaact tcctgactca actgcagccg tttctggaac    5460
tgaaacagaa acaggcaaac ctggttctga aaattatcga acagctgccg tctgcaaaag    5520
aatccccgga caaattcctg gaagtttgta cctgggtgga tcaggtggca gctctgaacg    5580
attctaagac gcgtaaaacc acttctgaaa ccgttcgtgc tgtgctggac agcctgagcg    5640
agaagaagaa atcctcccg gcggccgtg atctgataa gtataatcag gctctgtcta    5700
aatacaacca agcactgtcc aagtacaatc aggccctgtc tggtggaggc ggttccaaca    5760
aaaaattcct gctgtatctt gctggatttg tggattccga tggctccatc attgctcaga    5820
taaaaccaaa tcaaggtcac aagttcaaac accagctctc cttgaccttt aaagtcactc    5880
agaagacaca aagaaggtgg ttcttggaca aattggttga tcgtattggt gtgggctatg    5940
```

```
tctacgactc cggctctgtg tcatactaca acctgtctga aattaagcct cttcataact    6000
ttctcaccca actgcaaccc ttcttgaagc tcaaacagaa gcaagcaaat ctggttttga    6060
aaatcatcga gcaactgcca tctgccaagg agtccctga caagtttctt gaagtgtgta    6120
cttgggtgga tcaggtggct gccttgaatg actccaagac cagaaaaacc acctctgaga    6180
ctgtgagggc agttctggat agcctctctg agaagaaaaa gtcctctcct tag           6233

<210> SEQ ID NO 58
<211> LENGTH: 6233
<212> TYPE: DNA
<213> ORGANISM: Artificial sequence
<220> FEATURE:
<223> OTHER INFORMATION: pCLS3330

<400> SEQUENCE: 58
taactcgagc gctagcaccc agctttcttg tacaaagtgg tgatctagag ggcccgcggt      60
tcgaaggtaa gcctatccct aaccctctcc tcggtctcga ttctacgcgt accggttagt     120
aatgagttta acgggggag gctaactgaa acacggaagg agacaatacc ggaaggaacc      180
cgcgctatga cggcaataaa aagacagaat aaaacgcacg ggtgttgggt cgtttgttca     240
taaacgcggg gttcggtccc agggctggca ctctgtcgat accccaccga gaccccattg     300
gggccaatac gcccgcgttt cttccttttc cccaccccac cccccaagtt cgggtgaagg     360
cccagggctc gcagccaacg tcgggcggc aggccctgcc atagcagatc tgcgcagctg      420
gggctctagg gggtatcccc acgcgccctg tagcggcgca ttaagcgcgg cgggtgtggt     480
ggttacgcgc agcgtgaccg ctacacttgc cagcgcccta gcgcccgctc ctttcgcttt     540
cttcccttcc tttctcgcca cgttcgccgg ctttccccgt caagctctaa atcggggcat     600
ccctttaggg ttccgattta gtgctttacg gcacctcgac cccaaaaaac ttgattaggg     660
tgatggttca cgtagtgggc catcgccctg atagacggtt tttcgccctt tgacgttgga     720
gtccacgttc tttaatagtg gactcttgtt ccaaactgga acaacactca accctatctc     780
ggtctattct tttgatttat aagggatttt gggatttcg gcctattggt taaaaaatga     840
gctgatttaa caaaaattta cgcgaatta attctgtgga atgtgtgtca gttagggtgt     900
ggaaagtccc caggctcccc agcaggcaga agtatgcaaa gcatgcatct caattagtca     960
gcaaccaggt gtggaaagtc cccaggctcc ccagcaggca gaagtatgca aagcatgcat    1020
ctcaattagt cagcaaccat agtcccgccc ctaactccgc ccatcccgcc cctaactccg    1080
cccagttccg cccattctcc gccccatggc tgactaattt ttttatta tgcagaggcc     1140 gaggccgcct ctgcctctga gctattccag aagtagtgag gaggcttttt tggaggccta    1200
ggcttttgca aaaagctccc gggagcttgt atatccattt tcggatctga tcagcacgtg    1260
ttgacaatta atcatcggca tagtatatcg gcatagtata atacgacaag gtgaggaact    1320
aaaccatggc caagcctttg tctcaagaag aatccaccct cattgaaaga gcaacggcta    1380
caatcaacag catccccatc tctgaagact acagcgtcgc cagcgcagct ctctctagcg    1440
acggccgcat cttcactggt gtcaatgtat atcattttac tgggggacct tgtgcagaac    1500
tcgtggtgct gggcactgct gctgctgcgg cagctggcaa cctgacttgt atcgtcgcga    1560
tcggaaatga gaacagggc atcttgagcc cctgcggacg tgccgacag gtgcttctcg      1620 atctgcatcc tgggatcaaa gccatagtga aggacagtga tggacagccg acggcagttg    1680
ggattcgtga attgctgccc tctggttatg tgtgggaggg ctaagcactt cgtggccgag    1740
```

```
gagcaggact gacacgtgct acgagatttc gattccaccg ccgccttcta tgaaaggttg   1800
ggcttcggaa tcgttttccg ggacgccggc tggatgatcc tccagcgcgg ggatctcatg   1860
ctggagttct tcgcccaccc caacttgttt attgcagctt ataatggtta caaataaagc   1920
aatagcatca caaatttcac aaataaagca ttttttttcac tgcattctag ttgtggtttg   1980
tccaaactca tcaatgtatc ttatcatgtc tgtataccgt cgacctctag ctagagcttg   2040
gcgtaatcat ggtcatagct gtttcctgtg tgaaattgtt atccgctcac aattccacac   2100
aacatacgag ccggaagcat aaagtgtaaa gcctggggtg cctaatgagt gagctaactc   2160
acattaattg cgttgcgctc actgcccgct ttccagtcgg gaaacctgtc gtgccagctg   2220
cattaatgaa tcggccaacg cgcggggaga ggcggtttgc gtattgggcg ctcttccgct   2280
tcctcgctca ctgactcgct gcgctcggtc gttcggctgc ggcgagcggt atcagctcac   2340
tcaaaggcgg taatacggtt atccacagaa tcaggggata acgcaggaaa gaacatgtga   2400
gcaaaaggcc agcaaaaggc caggaaccgt aaaaaggccg cgttgctggc gtttttccat   2460
aggctccgcc cccctgacga gcatcacaaa aatcgacgct caagtcagag gtggcgaaac   2520
ccgacaggac tataaagata ccaggcgttt ccccctggaa gctccctcgt gcgctctcct   2580
gttccgaccc tgccgcttac cggatacctg tccgcctttc tcccttcggg aagcgtggcg   2640
ctttctcata gctcacgctg taggtatctc agttcggtgt aggtcgttcg ctccaagctg   2700
ggctgtgtgc acgaaccccc cgttcagccc gaccgctgcg ccttatccgg taactatcgt   2760
cttgagtcca acccggtaag acacgactta tcgccactgg cagcagccac tggtaacagg   2820
attagcagag cgaggtatgt aggcggtgct acagagttct tgaagtggtg cctaactac   2880 ggctacacta gaagaacagt atttggtatc tgcgctctgc tgaagccagt taccttcgga   2940
aaaagagttg gtagctcttg atccggcaaa caaaccaccg ctggtagcgg ttttttttgtt   3000 tgcaagcagc agattacgcg cagaaaaaaa ggatctcaag aagatccttt gatcttttct   3060
acggggtctg acgctcagtg gaacgaaaac tcacgttaag ggattttggt catgagatta   3120
tcaaaaagga tcttcaccta gatcctttta aattaaaaat gaagttttaa atcaatctaa   3180
agtatatatg agtaaacttg gtctgacagt taccaatgct taatcagtga ggcacctatc   3240
tcagcgatct gtctatttcg ttcatccata gttgcctgac tccccgtcgt gtagataact   3300
acgatacggg agggcttacc atctggcccc agtgctgcaa tgataccgcg agacccacgc   3360
tcaccggctc cagatttatc agcaataaac cagccagccg aagggccga gcgcagaagt   3420 ggtcctgcaa cttatccgc ctccatccag tctattaatt gttgccggga agctagagta   3480
agtagttcgc cagttaatag tttgcgcaac gttgttgcca ttgctacagg catcgtggtg   3540
tcacgctcgt cgtttggtat ggcttcattc agctccggtt cccaacgatc aaggcgagtt   3600
acatgatccc ccatgttgtg caaaaaagcg gttagctcct tcggtcctcc gatcgttgtc   3660
agaagtaagt tggccgcagt gttatcactc atggttatgg cagcactgca taattctctt   3720
actgtcatgc catccgtaag atgcttttct gtgactggtg agtactcaac caagtcattc   3780
tgagaatagt gtatgcggcg accgagttgc tcttgcccgg cgtcaatacg ggataatacc   3840
gcgccacata gcagaacttt aaaagtgctc atcattggaa aacgttcttc ggggcgaaaa   3900
ctctcaagga tcttaccgct gttgagatcc agttcgatgt aacccactcg tgcacccaac   3960
tgatcttcag catcttttac tttcaccagc gtttctgggt gagcaaaaac aggaaggcaa   4020
aatgccgcaa aaaagggaat aagggcgaca cggaaatgtt gaatactcat actcttcctt   4080
tttcaatatt attgaagcat ttatcagggt tattgtctca tgagcggata catatttgaa   4140
```

-continued

```
tgtatttaga aaaataaaca aatagggtt ccgcgcacat ttccccgaaa agtgccacct      4200
gacgtcgacg gatcgggaga tctcccgatc cctatggtg cactctcagt acaatctgct      4260
ctgatgccgc atagttaagc cagtatctgc tccctgcttg tgtgttggag gtcgctgagt     4320
agtgcgcgag caaaatttaa gctacaacaa ggcaaggctt gaccgacaat tgcatgaaga    4380
atctgcttag ggttaggcgt tttgcgctgc ttcgcgatgt acgggccaga tatacgcgtt    4440
gacattgatt attgactagt tattaatagt aatcaattac ggggtcatta gttcatagcc    4500
catatatgga gttccgcgtt acataactta cggtaaatgg cccgcctggc tgaccgccca    4560 acgaccccg cccattgacg tcaataatga cgtatgttcc catagtaacg ccaataggga     4620
ctttccattg acgtcaatgg gtggagtatt tacggtaaac tgcccacttg gcagtacatc    4680
aagtgtatca tatgccaagt acgccccta ttgacgtcaa tgacggtaaa tggcccgcct     4740
ggcattatgc ccagtacatg accttatggg actttcctac ttggcagtac atctacgtat   4800
tagtcatcgc tattaccatg gtgatgcggt tttggcagta catcaatggg cgtggatagc   4860
ggtttgactc acggggattt ccaagtctcc accccattga cgtcaatggg agtttgtttt   4920
ggcaccaaaa tcaacgggac tttccaaaat gtcgtaacaa ctccgcccca ttgacgcaaa    4980
tgggcggtag gcgtgtacgg tgggaggtct atataagcag agctctctgg ctaactagag    5040
aacccactgc ttactggctt atcgaaatga attcgactca ctgttgggag acccaagctg    5100
gctagttaag ctatcacaag tttgtacaaa aaagcaggct ggcgcgccta cacagcggcc    5160
ttgccaccat ggccaatacc aaatataacg aagagttcct gctgtacctg ccggctttg     5220 tggactccga cggtagcatc atcgctcaga ttaaaccacg tcaggcaaac aagtttaaac    5280
atcagctaga attgaccttt caggtgactc aaaagaccca gcgccgttgg tttctggaca    5340
aactagtgga tgaaattggc gttggttacg tacgtgattc cggtagcgtt tcccgttaca    5400
ccttaagcaa aatcaagccg ctgcacaact tcctgactca actgcagccg tttctggaac    5460
tgaaacagaa acaggcaaac ctggttctga aaattatcga acagctgccg tctgcaaaag    5520
aatccccgga caaattcctg gaagtttgta cctgggtgga tcaggttgca gctctgaacg    5580
attctaagac gcgtaaaacc acttctgaaa ccgttcgtgc tgtgctggac agcctgagcg    5640
agaagaagaa atcctccccg gcggccggtg gatctgataa gtataatcag gctctgtcta    5700
aatacaacca agcactgtcc aagtacaatc aggccctgtc tggtggaggc ggttccaaca    5760
aaaaattcct gctgtatctt gctggatttg tggatggtga tggctccatc attgctcaga    5820
taaaaccaaa tcaaggtcac aagttcaaac accagctctc cttgacctt aaagtcactc     5880 agaagacaca aagaaggtgg ttcttggaca aattggttga tcgtattggt gtgggctatg    5940
tctacgactc cggctctgtg tcagactaca actgtctga aattaagcct cttcataact     6000 ttctcacccca actgcaaccc ttcttgaagc tcaaacagaa gcaagcaaat ctggttttga    6060
aaatcatcga gcaactgcca tctgccaagg agtcccctga caagtttctt gaagtgtgta    6120
cttgggtgga tcaggttgct gccttgaatg actccaagac cagaaaaacc acctctgaga    6180
ctgtgagggc agttctggat agcctctctg agaagaaaaa gtcctctcct tag           6233
```

<210> SEQ ID NO 59
<211> LENGTH: 25
<212> TYPE: PRT
<213> ORGANISM: Artificial sequence
<220> FEATURE:
<223> OTHER INFORMATION: Dystrophin fragment

```
<400> SEQUENCE: 59

His Cys Ser Gln Val Pro Gln Pro Ala Cys His Gly Lys Thr Lys Gln
1               5                   10                  15

Phe Thr Ser Ser Asn Gly Ser Pro Glu
            20                  25

<210> SEQ ID NO 60
<211> LENGTH: 14
<212> TYPE: PRT
<213> ORGANISM: Artificial sequence
<220> FEATURE:
<223> OTHER INFORMATION: Dystrophin fragment

<400> SEQUENCE: 60

His Ala Arg Asp Asn Arg Val Ile Cys His Glu Ser Arg Ile
1               5                   10

<210> SEQ ID NO 61
<211> LENGTH: 51
<212> TYPE: PRT
<213> ORGANISM: Artificial sequence
<220> FEATURE:
<223> OTHER INFORMATION: Dystrophin fragment

<400> SEQUENCE: 61

Leu Ser Glu Asp Glu Thr Glu Val Gln Glu Gln Met Asn Leu Leu
1               5                   10                  15

Asn Ser Arg Trp Glu Cys Leu Arg Val Ala Met Glu Lys Gln Ser Asn
            20                  25                  30

Leu His Lys Val Leu Met Asp Leu Gln Asn Gln Gln Leu Lys Glu Leu
        35                  40                  45

Asn Asp Trp
    50

<210> SEQ ID NO 62
<211> LENGTH: 33
<212> TYPE: DNA
<213> ORGANISM: Artificial sequence
<220> FEATURE:
<223> OTHER INFORMATION: Dystrophin fragment

<400> SEQUENCE: 62
tgcctcaggg tagctagcat ggaaaaacaa agc                             33

<210> SEQ ID NO 63
<211> LENGTH: 50
<212> TYPE: PRT
<213> ORGANISM: Artificial sequence
<220> FEATURE:
<223> OTHER INFORMATION: Dystrophin fragment

<400> SEQUENCE: 63

Leu Ser Glu Asp Glu Glu Thr Glu Val Gln Glu Gln Met Asn Leu Leu
1               5                   10                  15

Asn Ser Arg Trp Glu Cys Leu Arg Val His Cys Ser Gln Val Pro Gln
            20                  25                  30

Pro Ala Cys His Gly Lys Thr Lys Gln Phe Thr Ser Ser Asn Gly Ser
        35                  40                  45

Pro Glu
    50

<210> SEQ ID NO 64
```

<211> LENGTH: 61
<212> TYPE: DNA
<213> ORGANISM: Artificial sequence
<220> FEATURE:
<223> OTHER INFORMATION: Dystrophin fragment

<400> SEQUENCE: 64
tgcctcaggg tacattgttc tcaggtacct cagccagcat gctagcatgg aaaaacaaag    60
c                                                                   61

<210> SEQ ID NO 65
<211> LENGTH: 39
<212> TYPE: PRT
<213> ORGANISM: Artificial sequence
<220> FEATURE:
<223> OTHER INFORMATION: Dystrophin fragment

<400> SEQUENCE: 65

Leu Ser Glu Asp Glu Glu Thr Glu Val Gln Glu Gln Met Asn Leu Leu
1               5                   10                  15

Asn Ser Arg Trp Glu Cys Leu Arg Val His Ala Arg Asp Asn Arg Val
            20                  25                  30

Ile Cys His Gly Lys Thr Lys
        35

<210> SEQ ID NO 66
<211> LENGTH: 58
<212> TYPE: DNA
<213> ORGANISM: Artificial sequence
<220> FEATURE:
<223> OTHER INFORMATION: Dystrophin fragment

<400> SEQUENCE: 66
tgcctcaggg tacacgctag ggataacagg gtaatatgct agcatggaaa acaaagc       58

<210> SEQ ID NO 67
<211> LENGTH: 53
<212> TYPE: PRT
<213> ORGANISM: Artificial sequence
<220> FEATURE:
<223> OTHER INFORMATION: Dystrophin fragment

<400> SEQUENCE: 67

Leu Ser Glu Asp Glu Glu Thr Glu Val Gln Glu Gln Met Asn Leu Leu
1               5                   10                  15

Asn Ser Arg Trp Glu Cys Leu Arg Val Ala Ser Met Glu Lys Gln Ser
            20                  25                  30

Asn Leu His Lys Val Leu Met Asp Leu Gln Asn Gln Gln Leu Lys Glu
        35                  40                  45

Leu Asn Asp Trp Leu
    50

<210> SEQ ID NO 68
<211> LENGTH: 61
<212> TYPE: PRT
<213> ORGANISM: Artificial sequence
<220> FEATURE:
<223> OTHER INFORMATION: Dystrophin fragment

<400> SEQUENCE: 68

Leu Ser Glu Asp Glu Glu Thr Glu Val Gln Glu Gln Met Asn Leu Leu
1               5                   10                  15

Asn Ser Arg Trp Glu Cys Leu Arg Val His Cys Ser His Leu Ser Gln

```
                   20                   25                   30

His Ala Ser Met Glu Lys Gln Ser Asn Leu His Lys Val Leu Met Asp
            35                   40                   45

Leu Gln Asn Gln Gln Leu Lys Glu Leu Asn Asp Trp Leu
        50                   55                   60

<210> SEQ ID NO 69
<211> LENGTH: 60
<212> TYPE: PRT
<213> ORGANISM: Artificial sequence
<220> FEATURE:
<223> OTHER INFORMATION: Dystrophin fragment

<400> SEQUENCE: 69

Leu Ser Glu Asp Glu Glu Thr Glu Val Gln Glu Gln Met Asn Leu Leu
1               5                   10                  15

Asn Ser Arg Trp Glu Cys Leu Arg Val His Cys Ser Gln Ser Gln His
                20                  25                  30

Ala Ser Met Glu Lys Gln Ser Asn Leu His Lys Val Leu Met Asp Leu
            35                  40                  45

Gln Asn Gln Gln Leu Lys Glu Leu Asn Asp Trp Leu
        50                  55                  60

<210> SEQ ID NO 70
<211> LENGTH: 61
<212> TYPE: PRT
<213> ORGANISM: Artificial sequence
<220> FEATURE:
<223> OTHER INFORMATION: Dystrophin fragment

<400> SEQUENCE: 70

Leu Ser Glu Asp Glu Glu Thr Glu Val Gln Glu Gln Met Asn Leu Leu
1               5                   10                  15

Asn Ser Arg Trp Glu Cys Leu Arg Val His Cys Ser Gln Leu Ser Gln
                20                  25                  30

His Ala Ser Met Glu Lys Gln Ser Asn Leu His Lys Val Leu Met Asp
            35                  40                  45

Leu Gln Asn Gln Gln Leu Lys Glu Leu Asn Asp Trp Leu
        50                  55                  60

<210> SEQ ID NO 71
<211> LENGTH: 60
<212> TYPE: PRT
<213> ORGANISM: Artificial sequence
<220> FEATURE:
<223> OTHER INFORMATION: Dystrophin fragment

<400> SEQUENCE: 71

Leu Ser Glu Asp Glu Glu Thr Glu Val Gln Glu Gln Met Asn Leu Leu
1               5                   10                  15

Asn Ser Arg Trp Glu Cys Leu Arg Val His Cys Ser His Ser Gln His
                20                  25                  30

Ala Ser Met Glu Lys Gln Ser Asn Leu His Lys Val Leu Met Asp Leu
            35                  40                  45

Gln Asn Gln Gln Leu Lys Glu Leu Asn Asp Trp Leu
        50                  55                  60

<210> SEQ ID NO 72
<211> LENGTH: 57
<212> TYPE: PRT
<213> ORGANISM: Artificial sequence
```

```
<220> FEATURE:
<223> OTHER INFORMATION: Dystrophin fragment

<400> SEQUENCE: 72

Leu Ser Glu Asp Glu Glu Thr Glu Val Gln Glu Gln Met Asn Leu Leu
1               5                   10                  15

Asn Ser Arg Trp Glu Cys Leu Arg Val His Cys Ser Gln Val Leu Ala
            20                  25                  30

Trp Lys Asn Lys Ala Ile Tyr Ile Lys Phe Trp Ile Ser Arg Ile Ser
        35                  40                  45

Asn Lys Ser Met Thr Gly Pro Lys Gln
    50                  55

<210> SEQ ID NO 73
<211> LENGTH: 60
<212> TYPE: PRT
<213> ORGANISM: Artificial sequence
<220> FEATURE:
<223> OTHER INFORMATION: Dystrophin fragment

<400> SEQUENCE: 73

Leu Ser Glu Asp Glu Glu Thr Glu Val Gln Glu Gln Met Asn Leu Leu
1               5                   10                  15

Asn Ser Arg Trp Glu Cys Leu Arg Val His Cys Ser Gln Val Gln Ser
            20                  25                  30

Asn Lys Phe Lys His Gln Leu Ser Leu Thr Phe Ala Val Ser Ala Ser
        35                  40                  45

Met Leu Ala Trp Lys Asn Lys Ala Ile Tyr Ile Lys
    50                  55                  60

<210> SEQ ID NO 74
<211> LENGTH: 31
<212> TYPE: DNA
<213> ORGANISM: Artificial sequence
<220> FEATURE:
<223> OTHER INFORMATION: Dystrophin gene fragment

<400> SEQUENCE: 74
cattgttctc aggtacctca gccagcatgc t                              31

<210> SEQ ID NO 75
<211> LENGTH: 27
<212> TYPE: DNA
<213> ORGANISM: Artificial sequence
<220> FEATURE:
<223> OTHER INFORMATION: Dystrophin gene fragment

<400> SEQUENCE: 75
cattgttctc acctcagcca gcatgct                                   27

<210> SEQ ID NO 76
<211> LENGTH: 24
<212> TYPE: DNA
<213> ORGANISM: Artificial sequence
<220> FEATURE:
<223> OTHER INFORMATION: Dystrophin gene fragment

<400> SEQUENCE: 76
cattgttctc agagccagca tgct                                      24

<210> SEQ ID NO 77
<211> LENGTH: 27
<212> TYPE: DNA
```

```
<213> ORGANISM: Artificial sequence
<220> FEATURE:
<223> OTHER INFORMATION: Dystrophin gene fragment

<400> SEQUENCE: 77
cattgttctc agctcagcca gcatgct                                           27

<210> SEQ ID NO 78
<211> LENGTH: 24
<212> TYPE: DNA
<213> ORGANISM: Artificial sequence
<220> FEATURE:
<223> OTHER INFORMATION: Dystrophin gene fragment

<400> SEQUENCE: 78
cattgttctc acagccagca tgct                                              24

<210> SEQ ID NO 79
<211> LENGTH: 17
<212> TYPE: DNA
<213> ORGANISM: Artificial sequence
<220> FEATURE:
<223> OTHER INFORMATION: Dystrophin gene fragment

<400> SEQUENCE: 79
cattgttctc aggtact                                                      17

<210> SEQ ID NO 80
<211> LENGTH: 43
<212> TYPE: DNA
<213> ORGANISM: Artificial sequence
<220> FEATURE:
<223> OTHER INFORMATION: Dystrophin gene fragment

<400> SEQUENCE: 80
aatctaacaa gttcaaacac cagctctcct tgactttgc agt                          43

<210> SEQ ID NO 81
<211> LENGTH: 9
<212> TYPE: PRT
<213> ORGANISM: Artificial Sequence
<220> FEATURE:
<223> OTHER INFORMATION: Consensus sequence in homing endonuclease
      family

<400> SEQUENCE: 81

Leu Ala Gly Leu Ile Asp Ala Asp Gly
1               5
```